United States Patent
Sukhatme et al.

(10) Patent No.: US 9,539,323 B2
(45) Date of Patent: Jan. 10, 2017

(54) METHODS AND COMPOSITIONS FOR MALIC ENZYME 2 (ME2) AS A TARGET FOR CANCER THERAPY

(75) Inventors: Vikas P. Sukhatme, Newton, MA (US); Jian-Guo Ren, West Roxbury, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 364 days.

(21) Appl. No.: 13/814,614

(22) PCT Filed: Aug. 5, 2011

(86) PCT No.: PCT/US2011/046841
§ 371 (c)(1),
(2), (4) Date: Apr. 29, 2013

(87) PCT Pub. No.: WO2012/019154
PCT Pub. Date: Feb. 9, 2012

(65) Prior Publication Data
US 2013/0209488 A1 Aug. 15, 2013

Related U.S. Application Data

(60) Provisional application No. 61/371,488, filed on Aug. 6, 2010.

(51) Int. Cl.
*A61K 48/00* (2006.01)
*C07H 21/02* (2006.01)
(Continued)

(52) U.S. Cl.
CPC ......... *A61K 39/3955* (2013.01); *A61K 31/196* (2013.01); *A61K 31/198* (2013.01); *A61K 31/282* (2013.01); *A61K 31/335* (2013.01); *A61K 31/336* (2013.01); *A61K 31/337* (2013.01); *A61K 31/506* (2013.01); *A61K 31/555* (2013.01); *A61K 31/56* (2013.01); *A61K 31/7052* (2013.01); *A61K 31/713* (2013.01); *A61K 31/7105* (2013.01); *A61K 33/00* (2013.01); *A61K 33/24* (2013.01);
(Continued)

(58) Field of Classification Search
USPC ................................................ 536/23.1, 24.5
See application file for complete search history.

(56) References Cited

U.S. PATENT DOCUMENTS

2009/0181384 A1  7/2009  Nekarda et al.

FOREIGN PATENT DOCUMENTS

WO  WO9949065 A1 * 9/1999
WO  WO2004/091664 A1  10/2004

OTHER PUBLICATIONS

Loeber et al., GenBank Accesion P23386.1, downloaded from: http://www.ncbi.nlm.nih.gov/protein/126733?sat=12&satkey=10125064 on Mar. 1, 2012 (8 pages).

(Continued)

*Primary Examiner* — Terra C Gibbs
(74) *Attorney, Agent, or Firm* — Fish & Richardson P.C.

(57) ABSTRACT

The present invention relates to methods, compositions, and diagnostic tests for treating and diagnosing cancer and other related diseases that result in dysregulation of malic enzyme 2. In particular, the methods and compositions include combination therapy, such as with a combination of two or more ME2 inhibitors or a combination of an ME2 inhibitor and an anticancer agent.

14 Claims, 15 Drawing Sheets

(51) Int. Cl.
| | |
|---|---|
| C07H 21/04 | (2006.01) |
| C12N 15/11 | (2006.01) |
| A61K 39/395 | (2006.01) |
| A61K 31/196 | (2006.01) |
| A61K 31/282 | (2006.01) |
| A61K 31/336 | (2006.01) |
| A61K 31/506 | (2006.01) |
| A61K 31/56 | (2006.01) |
| A61K 31/7052 | (2006.01) |
| A61K 31/7105 | (2006.01) |
| A61K 33/24 | (2006.01) |
| A61K 38/52 | (2006.01) |
| A61K 45/06 | (2006.01) |
| G01N 33/574 | (2006.01) |
| A61K 31/198 | (2006.01) |
| A61K 31/335 | (2006.01) |
| A61K 31/337 | (2006.01) |
| A61K 31/555 | (2006.01) |
| A61K 31/713 | (2006.01) |
| A61K 33/00 | (2006.01) |
| C12N 15/113 | (2010.01) |

(52) U.S. Cl.
CPC .............. *A61K 38/52* (2013.01); *A61K 45/06* (2013.01); *G01N 33/57484* (2013.01); *C12N 15/1137* (2013.01); *C12N 2330/51* (2013.01); *C12Y 101/01037* (2013.01); *G01N 2333/904* (2013.01); *G01N 2500/10* (2013.01)

(56) References Cited

OTHER PUBLICATIONS

McGrath et al., "Protein expression in the nucleus accumbens of rats exposed to developmental vitamin D deficiency," *PloS One*, 3(6): e2383 (pp. 1-7) 2008.

Pongratz et al., "Cytosolic and mitochondrial malic enzyme isoforms differentially control insulin secretion," *J. Biol. Chem.* 282(1): 200-207, 2007.

Ren et al., "Induction of erythroid differentiation in human erythroleukemia cells by depletion of malic enzyme 2," *PloS One* 5(9): e12520 (pp. 1-12) 2010.

Sauer et al., "Mitochondrial Malic Enzymes," *J. Biol. Chem.* 255(9): 3844-3848, 1980.

Trejo et al., GenBank Accession P11708.4, downloaded from: http://www.ncbi.nlm.nih.gov/protein/6226874?sat=12 &satkey=10176265 on Mar. 1, 2012 (6 pages).

Wasilenko et al., "Malic enzyme and malate dehydrogenase activities in rat tracheal epithelial cells during the progression of neoplasia," *Cancer Lett.* 28(1): 35-42, 1985.

International Search Report and Written Opinion for International Application No. PCT/US11/46841, dated Apr. 9, 2012 (14 pages).

\* cited by examiner

METHODS AND COMPOSITIONS FOR MALIC ENZYME 2 (ME2) AS A TARGET FOR CANCER THERAPY

CROSS-REFERENCE TO RELATED APPLICATION

This application is the U.S. national stage filing under 35 U.S.C. 371 of International Application No. PCT/US2011/046841, filed Aug. 5, 2011, which claims the benefit of the filing date of U.S. Provisional Application No. 61/371,488, filed Aug. 6, 2010, each of which are hereby incorporated by reference in their entirety.

GOVERNMENT LICENSE RIGHTS

This invention was made with government support under Grant No. K01-CA 104700, awarded by the National Cancer Institute, and under Grant No. T32DK007199, awarded by the National Institute of Diabetes and Digestive and Kidney Diseases. The government has certain rights in the invention.

BACKGROUND OF THE INVENTION

The present invention relates to methods, compositions, and diagnostic tests for treating and diagnosing cancer and other related diseases that result in dysregulation of malic enzyme 2.

The progression and differentiation of tumor cells generally rely on increasing metabolism and altering normal physiological conditions. Thus far, the role of various enzymes in this metabolic process is yet unknown, and very little is known about the connection between metabolic activity, enzyme expression, and tumorigenesis. Malic enzyme 2 (ME2) is a mitochondrial enzyme that catalyzes the conversion of malate to pyruvate and $CO_2$ and uses NAD as a cofactor. Though ME2 is highly conserved over different species, the precise role of ME2 is not well-defined. Thus, many targets useful for cancer therapy (e.g., metabolic targets) have not yet been identified.

New therapeutic approaches and diagnostic methods are needed to treat or prevent cancer and related proliferative diseases.

SUMMARY OF THE INVENTION

We found that malic enzyme 2 (ME2) is expressed in various cancer cells, such as K562 erythroleukemia cells, in which a number of agents have been found to induce differentiation either along the erythroid or the myeloid lineage. Higher expression of this enzyme correlates with the degree of cell de-differentiation. We found that knockdown of ME2 led to diminished proliferation of tumor cells and increased apoptosis in vitro.

For K562 cells, these findings were accompanied by differentiation along the erythroid lineage, as confirmed by staining for glycophorin A and hemoglobin production. ME2 knockdown also totally abolished growth of K562 cells in nude mice. Increased ROS levels, likely reflecting increased mitochondrial production, and a decreased $NADPH/NADP^+$ ratio were noted, but use of a free radical scavenger to decrease inhibition of ROS levels did not reverse the differentiation or apoptotic phenotype, suggesting that ROS production is not causally involved in the resultant phenotype. As might be expected, depletion of ME2 induced an increase in the $NAD^+/NADH$ ratio, and ATP levels fell significantly. Inhibition of the malate-aspartate shuttle was insufficient to induce K562 differentiation. We also examined several intracellular signaling pathways and expression of transcription factors and intermediate filament proteins whose expression is known to be modulated during erythroid differentiation in K562 cells. We found that silencing of ME2 leads to phospho-ERK1/2 inhibition, phospho-AKT activation, increased GATA-1 expression, and diminished vimentin expression. Metabolomic analysis, conducted to gain insight into intermediary metabolic pathways that ME2 knockdown might affect, showed that ME2 depletion resulted in high orotate levels, suggesting potential impairment of pyrimidine metabolism. Without wishing to be limited by theory, ME2 likely acts via the ERK and/or PI3K/AKT pathways, as described herein, to reduce tumor growth and differentiation. Our data show that we have identified ME2 as a new target for cancer therapy in the rapidly evolving and exciting research area of tumor metabolism. Collectively, we describe ME2 as a potentially novel metabolic target for leukemia therapy.

Including leukemia, ME2 is likely a useful target for other types of cancers. We have extended these studies to cancer cells from solid tumors and have found that ME2 depletion in breast cancer cells (MCF-7), melanoma cells (WM983-B), and lung cancer cells (A549 and H1650) will also markedly inhibit growth in vitro and inhibit tumor growth in vivo. We also have evidence in some of these cell types that ME2 is promoting differentiation of the cells. Furthermore, we have observed increased expression of ME2 protein in different types of tumor tissues, including bladder, breast, esophagus, liver, lung, ovary, prostate, and skin. ME2 is also expressed in other tissues, including the brain (in neurons) and in the heart (in myocytes). Thus, inhibition of ME2 could be useful to treat cancers or diseases in these tissues.

Accordingly, the invention features methods and compositions for treating cancer and other diseases that result from increased activation of ME2. We have identified a new therapeutic target involving ME2 to treat cancer and other diseases, where the target includes one or more of ME2, proteins that regulate ME2, and genes that express ME2. These compositions of the invention include ME2 inhibitors, which can be identified by any useful method (e.g., chemical screening). These compounds include those that inhibit the enzymatic activity of ME2 (e.g., either directly or indirectly, such as by inhibiting fumarate, an activator of ME2) or those that decrease ME2 gene and/or protein expression. Compounds can be identified by any useful process, such as by screening a diverse library of compounds based on the ability of compounds to decrease NADH or NADPH formation, increase $NAD^+/NADH$ ratio, increase $NADP^+/NADPH$ ratio, increase ROS activity, decrease ATP levels, inhibit phospho-ERK1/2, activate phospho-AKT, increase GATA-1 expression, decrease vimentin expression, increase apoptosis, decrease cellular proliferation, decrease pyrimidine metabolism, decrease inosine levels, decrease uridine levels, and/or increase orotate levels in an assay (e.g., an in vitro cell assay or an in vivo assay).

In one aspect, the invention features a method of treating (e.g., prophylactically) a subject having cancer, the method including administering to the subject (e.g., a human subject) a malic enzyme 2 inhibitor in an amount sufficient to treat the cancer (e.g., a non-solid or a solid cancer).

In any of the embodiments described herein, the cancer is selected from the group consisting of leukemia (e.g., chronic myeloid leukemia, acute myeloid leukemia, acute lymphoblastic leukemia, and chronic lymphocytic leukemia), brain cancer (e.g., ependymoma, glioma, medulloblastoma, meningioma, teratoid rhabdoid tumor, and teratoma), bladder cancer (e.g., adenocarcinoma, sarcoma, small cell carcinoma, squamous cell carcinoma, and transitional cell carcinoma), breast cancer (e.g., breast ductal carcinoma), cervical cancer, colorectal cancer, endometrial cancer, esophageal cancer (e.g., adenocarcinoma and squamous cell carcinoma), head and neck cancer, liver cancer (e.g., hepatocellular carcinoma, cholangiocarcinoma, and hemangioendothelioma), lung cancer (e.g., non-small cell lung cancer, small-cell lung cancer, carcinoid, sarcoma, squamous cell cancer, adenocarcinoma, and large cell carcinoma), lymphoma (e.g., malignant lymphoma), ovarian cancer (e.g., ovarian epithelial carcinoma and teratoma), pancreatic cancer, prostate cancer (e.g., adenocarcinoma and prostatic intraepithelial neoplasia), renal cancer, skin cancer (e.g., basal cell carcinoma, squamous cell carcinoma, and malignant melanoma), stomach cancer, testis cancer, thyroid cancer, and urothelial cancer. In particular embodiments, the cancer has one or more mutations, such as non-small cell lung cancer having a T790M or a L747S mutation in EGFR kinase, a somatic activating mutation in the tyrosine-kinase pocket of EGFR (e.g., a deletion in exon 19 or a substitution in exon 21, e.g., L858R), or a mutation present in tyrosine kinase inhibitor-resistant cell line H1975; and brain cancer, breast cancer, colorectal cancer, lung cancer, or stomach cancer having a E542K, E545K, H1047R, P539R, or H1047L mutation in the PIK3CA gene (encoding a p110α of class IA of PI3K) (e.g., lung cancer having a H1047R mutation in PIK3CA).

For any of the methods or compositions described herein, the malic enzyme 2 inhibitor is an RNAi agent (e.g., an siRNA agent, an shRNA agent, a DsiRNA agent, and a miRNA agent, e.g., any of these agents that inhibits ME2 gene expression), S-oxalylglutathione or a derivative thereof, a lanthanide (e.g., lutetium, lanthanum, cerium, erbium, terbium, ytterbium, and holmium, as well as complexes thereof, such as lanthanide-labeled polyaminophosphonates, lanthanide-labeled antibodies, and lanthanide-labeled peptides), a steroid (e.g., pregnenolone), an anti-ME2 antibody (e.g., HPA008247 or HPA008880), a PI3K inhibitor (e.g., wortmannin, demethoxyviridin, LY294002, quercetin, myricetin, staurosporine, GDC-0941, NVP-BEZ235, ZSTK474, PX-866, and XL-147, e.g., wortmannin, e.g., LY294002), an RTK inhibitor (e.g., an EGFR inhibitor, an Her2 inhibitor, a PDGFR inhibitor, or an IGFR inhibitor, e.g., erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab, e.g., erlotinib, e.g., gefitinib), a PDK1 inhibitor (e.g., OSU-03012 and celecoxib), an AKT inhibitor (e.g., A-443654, GSK690693, VQD-002 (triciribine), and perifosine), or an mTOR inhibitor (e.g., an mTOR1 inhibitor or an mTOR2 inhibitor, e.g., rapamycin (sirolimus) and modified rapamycins (rapalogs), such as CCI-779 (temsirolimus), and RAD001 (everolimus)), and dual inhibitors of any of these proteins (e.g., a dual PI3K/mTOR inhibitor, such as NVP-BEZ235 and PI-103, or a dual AKT/PDK1 inhibitor, such as 6H-indeno[1,2-e]tetrazolo[1,5-b][1,2,4]triazin-6-one, 10H-indeno[2,1-e]tetrazolo[1,5-b][1,2,4]triazin-10-one, and PHT-427). Additional ME2 inhibitors can be identified by any useful method (e.g., as described herein).

In particular embodiments, the RNAi agent includes a nucleic acid sequence substantially identical (e.g., at least 50%, 60%, 70%, 75%, 80%, 85%, 90%, 95%, 96%, 97%, 98%, 99%, or 100% identical) to the sequence of any one of SEQ ID NOs:1-36. In some embodiments, the RNAi agent includes a nucleic acid sequence of any one of SEQ ID NOs:1-36.

In some embodiments, the method further includes administering to the subject an anticancer agent, where the malic enzyme 2 inhibitor and the anticancer agent are together in an amount sufficient to treat the cancer. In particular embodiments, the malic enzyme 2 inhibitor and the anticancer agent act synergistically.

For any of the methods or compositions described herein, the anticancer agent is one or more of a chemotherapeutic agent (e.g., arsenic trioxide, cisplatin, carboplatin, chlorambucil, melphalan, nedaplatin, oxaliplatin, triplatin tetranitrate, satraplatin, imatinib, nilotinib, dasatinib, and radicicol, e.g., cisplatin), an immunomodulatory agent (e.g., methotrexate, leflunomide, cyclophosphamide, cyclosporine A, minocycline, azathioprine, an antibiotic (e.g., tacrolimus), methylprednisolone, a corticosteroid, a steroid, mycophenolate mofetil, rapamycin, mizoribine, deoxyspergualin, brequinar, a T cell receptor modulator, and a cytokine receptor modulator, e.g., methotrexate), an antiangiogenic agent (e.g., bevacizumab, suramin, and etrathiomolybdate), a mitotic inhibitor (e.g., paclitaxel, vinorelbine, docetaxel, abazitaxel, ixabepilone, larotaxel, ortataxel, tesetaxel, vinblastine, vincristine, vinflunine, and vindesine, e.g., paclitaxel), a nucleoside analog (e.g., gemcitabine, azacitidine, capecitabine, carmofur, cladribine, clofarabine, cytarabine, decitabine, floxuridine, fludarabine, fluorouracil, mercaptopurine, pentostatin, tegafur, and thioguanine, e.g., gemcitabine), a DNA intercalating agent (e.g., doxorubicin, actinomycin, bleomycin, mitomycin, and plicamycin, e.g., doxorubicin), a topoisomerase analog (e.g., irinotecan, aclarubicin, amrubicin, belotecan, camptothecin, daunorubicin, epirubicin, etoposide, idarubicin, mitoxantrone, pirarubicin, pixantrone, rubitecan, teniposide, topotecan, valrubicin, and zorubicin, e.g., irinotecan), a folate antimetabolite (e.g., pemetrexed, aminopterin, methotrexate, pralatrexate, and raltitrexed, e.g., pemetrexed), or other targeting agents (e.g., agents that target particular enzymes or proteins involved in cancer or agents that target particular organs or types of cancers), and combinations thereof.

The invention also features a composition including a malic enzyme 2 inhibitor and an anticancer agent. In some embodiments, the malic enzyme 2 inhibitor and the anticancer agent together are present in an amount sufficient to treat cancer. In other embodiments, the malic enzyme 2 inhibitor or the anticancer agent is present in an amount sufficient to treat cancer. In particular embodiments, the malic enzyme 2 inhibitor and the anticancer agent act synergistically.

In particular embodiments, the composition includes a malic 2 enzyme inhibitor that is an RNAi agent (e.g., any described herein, such as an RNAi agent including a nucleic acid sequence substantially identical (e.g., at least 50%, 60%, 70%, 75%, 80%, 85%, 90%, 95%, 96%, 97%, 98%, 99%, or 100% identical) to the sequence of any one of SEQ ID NOs:1-36) and an anticancer agent, e.g., any described herein.

The invention also features a composition including two or more malic enzyme 2 inhibitors, e.g., any described herein. In particular embodiments, the two or more malic enzyme 2 inhibitors act synergistically.

In some embodiments, the composition includes a malic 2 enzyme inhibitor that is an RNAi agent (e.g., any described herein, such as an RNAi agent including a nucleic acid sequence substantially identical (e.g., at least 50%, 60%, 70%, 75%, 80%, 85%, 90%, 95%, 96%, 97%, 98%, 99%, or 100% identical) to the sequence of any one of SEQ ID NOs:1-36) and another malic enzyme 2 inhibitor that is not an RNAi agent, such as any described herein (e.g., the combination of an RNAi agent and a PI3K inhibitor (e.g., wortmannin, demethoxyviridin, LY294002, quercetin, myricetin, staurosporine, GDC-0941, NVP-BEZ235, ZSTK474, PX-866, and XL-147, e.g., wortmannin, e.g., LY294002); the combination of an RNAi agent and an RTK inhibitor (e.g., erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab, e.g., erlotinib, e.g., gefitinib); the combination of an RNAi agent and a non-specific PDK1 inhibitor, such as any described herein; the combination of an RNAi agent and an AKT inhibitor, such as any described herein; the combination of an RNAi agent and a dual AKT/PDK1 inhibitor, such as any described herein; the combination of an RNAi agent and an mTOR inhibitor, such as any described herein; and the combination of an RNAi agent and a dual PI3K/mTOR inhibitor, such as any described herein).

In other embodiments, the composition includes a malic 2 enzyme inhibitor that is an anti-ME2 antibody (e.g., HPA008247 and HPA008880) and another malic enzyme 2 inhibitor that is not an anti-ME2 antibody, such as any described herein (e.g., a combination of an anti-ME2 antibody and an RNAi agent (e.g., any described herein, such as an RNAi agent including a nucleic acid sequence substantially identical (e.g., at least 50%, 60%, 70%, 75%, 80%, 85%, 90%, 95%, 96%, 97%, 98%, 99%, or 100% identical) to the sequence of any one of SEQ ID NOs:1-36); an anti-ME2 antibody and a PI3K inhibitor (e.g., wortmannin, demethoxyviridin, LY294002, quercetin, myricetin, staurosporine, GDC-0941, NVP-BEZ235, ZSTK474, PX-866, and XL-147, e.g., wortmannin, e.g., LY294002); an anti-ME2 antibody and an RTK inhibitor (e.g., erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab, e.g., erlotinib, e.g., gefitinib); an anti-ME2 antibody and a non-specific PDK1 inhibitor, such as any described herein; an anti-ME2 antibody and an AKT inhibitor, such as any described herein; an anti-ME2 antibody and a dual AKT/PDK1 inhibitor, such as any described herein; an anti-ME2 antibody and an mTOR inhibitor; and an anti-ME2 antibody and a dual PI3K/mTOR inhibitor.

The invention also features a method for diagnosing a subject as having or having a predisposition to a disease having an increased activation of malic enzyme 2, the method including determining the level of malic enzyme 2 activity in a sample from the subject and comparing the level of malic enzyme 2 activity with a normal reference sample, where the presence of an increased level of malic enzyme 2 activity (e.g., an increased level of malic enzyme 2 activity of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample), as compared to the normal reference sample, results in diagnosing the subject as having, or having a predisposition to, the disease.

In some embodiments, the disease is cancer and the cancer is selected from the group consisting of leukemia, brain cancer, bladder cancer, breast cancer, cervical cancer, colorectal cancer, endometrial cancer, esophageal cancer, head and neck cancer, liver cancer, lung cancer, lymphoma, ovarian cancer, pancreatic cancer, prostate cancer, renal cancer, skin cancer, stomach cancer, testis cancer, thyroid cancer, and urothelial cancer, or any described herein.

The invention also features a method for identifying a malic enzyme 2 inhibitor, the method including contacting a cell with a candidate compound, determining the level of malic enzyme 2 activity in the cell, and comparing the level of malic enzyme 2 activity with a normal reference sample, where the presence of a decreased level of malic enzyme 2 activity in the cell (e.g., a decreased level of malic enzyme 2 activity of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample), as compared to the normal reference sample, results in identifying the candidate compound as a malic enzyme 2 inhibitor.

In any of the methods described herein, the level of malic enzyme 2 activity is one or more (e.g., two, three, four, five, six, seven, eight, nine, ten, or more) of levels of ME2, AKT1/2, AKT1, AKT2, ERK1/2, ERK1, GATA-1, PI3K, PDK1, mTOR1/2, mTOR2, EGFR, Her2, PDGFR, IGFR, vimentin, NADH, NADPH, $NAD^+$/NADH ratio, $NADP^+$/NADPH ratio, ROS, ATP, inosine, uridine, or orotate. In other embodiments, the level of malic enzyme 2 activity is one or more of a cellular parameter (e.g., apoptosis, proliferation, and pyrimidine metabolism). In yet other embodiments, the level of malic enzyme 2 activity is one or more of level of analytes in Table 1.

In particular embodiments, such as for diagnosing a subject, the level of malic enzyme 2 activity is one or more (e.g., two, three, four, five, six, seven, eight, nine, ten, or more) of increased NADH or NADPH formation, decreased $NAD^+$/NADH ratio, decreased $NADP^+$/NADPH ratio, decreased ROS activity, increased ATP levels, activation of phospho-ERK1/2, deactivation of phospho-AKT, decreased GATA-1 expression, increased vimentin expression, decreased apoptosis, increased proliferation, increased pyrimidine metabolism, increased inosine levels, increased uridine levels, or decreased orotate levels, as compared to a control or a normal reference sample. In particular embodiments, such as for identifying a malic enzyme 2 inhibitor, the level of malic enzyme 2 activity is one or more of decreased NADH formation (e.g., from 3-fold to 4-fold decreased formation), decreased NADPH formation (e.g., from 5-fold to 10-fold, e.g., about 7 fold, decreased formation), increased $NAD^+$/NADH ratio (e.g., from 1.5-fold to 3-fold, e.g., about 2-fold, increased ratio), increased $NADP^+$/NADPH ratio (e.g., from 5-fold to 15-fold, e.g., about 9-fold, increased ratio), increased ROS activity, decreased ATP levels (e.g., from 2-fold to 4-fold, e.g., about 3-fold, decreased levels), inactivation of phospho-ERK1/2, activation of phospho-AKT, increased GATA-1 expression, decreased vimentin expression, increased apoptosis, decreased cellular proliferation, decreased pyrimidine metabolism, decreased inosine levels (e.g., from 5-fold to 10-fold, e.g., about 6-fold, decreased levels), decreased uridine levels (e.g., from 5-fold to 10-fold, e.g., about 6-fold, decreased levels), or increased orotate levels (e.g., from 50-fold to 150-fold, e.g., 75-fold to 150-fold, e.g., about 90-fold, increased levels), as compared to a control or a normal reference sample (e.g., a sample from a subject that has been treated for a disease associated with increased activity of ME2, e.g., cancer; or a sample of purified ME2 at a known normal concentration). In particular embodiments, the level of malic enzyme 2 activity is increased orotate levels (e.g., from 50-fold to 150-fold, e.g., 75-fold to 150-fold, e.g., about 90-fold, increased levels). In other embodiments, the level of malic enzyme 2 activity is decreased orotate levels (e.g., from 50-fold to 150-fold, e.g., 75-fold to 150-fold, e.g., about 90-fold, decreased levels).

The invention further features methods and compounds related to increased activation of ME2 and cancer. For example, ME2 activity can be studied by determining the toxicity of global ME2 knockdown in animals. Thus, the invention also includes methods and compositions to observe ME2 knockdown (e.g., an ME2 knockout mouse and methods for developing an ME2 knockout mouse; or an RNAi agent for ME2 and methods for making this agent, such as a shRNA ME-2 construct).

The invention also features methods, compositions, and diagnostic tests for diagnosing cancer and other diseases that result from increased activation of ME2. The diagnostic methods and tests could aid in identifying patients who are at risk of developing cancer related to ME2 activity. The methods described herein can be used to identify patients who are at risk by determining the activity of ME2 (e.g., by using any of the methods described herein). The methods described herein can be used to identify patients with increased ME2 activity and to treat these patients by using any of the methods or compositions described herein.

In particular embodiments, a diagnostic test or method is used to predict the risk of a patient in developing cancer (e.g., leukemia). A diagnostic test or method can include a screen for the activity of ME2 by any useful detection method (e.g., fluorescence, radiation, or spectrophotometry). A diagnostic test can further include probes and primers to detect the expression of the ME2 gene. In certain embodiments, the diagnostic test includes the use of the activity of ME2 in a diagnostic platform, which can be optionally automated. Further, the diagnostic tests disclosed herein can be used to determine an optimal treatment plan for a patient. For example, the presence of increased activity of ME2 includes a treatment plan of administering an ME2 inhibitor.

Other features and advantages of the invention will be apparent from the following description and the claims.

DEFINITIONS

As used herein, the term "about" means±10% of the recited value.

By "amount sufficient" of an agent is meant the amount of the agent sufficient to effect beneficial or desired results, such as clinical results, and, as such, an amount sufficient depends upon the context in which it is applied. For example, in the context of administering a composition that reduces the expression level of ME2, the amount sufficient of the formulation is an amount sufficient to achieve a reduction in the expression level of the ME2 gene or protein, as compared to the response obtained without administration of the composition.

By "Dicer-substrate RNA" or "DsiRNA" is meant a class of 25-35 (e.g., 25-27, such as 27) nucleotide double-stranded molecules that are capable of gene silencing. Due to its longer length compared to other RNAi agents, DsiRNA are likely substrates of Dicer.

By "double-stranded molecule" is meant a double-stranded RNA:RNA or RNA:DNA molecule that can be used to silence a gene product through RNA interference.

By "expression" is meant the detection of a gene or polypeptide by methods known in the art. For example, DNA expression is often detected by Southern blotting or polymerase chain reaction (PCR), and RNA expression is often detected by Northern blotting, RT-PCR, gene array technology, or RNAse protection assays. Methods to measure protein expression level generally include, but are not limited to, Western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), and flow cytometry, as well as assays based on a property of the protein including, but not limited to, enzymatic activity or interaction with other protein partners.

By "hybridize" is meant to pair to form a double-stranded molecule between sufficiently complementary polynucleotides, as defined herein, or portions thereof, under various conditions of stringency. (See, e.g., Wahl et al., *Methods Enzymol.* 152:399 (1987); Kimmel, *Methods Enzymol.* 152: 507 (1987)). For example, high stringency salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. High stringency temperature conditions will ordinarily include temperatures of at least about 30° C., 37° C., or 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In an alternative embodiment, hybridization will occur at 50° C. or 70° C. in 400 mM NaCl, 40 mM PIPES, and 1 mM EDTA, at pH 6.4, after hybridization for 12-16 hours, followed by washing. Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. Useful variations on these conditions will be readily apparent to those skilled in the art.

By "increased activity" or "increased activation" of ME2 is meant an increase in ME2 gene expression, protein expression, or enzymatic activity, as compared to a control from a normal cell or normal tissue (e.g., an increase of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample). Increased activity can be determined using any useful methods known in the art or described herein. For example, an increase in activity can be determined as an increase in ME2 gene expression or increased ME2 protein concentration (e.g., as determined by PCR or by gel electrophoresis), as compared to a control (e.g., a sample including normal cell or normal tissue from one or more healthy subjects) or a normal reference sample, as defined herein. In another example, an increase in activity can be determined as an increase in ME2 enzymatic activity, such as by measuring increased NADH formation (e.g., from 3-fold to 4-fold increased formation), increased NADPH formation (e.g., from 5-fold to 10-fold, e.g., about 7 fold, increased formation), decreased $NAD^+/NADH$ ratio (e.g., from 1.5-fold to 3-fold, e.g., about 2-fold, decreased ratio), or decreased $NADP^+/NADPH$ ratio (e.g., from 5-fold to 15-fold, e.g., about 9-fold, decreased ratio), as compared to a control or a normal reference sample. Increased activity can be measured directly (e.g., increased ME2 gene expression or increased ME2 enzymatic activity) or indirectly, such as by measuring levels of one or more analytes associated with increased ME2 activity (e.g., by measuring one or more of decreased ROS activity, increased ATP levels (e.g., from 2-fold to 4-fold, e.g., about 3-fold, increased levels), activation of phospho-ERK1/2, deactivation of phospho-AKT, decreased GATA-1 expression, increased vimentin expression, decreased apoptosis, increased proliferation, increased pyrimidine metabolism, increased inosine levels (e.g., from 5-fold to 10-fold, e.g., about 6-fold, increased levels), increased uridine levels (e.g., from 5-fold to 10-fold, e.g., about 6-fold, increased levels), or decreased orotate levels (e.g., from 50-fold to 150-fold, e.g., from 75-fold to 150-fold, e.g., about 90-fold, decreased levels), as compared to a control or a normal reference sample.

By "malic enzyme 2 inhibitor" or "ME2 inhibitor" is meant any agent or compound that decreases or reduces ME2 gene expression, protein expression, or enzymatic activity, as defined herein, compared to a control (e.g., a decrease by 5%, 10%, 15%, 20%, 25%, 30%, 35%, 40%, 45%, 50%, 55%, 60%, 65%, 70%, 75%, 80%, 85%, 90%, or 95%, as compared to a control or a normal reference sample). ME2 inhibitors can be identified and tested by any useful method (e.g., any described herein). ME2 includes *Homo sapiens* mRNA (NCBI RefSeq no. NM_002396.4 and Entrez Gene No. 4200) (SEQ ID NO:40), *Homo sapiens* DNA (NCBI RefSeq nos. NC_000018.9 and NT_010966.14), and *Homo sapiens* protein (UniProtKB reference no. P23368 and NCBI RefSeq nos. NP_001161807.1 and NP_002387.1).

By "microRNA" (miRNA) is meant a single-stranded RNA molecule that can be used to silence a gene product through RNA interference.

By "modulate" is meant that the expression of a gene, or level of an RNA molecule or equivalent RNA molecules encoding one or more proteins or protein subunits, or activity of one or more proteins or protein subunits is up-regulated or down-regulated, such that expression, level, or activity is greater than or less than that observed in the absence of the modulator. For example, the term modulate can include inhibition or gene silencing, and the level of expression of a gene or the level of an RNA molecule, or an equivalent thereof, is reduced by at least 10% (e.g., 15%, 20%, 25%, 30%, 35%, 40%, 50%, 60%, 70%, 80%, 85%, 90%, 95%, 97%, 98%, 99%, or 100%), as compared to a control.

By "pharmaceutical composition" is meant a composition containing a compound described herein formulated with a pharmaceutically acceptable excipient, and manufactured or sold with the approval of a governmental regulatory agency as part of a therapeutic regimen for the treatment of disease in a mammal Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

By "pharmaceutically acceptable excipient" is meant any ingredient other than the compounds described herein (for example, a vehicle capable of suspending or dissolving the active compound) and having the properties of being non-toxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

By "pharmaceutically acceptable salt" is meant those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharm. Sci.* 66(1):1, 1977 and in *Pharmaceutical Salts: Properties, Selection, and Use*, P. H. Stahl and C. G. Wermuth (eds.), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, and the like.

By "reference sample" is meant any sample, standard, standard curve, or level that is used for comparison purposes. A "normal reference sample" can be, for example, a prior sample taken from the same subject; a sample from a normal healthy subject; a sample from a subject not having a disease associated with increased activity of ME2, e.g., cancer; a sample from a subject that is diagnosed with a propensity to develop a disease associated with increased activity of ME2, e.g., cancer, but does not yet show symptoms of the disorder; a sample from a subject that has been treated for a disease associated with increased activity of ME2, e.g., cancer; or a sample of purified ME2 at a known normal concentration. By "reference standard or level" is meant a value or number derived from a reference sample. A normal reference standard or level can be a value or number derived from a normal subject who does not have a disease associated with increased activity of ME2, e.g., cancer. In preferred embodiments, the reference sample, standard, or level is matched to the sample subject by at least one of the following criteria: age, weight, sex, disease stage, and overall health. A standard curve of levels of a purified ME2 protein or gene within the normal reference range can also be used as a reference.

By "RNAi agent" is meant any agent or compound that exerts a gene silencing effect by hybridizing a target nucleic acid. RNAi agents include any nucleic acid molecules that are capable of mediating sequence-specific RNAi (e.g., under stringent conditions), for example, a short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically-modified siRNA, post-transcriptional gene silencing RNA (ptg-sRNA), and Dicer-substrate RNA (DsiRNA).

By "sense region" is meant a nucleotide sequence having sufficient complementarity to an antisense region of another nucleic acid. In addition, the sense region of a nucleic acid of the invention can include a nucleotide sequence having homology with a target gene nucleotide sequence. By "antisense region" is meant a nucleotide sequence having sufficient complementarity to a target gene nucleotide sequence.

By "short hairpin RNA" or "shRNA" is meant a sequence of RNA that makes a tight hairpin turn and is capable of gene silencing.

By "silencing" or "gene silencing" is meant that the expression of a gene or the level of an RNA molecule that encodes one or more proteins is reduced in the presence of an RNAi agent below that observed under control conditions (e.g., in the absence of the RNAi agent or in the presence of an inactive or attenuated molecule such as an RNAi molecule with a scrambled sequence or with mismatches). Gene silencing may decrease gene product expression by 1%, 2%, 3%, 4%, 5%, 6%, 7%, 8%, 9%, 10%, 15%, 20%, 25%, 30%, 35%, 40%, 50%, 60%, 70%, 80%, 85%, 90%, 95%, 97%, 98%, 99%, or 100% (i.e., complete inhibition).

By "small inhibitory RNA," "short interfering RNA," or "siRNA" is meant a class of 10-40 (e.g., 15-25, such as 21) nucleotide double-stranded molecules that are capable of gene silencing. Most notably, siRNA are typically involved in the RNA interference (RNAi) pathway by which the siRNA interferes with the expression of a specific gene product.

By "subject" is meant a mammal (e.g., a human).

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "sufficiently complementary" is meant a polynucleotide sequence that has the exact complementary polynucleotide sequence, as a target nucleic acid, or has a specified percentage or nucleotides that are the exact complement at the corresponding location within the target nucleic acid when the two sequences are optimally aligned. For example, a polynucleotide sequence that is "substantially complementary" to a target nucleic acid sequence has at least 50%, 60%, 70%, 75%, 80%, 85%, 90%, 95%, 96%, 97%, 98%, 99%, or 100% complementarity to the target nucleic acid sequence. For RNAi agents having a length between 10 to 40 nucleotides, sufficiently complementary sequences include those having one, two, three, four, or five non-complementary nucleotides.

By "target nucleic acid" is meant any nucleic acid sequence whose expression or activity is to be modulated. The target nucleic acid can be DNA or RNA.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. By "treating cancer" or "inhibiting cancer" is meant causing a reduction in the size of a tumor or the number of cancer cells, slowing or inhibiting an increase in the size of a tumor or cancer cell proliferation, increasing the disease-free survival time between the disappearance of a tumor or other cancer and its reappearance, reducing the likelihood of an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay. Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of cancerous cells as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after no less than 5, 10, 15, or 20 years. By "prophylactically treating" or "preventing" a disease or condition (e.g., cancer) in a subject is meant reducing the risk of developing (i.e., the incidence) of or reducing the severity of the disease or condition prior to the appearance of disease symptoms. The prophylactic treatment may completely prevent or reduce appears of the disease or a symptom thereof and/or may be therapeutic in terms of a partial or complete cure for a disease and/or adverse effect attributable to the disease. Prophylactic treatment may include reducing or preventing a disease or condition (e.g., preventing cancer) from occurring in an individual who may be predisposed to the disease but has not yet been diagnosed as having it.

Other features and advantages of the invention will be apparent from the following Detailed Description and the claims.

DETAILED DESCRIPTION

Figure 1:
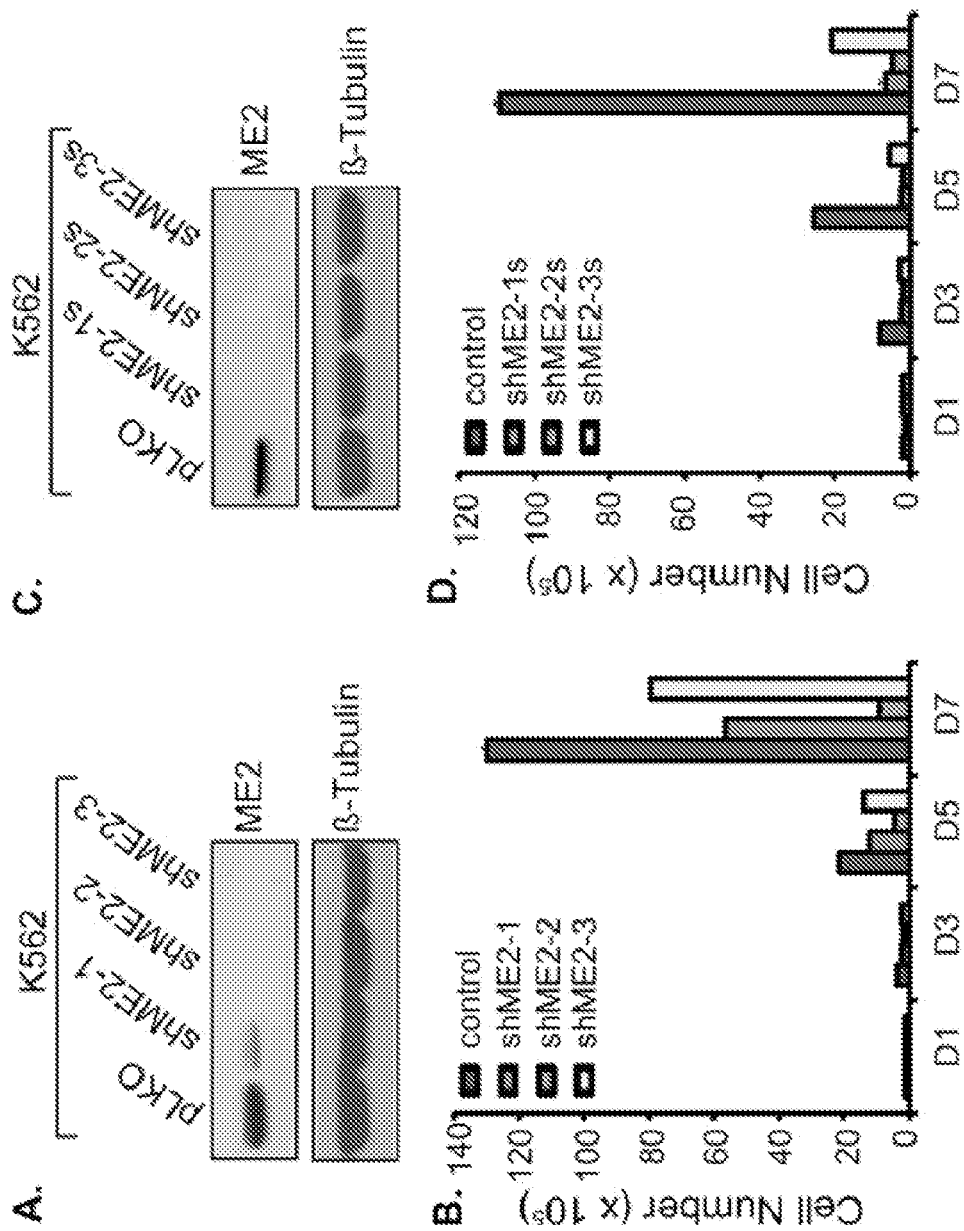
FIG. 1 shows the effects on K562 cell proliferation of three independent shRNA hairpins targeting ME2. A: Western blot analysis using an ME2 antibody of lysate from respective pools of cells transduced with three independent ME2 shRNA lentiviruses, and following selection of puromycin for 10 days. Data are representative of two independent experiments. All three pools showed marked ME2 silencing. B: Cell proliferation in K562 cells transduced with the indicated shRNA lentiviral constructs as described in "A." Data are representative of three independent experiments. Data are shown for control (first bar for each day D1, D3, D5, and D7), shME2-1 (second bar for each day), shME2-2 (third bar for each day), and shME2-3 (fourth bar for each day). C: Western blot analysis of cellular extracts in single clone K562 demonstrated effective knockdown of ME2 levels. Data are representative of two independent experiments. D: Cell proliferation of K562 single cell clones with ME2 knockdown derived from the corresponding pools as described in "C." Data are representative of three independent experiments.

We have discovered that knockdown or inhibition of ME2 leads to diminished proliferation of tumor cells and increased apoptosis. In particular, higher expression of ME2 is associated with various types of cancer cells, such as those for leukemia cells (K562), breast cancer cells (MCF-7), melanoma cells (WM983-B), and lung cancer cells (A549 and H1650). Accordingly, the compositions and methods described herein can be useful for treating a disease, e.g., cancer, associated with increased activity of ME2. Examples of compositions include an ME2 inhibitor, a combination of two or more ME2 inhibitors, or a combination of an ME2 inhibitor and an anticancer agent. Examples of compositions and diseases are described in detail below.

ME2 inhibitors

ME2 inhibitors include one or more compounds that directly or indirectly inhibit ME2 gene expression, protein expression, or enzymatic activity. Exemplary ME2 inhibitors include an RNAi agent (e.g., a shRNA for ME2, as described herein), an anti-ME2 antibody, S-oxalylglutathione and derivatives thereof, lanthanides (e.g., lutetium, lanthanum, cerium, erbium, terbium, ytterbium, and holmium, as well as complexes thereof, such as lanthanide-labeled polyaminophosphonates, lanthanide-labeled antibodies, and lanthanide-labeled peptides), steroids (e.g., pregnenolone), and inhibitors of one or more proteins selected from the group of PI3K, RTK (e.g., EGFR, Her2, PDGFR, or IGFR), PDK1, AKT, mTOR (e.g., mTOR1 or mTOR2), and dual inhibitors of any of these proteins. Additional ME2 inhibitors can be identified by any useful method, such as by inhibiting or activating one or more proteins upstream of ME2 in the PI3/AKT pathway that results in ME2 inhibition.

RNAi Agents

ME2 inhibitors include one or more RNAi agents that inhibit ME2 gene expression in a cell in vitro or in vivo (e.g., in a subject). The RNAi agents can include different types of double-stranded molecules that include either RNA:RNA or RNA:DNA strands. These agents can be introduced to cells in a variety of structures, including a duplex (e.g., with or without overhangs on the 3'-terminus), a hairpin loop, or an expression vector that express one or more polynucleotides capable of forming a double-stranded polynucleotide alone or in combination with another polynucleotide.

Exemplary RNAi agents include siRNA, shRNA, DsiRNA, and miRNA agents. Generally, these agents are about 10 to about 40 nucleotides in length, and preferred lengths for particular RNAi agents include siRNA that are double-stranded RNA molecules of 16 to 30 nucleotides in length (e.g., 18 to 25 nucleotides, e.g., 21 nucleotides); shRNA that are single-stranded RNA molecules in which a hairpin loop structure is present and a stem length is between 19 to 29 nucleotides in length (e.g., 19 to 21 nucleotides or 25 to 29 nucleotides) or a loop size is between 4 to 23 nucleotides in length; DsiRNA that are double-stranded RNA agents of 25 to 35 nucleotides in length; and miRNA that are single-stranded RNA molecules of 17 to 25 nucleotides (e.g., 21 to 23 nucleotides) in length.

The RNAi agent can have any useful nucleic acid sequence, including a nucleic acid sequence having one or more DNA molecules, RNA molecules, or modified forms (e.g., a modified backbone composition or 2'-deoxy- or 2'-O-methyl modifications) or combinations thereof. Additionally, the RNAi agent can contain 5'- and/or 3'-terminal modifications and include blunt and overhanging nucleotides at these termini, or combinations thereof. Exemplary modifications include a 5'-dideoxythymidine overhang, such as for siRNAi; a 3'-UU or 3'-dTdT overhang, such as for shRNA; one or more G-U mismatches between the two strands of the shRNA stem; or a single-stranded nucleotide overhang at the 3'-terminal of the antisense or sense strand of 1 to 4 nucleotides (e.g., 1 or 2 nucleotides) for DsiRNA.

Methods of producing antisense and sense nucleotides, as well as corresponding duplexes or hairpin loops, are known in the art and can be readily adapted to produce an antisense oligonucleotide that targets any target nucleic acid sequence. RNAi agents include at least one antisense nucleotide sequence that is directed to a target nucleic acid (e.g., a target gene, e.g., an ME2 gene). Antisense nucleotides are single strands of DNA or RNA that are complementary to a chosen target sequence. In the case of antisense RNA, they prevent translation of complementary RNA strands by binding to it. Antisense DNA can be used to target a specific, complementary (coding or non-coding) RNA. In a particular embodiment, antisense nucleotides contain from about 10 to about 40 nucleotides, more preferably about 15 to about 30 nucleotides. The antisense nucleotide can have up to 80%, 85%, 90%, 95%, 99%, or even 100% complementary to the desired target gene ME2 inhibitors include one or more RNAi agents. Exemplary RNAi agents include shRNA agents, such as CGGCATATTAGTGACAGTGTT (shME2-1 sense, SEQ ID NO:1), CCCAGTATGGACACATCTTTA (shME2-2 sense, SEQ ID NO:2), GCACGGCTGAAGA AGCATATA (shME2-3 sense, SEQ ID NO:3), TTAGATCAATTGTG-GATAACTGGCC AGAA (sense, SEQ ID NO:4), GAAGACTTTGGAAATCATAATGCATTCAG (sense, SEQ ID NO:5), GCGAGTCTTTACACCAGGT-CAAGGAAACA (sense, SEQ ID NO:6), CCAGG TGTG-GCTTTAGCTGTTATTCTCTG (sense, SEQ ID NO:7), TGCTGTTGACAGTGAGCGCGCCACTTATGCTGAAC-CCAAGTAGTGAAGCC ACAGATGTACTTGGGTTCA-GCATAAGTGGCTTGCCTACTGCCTCGGA (V2HS_151676, SEQ ID NO:8), TGCTGTTGACAGT-GAGCGACAAGATGACATTGAGAGTTTATAGT-GAAGCC ACAGATGTATAAACTCTCAATGTCATCTT-GCTGCCTACTGCCTCGGA (V2HS_151677, SEQ ID NO:9), TGCTGTTGACAGTGAGCGCGGT-CAAGGAAACAATGTTTATTAGTGAAGCC ACAGAT-GTAATAAACATTGTTTCCTTGACCTTGCCTACTGC-CTCGGA (V2HS_151680, SEQ ID NO:10), TGCTGTTGACAGTGAGCGATAGGAAAACTTTGTTT-GTATATAGTGAAGCC ACAGATGTATATA-CAAACAAAGTTTTCCTACTGCCTACTGCCTCGGA (V3LHS_392891, SEQ ID NO:11), TGCTGTTGACAGT-GAGCGACAGAAACGA GATCGCACACAATAGT-GAAGCCACAGATGTATTGTGTGCGATCTCGTTTCT GGTGCCTACTGCCTCGGA (V3LHS_392894, SEQ ID NO:12), TGCTGTTGACA GTGAGCGACT-GAAGAAGCATATACACTTATAGTGAAGCCACAGAT-GTATA AGTGTATATGCTTCTTCAGCTGCCTACTGC-CTCGGA (V3LHS_392895, SEQ ID NO:13), CCGGCGGCATATTAGTGACAGTGTTCTCGA-GAACACTGTCA CTAATATGCCGTTTTTG (TRCN0000064738, SEQ ID NO:14), CCGGGAAAGC TATTACTGACAGATACTCGAGTATCTGTCAG-TAATAGCTTTCTTTTTG (TRCN0000064740, SEQ ID NO:15), CCGGCCCAGTATGGACACATCTTTA CTC-GAGTAAAGATGTGTCCATACTGGGTTTTTG (TRCN0000064741, SEQ ID NO:16), CCGGGCACGGCT- GAAGAAGCATATACTCGAGTATATGCTTCTTCA GCCGTGCTTTTG (TRCN0000064742, SEQ ID NO:17), CCGGTACTTTG GCATGTCGACATTTCTCGAGAAAT-GTCGACATGCCAAAGTATTTTTG (TRCN0000294005, SEQ ID NO:18), and CCGGAGTTCTTACAGAGCTACT AAACTCGAGTTTAGTAGCTCTGTAAGAACTTTTTTG (TRCN0000294007, SEQ ID NO:19); and siRNA agents, such as CCACTTATGCTGAACCCAA (mature sense for V2HS_151676, SEQ ID NO:20) and 3'-TTGGGTTCAG-CATAAGTGG-5' (mature antisense for V2HS_151676, SEQ ID NO:21), GTCAAGGAAACAATGTTTA (mature sense for V2HS_151680, SEQ ID NO:22) and 3'-TAAACATTGTTTCCTTGAC-5' (mature antisense for V2HS_151680, SEQ ID NO:23), AAGATGACATT-GAGAGTTT (mature sense for V2HS_151677, SEQ ID NO:24) and 3'-AAACTCTCAATGTCATCTT-5' (mature antisense for V2HS_151677, SEQ ID NO:25), TGAAGAAGCATATACACTT (mature sense for V3LHS_392895, SEQ ID NO:26) and 3'-AAGTGTATAT-GCTTCTTCA-5' (mature antisense for V3LHS_392895, SEQ ID NO:27), AGGAAAACTTTGTTTGTAT (mature sense for V3LHS_392891, SEQ ID NO:28) and 3'-ATA-CAAACAAAGTTTTCCT-5' (mature antisense for V3LHS_392891, SEQ ID NO:29), AGAAACGAGATCG-CACACA (mature sense for V3LHS_392894, SEQ ID NO:30) and 3'-TGTGTGCGATCTCGTTTCT-5' (mature antisense for V3LHS_392894, SEQ ID NO:31), CGGCAT-ATTAGTGACAGTGTT (sense for TRCN0000064738, SEQ ID NO:1) and 3'-AACACTGTCACTAATATGCCG-5' (antisense for TRCN0000064738, SEQ ID NO:32), GAAAGCTATTACTGACAGATA (mature sense for TRCN0000064740, SEQ ID NO:33) and 3'-TATCTGTCA-GTAATAGCTTTC-5' (mature antisense for TRCN0000064740, SEQ ID NO:34), CCCAGTATGGA-CACATCTTTA (mature sense for TRCN0000064741, SEQ ID NO:2) and 3'-TAAAGATGTGTCCATACTGGG-5' (mature antisense for TRCN0000064741, SEQ ID NO:35), and GCACGGCTGAAGAAGCATATA (mature sense for TRCN0000064742, SEQ ID NO:3) and 3'-TATATGCTTCT-TCAGCCGTGC-5' (mature antisense for TRCN0000064742, SEQ ID NO:36), where sequences are provided in the 5' to 3' direction, unless otherwise specified. RNAi agents also include commercially available agents, such as those available from OriGene Technologies (Rockville, Md.) and Santa Cruz Biotechnologies, Inc. (Santa Cruz, Calif.).

Other ME2 Inhibitors

ME2 inhibitors also include one or more anti-ME2 antibodies. Exemplary antibodies include HPA008247 (Ab2, anti-ME antibody produced in rabbit, where the immunogen is the NAD-dependent malic enzyme, mitochondrial precursor recombinant protein epitope signature tag DGRVFT-PGQGNNVYIFPGVALAVILCNTRHISDSVFLEAAKA-LTSQLTDEELA QGRLYPPLANIQEVSINIAIKVTEYLYANKMAFRY-PEPEDKAKYVKERTWRSE YDSLLPDVYEWPE-SASSPPV (SEQ ID NO:37)) and HPA008880 (anti-ME antibody produced in rabbit, where the immunogen is the NAD-dependent malic enzyme, mitochondrial precursor recombinant protein epitope signature tag KVISKPISEH-KILFLGAGEAALGIANLIVMSMVENGLSEQEAQKKI-WMFDKYG LLVKGRKAKIDSYQEPFTHSAPESIP-DTFEDAVNILKPSTIIGVAGAGRLFTPDV IRAMASINERPVIFALSNPTA (SEQ ID NO:38)). RNAi agents also include commercially available antibodies, such as those available from Abcam (Cambridge, Mass.), Atlas Antibodies AB (Stockholm, Sweden), Novus Biologicals (Littleton, Colo.), LifeSpan Biosciences (Seattle, Wash.), and Santa Cruz Biotechnology (Santa Cruz, Calif.).

ME2 inhibitors include agents that inhibiting one or more proteins upstream of ME2 in the PI3/AKT pathway, such as a PI3K inhibitor, an RTK inhibitor (e.g., an EGFR inhibitor, an Her2 inhibitor, a PDGFR inhibitor, or an IGFR inhibitor), a PDK1 inhibitor, an AKT inhibitor, an mTOR inhibitor (e.g., an mTOR1 inhibitor or an mTOR2 inhibitor), and dual inhibitors of any of these proteins (e.g., a dual PI3K/mTOR inhibitor or a dual AKT/PDK1 inhibitor). Exemplary ME2 inhibitors further include PI3K inhibitors, such as wortmannin, demethoxyviridin, LY294002 (2-morpholin-4-yl-8-phenylchromen-4-one), quercetin, myricetin, staurosporine, GDC-0941 (4-[2-(1H-indazol-4-yl)-6-[(4-methylsulfonylpiperazin-1-yl)methyl]thieno[3,2-d]pyrimidin-4-yl]morpholine), NVP-BEZ235 (2-methyl-2-[4-(3-methyl-2-oxo-8-quinolin-3-ylimidazo[4,5-c]quinolin-1-yl)phenyl] propanenitrile), ZSTK474 (4-[4-[2-(difluoromethyl)benzimidazol-1-yl]-6-morpholin-4-yl-1,3,5-triazin-2-yl] morpholine), PX-866 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10, 11-hexahydroindeno[4,5-h]isochromen-10-yl]acetate), and XL-147 (N-[3-(2,1,3-benzothiadiazol-4-ylamino)quinoxalin-2-yl]-4-methylbenzenesulfonamide); RTK inhibitors, such as erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab; non-specific PDK1 inhibitors, such as OSU-03012 (2-amino-N-[4-[5-phenanthren-2-yl-3-(trifluoromethyl)pyrazol-1-yl]phenyl]acetamide) and celecoxib; AKT inhibitors, such as A-443654 ((2S)-1-(1H-indol-3-yl)-3-[5-(3-methyl-2H-indazol-5-yl) pyridin-3-yl]oxypropan-2-amine), GSK690693 (4-[2-(4-amino-1,2,5-oxadiazol-3-yl)-1-ethyl-7-[[(3S)-piperidin-3-yl]methoxy]imidazo[4,5-c]pyridin-4-yl]-2-methylbut-3-yn-2-ol), VQD-002 (triciribine), and perifosine; dual AKT/PDK1 inhibitors, such as 6H-indeno[1,2-e]tetrazolo[1,5-b] [1,2,4]triazin-6-one, 10H-indeno[2,1-e]tetrazolo[1,5-b][1,2, 4]triazin-10-one, and PHT-427 (4-dodecyl-N-(1,3,4-thiadiazol-2-yl)benzenesulfonamide); mTOR inhibitors, such as rapamycin (sirolimus) and modified rapamycins (rapalogs), such as CCI-779 (temsirolimus), and RAD001 (everolimus)); and dual PI3K/mTOR inhibitors, such as NVP-BEZ235 (2-methyl-2-[4-(3-methyl-2-oxo-8-quinolin-3-ylimidazo[4,5-c]quinolin-1-yl)phenyl]propanenitrile) and PI-103 (3-[4-(4-morpholinyl)pyrido[3',2': 4,5]furo[3,2-d]pyrimidin-2-yl]-phenol).

Diseases

The methods and compositions of the invention include administration of one or more ME2 inhibitors (e.g., RNAi agents) to subject having a disease or at risk of developing a disease (e.g., an increased risk of at least 10%, 20%, 30%, 40%, 50%, 60%, 70%, 80%, 90%, or 100%) associated with increased activity of ME2 (e.g., an increased activity of ME2 of at least 2-fold, e.g., from about 2-fold to about 150-fold, e.g., from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample).

ME2 could be a useful target to treat diseases in various types of tissues. Increased expression of ME2 protein is observed in different types of tumor tissues, including bladder, breast, esophagus, liver, lung, ovary, prostate, and skin ME2 is also expressed in other tissues, including the brain (in neurons) and in the heart (in myocytes). Accordingly, ME2 inhibitors can be used to treat diseases (e.g., cancer) in any of these tissues.

Any useful methods can be used to determine one or more diseases having an increased activity of ME2. For example, the expression of ME2 can be determined in a sample obtained from a subject having a disease (e.g., by using western blotting, DNA expression is often detected by Southern blotting or polymerase chain reaction (PCR), and RNA expression is often detected by northern blotting, PCR, or RNAse protection assays), and an increase in ME2 activity, as described herein, indicates a disease that can be treated with an ME2 inhibitor. Additional methods described herein for diagnostic methods can be used to determine diseases having an increased activity of ME2.

In particular embodiments, the disease is cancer. Exemplary cancers include non-solid cancers and solid cancers, such as leukemia (e.g., chronic myeloid leukemia, acute myeloid leukemia, acute lymphoblastic leukemia, and chronic lymphocytic leukemia), brain cancer (e.g., ependymoma, glioma, medulloblastoma, meningioma, teratoid rhabdoid tumor, and teratoma), bladder cancer (e.g., adenocarcinoma, sarcoma, small cell carcinoma, squamous cell carcinoma, and transitional cell carcinoma), breast cancer (e.g., breast ductal carcinoma), cervical cancer, colorectal cancer, endometrial cancer, esophageal cancer (e.g., adenocarcinoma and squamous cell carcinoma), head and neck cancer, liver cancer (e.g., hepatocellular carcinoma, cholangiocarcinoma, and hemangioendothelioma), lung cancer (e.g., non-small cell lung cancer, small-cell lung cancer, carcinoid, sarcoma, squamous cell cancer, adenocarcinoma, and large cell carcinoma), lymphoma (e.g., malignant lymphoma), ovarian cancer (e.g., ovarian epithelial carcinoma and teratoma), pancreatic cancer, prostate cancer (e.g., adenocarcinoma and prostatic intraepithelial neoplasia), renal cancer, skin cancer (e.g., basal cell carcinoma, squamous cell carcinoma, and malignant melanoma), stomach cancer, testis cancer, thyroid cancer, and urothelial cancer.

The methods and compositions described herein can also be used to treat cancers having one or more particular mutations that confer resistance to first-line anticancer agents. Exemplary cancers having mutations include non-small cell lung cancer having a T790M or a L747S mutation in EGFR kinase, a somatic activating mutation in the tyrosine-kinase pocket of EGFR (e.g., a deletion in exon 19 or a substitution in exon 21, e.g., L858R), or a mutation present in tyrosine kinase inhibitor-resistant cell line H1975; and brain cancer, breast cancer, colorectal cancer, lung cancer, and stomach cancer having a E542K, E545K, H1047R, P539R, or H1047L mutation in the PIK3CA gene (encoding a p110α of class IA of PI3K) (e.g., lung cancer having a H1047R mutation in PIK3CA).

Combination Therapy

The methods and compositions include combinations of an ME2 inhibitor and a therapeutic agent, such as an anticancer agent. Exemplary anticancer agents include chemotherapeutic agents (e.g., arsenic trioxide, cisplatin, carboplatin, chlorambucil, melphalan, nedaplatin, oxaliplatin, triplatin tetranitrate, satraplatin, imatinib, nilotinib, dasatinib, and radicicol), immunomodulatory agents (e.g., methotrexate, leflunomide, cyclophosphamide, cyclosporine A, minocycline, azathioprine, antibiotics (e.g., tacrolimus), methylprednisolone, corticosteroids, steroids, mycophenolate mofetil, rapamycin, mizoribine, deoxyspergualin, brequinar, T cell receptor modulators, and cytokine receptor modulators), antiangiogenic agents (e.g., bevacizumab, suramin, and etrathiomolybdate), mitotic inhibitors (e.g., paclitaxel, vinorelbine, docetaxel, abazitaxel, ixabepilone, larotaxel, ortataxel, tesetaxel, vinblastine, vincristine, vinflunine, and vindesine), nucleoside analogs (e.g., gemcitabine, azacitidine, capecitabine, carmofur, cladribine, clofarabine, cytarabine, decitabine, floxuridine, fludarabine, fluorouracil, mercaptopurine, pentostatin, tegafur, and thioguanine), DNA intercalating agents (e.g., doxorubicin, actinomycin, bleomycin, mitomycin, and plicamycin), topoisomerase inhibitors (e.g., irinotecan, aclarubicin, amrubicin, belotecan, camptothecin, daunorubicin, epirubicin, etoposide, idarubicin, mitoxantrone, pirarubicin, pixantrone, rubitecan, teniposide, topotecan, valrubicin, and zorubicin), folate antimetabolites (e.g., pemetrexed, aminopterin, methotrexate, pralatrexate, and raltitrexed), and other targeting agents (e.g., agents that target particular enzymes or proteins involved in cancer or agents that target particular organs or types of cancers), and combinations thereof.

In particular embodiments, the combination include two or more ME2 inhibitors. Exemplary combinations of ME2 inhibitors include the combination of an RNAi agent (e.g., any described herein, such as an RNAi agent including one of SEQ ID NOs: 1-36) and another ME2 inhibitor, such as an RNAi agent and a PI3K inhibitor (e.g., wortmannin, demethoxyviridin, LY294002, quercetin, myricetin, staurosporine, GDC-0941, NVP-BEZ235, ZSTK474, PX-866, and XL-147, e.g., wortmannin, e.g., LY294002); an RNAi agent and an RTK inhibitor (e.g., erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab, e.g., erlotinib, e.g., gefitinib); an RNAi agent and a non-specific PDK1 inhibitor, such as any described herein; an RNAi agent and an AKT inhibitor, such as any described herein; an RNAi agent and a dual AKT/PDK1 inhibitor, such as any described herein; an RNAi agent and an mTOR inhibitor, such as any described herein; and an RNAi agent and a dual PI3K/mTOR inhibitor, such as any described herein.

Another exemplary combination includes an anti-ME2 antibody (e.g., HPA008247 and HPA008880) and another ME2 inhibitor, such as the combination of an anti-ME2 antibody and an RNAi agent (e.g., any described herein, such as an RNAi agent including one of SEQ ID NOs: 1-36); an anti-ME2 antibody and a PI3K inhibitor (e.g., wortmannin, demethoxyviridin, LY294002, quercetin, myricetin, staurosporine, GDC-0941, NVP-BEZ235, ZSTK474, PX-866, and XL-147, e.g., wortmannin, e.g., LY294002); an anti-ME2 antibody and an RTK inhibitor (e.g., erlotinib, gefitinib, vandetanib, afatinib, axitinib, cediranib, cetuximab, lapatinib, lestaurtinib, neratinib, panitumumab, pazopanib, regorafenib, semaxanib, sorafenib, sunitinib, toceranib, and trastuzumab, e.g., erlotinib, e.g., gefitinib); an anti-ME2 antibody and a non-specific PDK1 inhibitor, such as any described herein; an anti-ME2 antibody and an AKT inhibitor, such as any described herein; an anti-ME2 antibody and a dual AKT/PDK1 inhibitor, such as any described herein; an anti-ME2 antibody and an mTOR inhibitor; and an anti-ME2 antibody and a dual PI3K/mTOR inhibitor.

Administration and Dosage

The present invention also relates to pharmaceutical compositions that contain one or more ME2 inhibitors or a combination of an ME2 inhibitor and a therapeutic agent (e.g., a combination of an ME2 inhibitor and an anticancer agent). The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer, *Science* 249: 1527-1533, 1990.

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a patient with a clinically determined predisposition or increased susceptibility to development of a tumor or cancer. Compositions of the invention can be administered to the patient (e.g., a human) in an amount sufficient to delay, reduce, or preferably prevent the onset of clinical disease or tumorigenesis. In therapeutic applications, compositions are administered to a patient (e.g., a human) already suffering from a cancer in an amount sufficient to cure or at least partially arrest the symptoms of the condition and its complications. An amount adequate to accomplish this purpose is defined as a "therapeutically effective dose," an amount of a compound sufficient to substantially improve some symptom associated with a disease or a medical condition. For example, in the treatment of cancer, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the patient, but generally range from about 0.5 mg to about 3000 mg of the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g. a mammal, such as a human) in an effective amount, which is an amount that produces a desirable result in a treated subject (e.g. the slowing or remission of a cancer or neurodegenerative disorder). Such therapeutically effective amounts can be determined empirically by those of skill in the art.

The patient may also receive an agent in the range of about 0.1 to 3,000 mg per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) mg dose per week. A patient may also receive an agent of the composition in the range of 0.1 to 3,000 mg per dose once every two or three weeks.

Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The compounds and formulations of the present invention may be used in combination with either conventional methods of treatment or therapy or may be used separately from conventional methods of treatment or therapy. When the compounds and formulations of this invention are administered in combination therapies with other agents, they may be administered sequentially or concurrently to an individual. Alternatively, pharmaceutical compositions according to the present invention include a combination of a compound or formulation of the present invention in association with a pharmaceutically acceptable excipient, as described herein, and another therapeutic or prophylactic agent known in the art.

The formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Diagnostic Methods

Increased activity of ME2 can also be used for the diagnosis of a disease, such as cancer (e.g., leukemia or non-small cell lung cancer), or a risk of developing a disease. The ME2 gene or protein can also be used to monitor the therapeutic efficacy of one or more compounds, including compounds and compositions of the invention, used to treat a disease, such as cancer.

Alterations in the expression or biological activity of one or more polypeptides of the invention in a test sample as compared to a normal reference can be used to diagnose any of a disease associated with increased activity of ME2, e.g., cancer.

A subject having a disease associated with increased activity of ME2, e.g., cancer, or a propensity to develop such as disease, will show an alteration (e.g., an increase or a decrease of 10%, 20%, 30%, 40%, 50%, 60%, 70%, 80%, 90%, or more) in the expression or biological activity of one or more activated or down-regulated analytes (e.g., ME2, AKT1/2, AKT1, AKT2, ERK1/2, ERK1, GATA-1, PI3K, PDK1, mTOR1/2, mTOR2, EGFR, Her2, PDGFR, IGFR, vimentin, NADH, NADPH, $NAD^+/NADH$ ratio, $NADP^+/NADPH$ ratio, ROS, ATP, inosine, uridine, or orotate, including phosphorylation status of any kinase described herein) or in a cellular parameter (e.g., apoptosis, proliferation, and pyrimidine metabolism).

In one example, an increase in ME2 gene or protein expression or ME2 enzymatic activity, as compared to a normal reference sample or control, is indicative of cancer, e.g., leukemia or lung cancer, or a risk of developing the same. ME2 can include the full-length polypeptide, degradation products, alternatively spliced isoforms of the polypeptide, enzymatic cleavage products of the polypeptide, the polypeptide bound to a substrate or ligand, or free (unbound) forms of the polypeptide.

In another example, an increase in ME2 gene or protein expression or ME2 enzymatic activity is determined indirectly, such as by measuring one or more of increased NADH or NADPH formation, decreased $NAD^+/NADH$ ratio, decreased $NADP^+/NADPH$ ratio, decreased ROS activity, increased ATP levels, activation of phospho-ERK1/2, deactivation of phospho-AKT, decreased GATA-1 expression, increased vimentin expression, decreased apoptosis, increased proliferation, increased pyrimidine metabolism, increased inosine levels, increased uridine levels, and decreased orotate levels, as compared to a control or a normal reference sample.

Standard methods may be used to measure analyte levels or cellular parameters in any bodily fluid, including, but not limited to, urine, blood, serum, plasma, saliva, or cerebrospinal fluid. Such methods include immunoassay, ELISA, Western blotting using antibodies directed ME2 or any proteins upstream or downstream of ME2 in the PI3K/AKT pathway (e.g., including but not limited to AKT1/2, AKT1, AKT2, ERK1/2, ERK1, GATA-1, PI3K, PDK1, mTOR1/2, mTOR2, EGFR, Her2, PDGFR, and IGFR), and quantitative enzyme immunoassay techniques. ELISA assays are the preferred method for measuring polypeptide levels. Accordingly, the measurement of antibodies specific to ME2 or any proteins upstream or downstream of ME2 in the PI3K/AKT pathway in a subject may also be used for the diagnosis of cancer, e.g., leukemia or lung cancer, or a risk of developing the same.

In one embodiment, a subject having cancer, e.g., leukemia or lung cancer, or a risk of developing the same, will show an increase in the expression of a nucleic acid encoding ME2 or any proteins upstream or downstream of ME2 in the PI3K/AKT pathway (e.g., including but not limited to AKT1/2, AKT1, AKT2, ERK1/2, ERK1, GATA-1, PI3K, PDK1, mTOR1/2, mTOR2, EGFR, Her2, PDGFR, and IGFR). Methods for detecting such alterations are standard in the art and are described in Sandri et al. (Cell 117:399-412 (2004)). In one example Northern blotting or real-time PCR is used to detect mRNA levels (Sandri et al., supra, and Bdolah et al., *Am. J. Physio. Regul. Integr. Comp. Physiol.* 292:R971-R976 (2007)).

In another embodiment, hybridization at high stringency with PCR probes that are capable of detecting a ME2 or any proteins upstream or downstream of ME2 in the PI3K/AKT pathway (e.g., including but not limited to AKT1/2, AKT1, AKT2, ERK1/2, ERK1, GATA-1, PI3K, PDK1, mTOR1/2, mTOR2, EGFR, Her2, PDGFR, and IGFR), including genomic sequences, or closely related molecules, may be used to hybridize to a nucleic acid sequence derived from a subject having disease associated with increased activity of ME2, e.g., cancer. The specificity of the probe, whether it is made from a highly specific region, e.g., the 5'-regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations in a nucleic acid molecule, or may be used to monitor expression levels of a gene encoding a polypeptide of the invention.

Diagnostic methods can include measurement of absolute levels of a polypeptide, nucleic acid, or antibody of interest. In any of the diagnostic methods, the level of a polypeptide, nucleic acid, or antibody, or any combination thereof, can be measured at least two different times from the same subject and an alteration in the levels (e.g., by 10%, 20%, 30%, 40%, 50%, 60%, 70%, 80%, 90%, or more) over time is used as an indicator of a disease associated with increased activity of ME2, e.g., cancer, or the propensity to develop the same. It will be understood by the skilled artisan that for diagnostic methods that include comparing of the polypeptide, nucleic acid, or antibody level to a reference level, particularly a prior sample taken from the same subject, a change over time with respect to the baseline level can be used as a diagnostic indicator of a cancer, or a predisposition to develop the same. The diagnostic methods described herein can be used individually or in combination with any other diagnostic method described herein for a more accurate diagnosis of the presence of, severity of, or predisposition to a disease associated with increased activity of ME2, e.g., cancer, or a predisposition to the same.

Screening Assays to Identify One or More ME2 Inhibitors

As discussed above, we have discovered that increased activity of ME2 is correlated with cancer. Based on these discoveries, ME2 and proteins upstream or downstream of ME2 in the PI3K/AKT pathway (e.g., including but not limited to AKT1/2, AKT1, AKT2, ERK1/2, ERK1, GATA-1, PI3K, PDK1, mTOR1/2, mTOR2, EGFR, Her2, PDGFR, and IGFR), as well as other analytes or cellular parameters related to increased activity of ME2 (e.g., NADH, NADPH, $NAD^+$/NADH ratio, $NADP^+$/NADPH ratio, ROS, ATP, vimentin, apoptosis, proliferation, pyrimidine metabolism, inosine, uridine, or orotate) are useful for the high-throughput low-cost screening of candidate compounds to identify those that modulate, alter, or decrease (e.g., by at least 10%, 20%, 30%, 40%, 50%, 60%, 70%, 80%, 90%, 95%, or more) the expression or biological activity of ME2. Compounds that decrease the expression or biological activity of ME2 or proteins upstream of ME2 (e.g., AKT1/2, AKT1, AKT2, PI3K, PDK1, mTOR2, EGFR, Her2, PDGFR, and IGFR) can be used for the treatment or prevention of a disease associated with increased activity of ME2, e.g., cancer, or a propensity to develop such as disease.

In particular examples, candidate compounds having one or more of the following properties are considered ME2 inhibitors: decreased NADH formation (e.g., from 3-fold to 4-fold decreased formation), decreased NADPH formation (e.g., from 5-fold to 10-fold, e.g., about 7 fold, decreased formation), increased $NAD^+$/NADH ratio (e.g., from 1.5-fold to 3-fold, e.g., about 2-fold, increased ratio), increased $NADP^+$/NADPH ratio (e.g., from 5-fold to 15-fold, e.g., about 9-fold, increased ratio), increased ROS activity, decreased ATP levels (e.g., from 2-fold to 4-fold, e.g., about 3-fold, decreased levels), inactivation of phospho-ERK1/2, activation of phospho-AKT, increased GATA-1 expression, decreased vimentin expression, increased apoptosis, decreased cellular proliferation, decreased pyrimidine metabolism, decreased inosine levels (e.g., from 5-fold to 10-fold, e.g., about 6-fold, decreased levels), decreased uridine levels (e.g., from 5-fold to 10-fold, e.g., about 6-fold, decreased levels), or increased orotate levels (e.g., from 50-fold to 150-fold, e.g., 75-fold to 150-fold, e.g., about 90-fold, increased levels), as compared to a control or a normal reference sample (e.g., a sample from a subject that has been treated for a disease associated with increased activity of ME2, e.g., cancer; or a sample of purified ME2 at a known normal concentration). Candidate compounds can be tested for their effect on ME2 activity using assays known in the art or described in the Examples below.

In general, candidate compounds are identified from large libraries of both natural product or synthetic (or semi-synthetic) extracts, chemical libraries, or from polypeptide or nucleic acid libraries, according to methods known in the art. Those skilled in the field of drug discovery and development will understand that the precise source of test extracts or compounds is not critical to the screening procedure(s) of the invention.

EXAMPLES

Example 1

Induction of Erythroid Differentiation in Human Erythroleukemia Cells by Depletion of Malic Enzyme 2

Summary: Malic enzyme 2 (ME2) is a mitochondrial enzyme that catalyzes the conversion of malate to pyruvate and $CO_2$ and uses NAD as a cofactor. Higher expression of this enzyme correlates with the degree of cell de-differentiation. We found that ME2 is expressed in K562 erythroleukemia cells, in which a number of agents have been found to induce differentiation either along the erythroid or the myeloid lineage. We found that knockdown of ME2 led to diminished proliferation of tumor cells and increased apoptosis in vitro. These findings were accompanied by differentiation of K562 cells along the erythroid lineage, as confirmed by staining for glycophorin A and hemoglobin production. ME2 knockdown also totally abolished growth of K562 cells in nude mice. Increased ROS levels, likely reflecting increased mitochondrial production, and a decreased $NADPH/NADP^+$ ratio were noted, but use of a free radical scavenger to decrease inhibition of ROS levels did not reverse the differentiation or apoptotic phenotype, suggesting that ROS production is not causally involved in the resultant phenotype. As might be expected, depletion of ME2 induced an increase in the $NAD^+$/NADH ratio and ATP levels fell significantly. Neither exogenous malate supplementation nor inhibition of the malate-aspartate shuttle was sufficient to induce K562 differentiation.

We also examined several intracellular signaling pathways and expression of transcription factors and intermediate filament proteins whose expression is known to be modulated during erythroid differentiation in K562 cells. We found that silencing of ME2 leads to phospho-ERK1/2 inhibition, phospho-AKT activation, increased GATA-1 expression, and diminished vimentin expression. Metabolomic analysis, conducted to gain insight into intermediary metabolic pathways that ME2 knockdown might affect, showed that ME2 depletion resulted in high orotate levels, suggesting potential impairment of pyrimidine metabolism. Collectively, our data in this Example point to ME2 as a potentially novel metabolic target for leukemia therapy.

Introduction: Malic enzymes (ME; EC 1.1.1.40) represent a family of oxidative decarboxylases that catalyze the divalent metal ion ($Mn^{2+}$ or $Mg^{2+}$) dependent irreversible oxidative decarboxylation of L-malate to yield $CO_2$ and pyruvate, with concomitant reduction of dinucleotide cofactor $NAD^+$ or $NADP^+$. In different species, these enzymes show highly conserved sequences and similar overall structural topology, suggesting important biological functions, which however are not well-defined. Three isoforms of malic enzyme have been identified in mammals according to their nucleotide specificity: cytosolic $NADP^+$-dependent (ME1), mitochondrial $NAD^+$-dependent (ME2), and mitochondrial $NAD(P)^+$-dependent malic enzyme (ME3). It has been shown that ME2 favors NAD as a cofactor under physiological conditions, although it can use both NAD and $NADP^+$. ME2 is thought to be involved in the ultimate conversion of malate to citrate, the latter being directed to the cytosol via the carboxylate carrier. Citrate that is extruded from mitochondria is the primary precursor for the endogenous synthesis of fatty acids, cholesterol, isoprenoid, as well as acetylation reactions that modify proteins.

There is a paucity of information on the role of malic enzymes in normal physiology and in disease states. It is important to recognize that the literature is confusing in that sometimes the malic enzyme is not specified (i.e., ME1 versus ME2 versus ME3) and, in some cases, the enzyme is confused with two of the malate dehydrogenases. Thus, we cite here only references that provide the EC number for ME2 or that clearly specify the activity in question as being due to a mitochondrial $NAD^+$ dependent enzyme that produces pyruvate from malate.

Previous studies indicate that both the cytosolic and mitochondrial malic enzyme are involved in malate-pyruvate cycling under conditions of nutrient-stimulated insulin secretion. In neurons, pyruvate produced from malate is a substrate for the neuronal synthesis of γ-aminobutyric acid and is found to be associated to idiopathic generalized epilepsy through linkage analysis. ME2 gene expression is 5.6-fold lower in anterior cingulate tissue from post-mortem bipolar brains and is associated with both psychotic and manic disorders including schizophrenia and bipolar disorders. From a cancer standpoint, ME2 activity increases with progression to neoplasia in a rat tracheal epithelial line with similar findings in Morris hepatomas. Of interest, ME2 is present in tumor mitochondria in levels proportional to the rate of cell division, while curiously it is essentially absent in liver, regenerating liver, and the mitochondria of other organs. ME2 interacts directly with the malate-aspartate shuttle system. It is believed that ME2, via the generation of NADH and pyruvate products, may play an important role in the metabolism of glutamine, which is needed to produce both reducing equivalents and energy in rapidly proliferating tissues such as tumors. ME2 is regulated by ATP which acts as an inhibitor and by fumarate which acts as an activator of its catalytic activity. This regulation is consistent with the functional role of this enzyme, as ATP is an overall product of energy metabolism and fumarate is generated by the previous step in the TCA cycle. The possible functional involvement of ME2 in neoplasia is strongly suggested by its increased activity in tumor tissue. This finding implicates the enzyme as a potentially attractive novel anticancer target and warrants detailed investigation of its functional role in cancer.

The human K562 erythroleukemia cell line is a multipotent hematopoietic precursor cell line derived from a patient with chronic myeloid leukemia (CML) in blast crisis and thus provides a model system to study gene expression during hematopoiesis. These cells can be induced to differentiate along either the erythroid or megakaryocytic lineages. A variety of chemical compounds, such as hemin, butyrate, cisplatin, PMA, TPA, Ara-C, the BCR-ABL signaling inhibitor imatinib, and the Hsp90 inhibitor radicicol have been found to induce K562 differentiation. Here, we have used the K562 model system to study the function of ME2 and find that silencing this gene leads to K562 cell apoptosis and erythroid differentiation and abolishes growth of these cells in vivo.

Materials and Methods

Materials: Dichlorodihydrofluorescein diacetate (CM-$H_2$DCF-DA), MitoSOX™, and nonyl acridine orange (NAO) were purchased from Invitrogen/Molecular Probes (Carlsbad, Calif.). Lipofectamine 2000 and tissue culture reagents were purchased from Invitrogen. The pLKO constructs containing short hairpins RNAi (shRNA) targeted to ME2 and ATP citrate lyase (ACL), and its control vector were purchased from OPEN Biosystems. All restriction enzymes were obtained from New England Biolabs. The QIAprep kit was from QIAGEN. Fetal bovine serum (FBS) was obtained from GIBCO. Puromycin, anti-ME2 polyclonal antibody and anti-β-tubulin monoclonal antibody were purchased from Sigma. The anti-vimentin monoclonal antibody was from Santa Cruz Biotechnology. The anti-GATA-1, phospho-ERK1/2, phospho-AKT308, phospho-AKT473 and AKT1/2 polyclonal antibodies were purchased from Cell Signaling Technology. The ERK1/2 monoclonal antibody was from Zymed. The CD235a-FITC and CD10-FITC monoclonal antibodies were obtained from DAKO. Secondary antibodies for enhanced chemiluminescence (ECL) detection were from Amersham Biosciences. All other reagents were of standard analytical grade.

Cell Culture: The human erythroleukemia K562 cell line was obtained from American Type Culture Collection and grown in Iscove's Modified Medium. All media were supplemented with 10% (v/v) fetal calf serum, 100 units penicillin and 100 μg/ml streptomycin, and grown at 37° C. and 5% $CO_2$. Cells infected with shRNA virus were selected with 1.0 μg/ml puromycin and stable knock-down of ME2 or ACL were used for analysis.

Generation of ME2 deficiency cell lines: K562 cells were transduced separately with empty shRNA vector control and three different ME2 and one ACL shRNA lentiviral particles, as previously described in Root et al., *Nat. Methods* 3: 715-719 (2006). ATP citrate lyase (ACL) shRNA lentiviral knockdown cells were used as positive controls. The three ME2 shRNA sequence (sense) used in this study are: shME2-1,5'-CGGCATATTAGTGACAGTGTT-3' (SEQ ID NO:1); shME2-2, 5'-CCCAGTATGGACACATCTTT A-3' (SEQ ID NO:2); and shME2-3,5'-GCACGGCT-GAAGAAGCATATA-3' (SEQ ID NO:3). The shACL sequence is: 5'-GCCTCTTCAATTTCTACGAGGACTT-3' (SEQ ID NO:39). To produce recombinant lentiviral particles, subconfluent 293FT cells were cotransfected with 3 μg of a shRNA plasmid, and 9 μg virapower packaging mix (Invitrogen) using Lipofectamine 2000 (Invitrogen). After 16 hours, culture medium was switched to regular growth medium and cells were allowed to incubate for additional 48 hours. Conditioned cell culture media containing recombinant lentiviral particles were harvested and frozen. K562 cells were transduced with above cell culture supernatant containing lentiviral particles for 24 hours. These cells were then selected in puromycin (Sigma Aldrich) to generate stable cell lines encoding empty vector shRNA, ME2 shRNA, or ACL shRNA. Hereafter, we named those pools pLKO, shME2-1, shME2-2, shME2-3, and shACL, respectively. In order to generate single ME2 knockdown clone, cells from the stable knockdown pools were serially diluted in 96-well plates. The single clone corresponding to its parental pools were named pLKO-s, shME2-1s, shME2-2s, and shME2-3s, respectively.

Western Blotting: K562 cells with and without ME2 knockdown treated with 10 μM LY294002 or DMSO were lysed with RIPA buffer (50 mM Tris-HCl, pH 7.4, 150 mM NaCl, 1% NP-40, 0.1% SDS and 0.5% sodium deoxycholate), and equal amount of proteins were resolved by 4%-12% Bis-Tris gels (Invitrogen), as previously described in Ren et al., *Proc. Natl. Acad. Sci. USA* 104: 10465-10469 (2007). Briefly, the proteins were transferred to a PVDF membrane, and membranes were blocked with BLOTTO (5% nonfat dry milk and 0.1% Tween 20 in PBS), and incubated with antisera generated against ME2, phospho-AKT380, phosphor-473, AKT1/2, phosphor-ERK1/2, ERK1, vimentin, GATA-1 or β-tubulin antibodies respectively. Membranes were washed in PBS plus 0.1% Tween 20 and probed with anti-rabbit or anti-mouse HRP-conjugated secondary antibody (both at 1:10,000 dilution), and proteins were detected using the ECL Plus chemiluminescence detection reagent (Amersham Biosciences).

Proliferation assay: Control and ME2 deficient cell lines were plated in 6-well plate at a density of $1×10^5$ cells/well and maintained at 37° C. in a 5% $CO_2$ incubator. After 24, 72, 120 and 168 hours of initial plating, 0.5 ml cells were diluted into 10 ml of Hanks' buffer and counted by Coulter counter. All samples were assayed in triplicate to generate proliferation curves, as described in Benson et al., *Nature* 441: 451-456 (2006).

Erythroid differentiation assay: Induction of surface expression of the erythroid marker glycophorin A and CD10 was determined by indirect immunofluorescence and flow cytometry, as described previously by Hatzivassiliou et al., in *Cancer Cell.* 8: 311-321 (2005). In brief, K562 cells with or without ME2 knockdown were stained with a mouse FITC-conjugated anti-glycophorin A or CD10 antibody (Dako) at 1:100 dilution in medium plus 10% FCS for 30 min at 4° C. Control cells were stained with FITC-conjugated IgG. Cells expressing hemoglobin were determined by benzidine staining, as previously described by Park et al., in *Cell Growth Differ.* 12: 481-486 (2001). The benzidine dihydrochloride stock solution contained 0.2% w/v benzidine hydrochloride in 3% acetic acid. Cells ($1\times10^5$) were washed twice in ice-cold PBS. The cell pellets were resuspended in ice-clod PBS. Before staining, 5 µl of 30% $H_2O_2$ was added to 1 ml of a stock solution of benzidine solution. The cell suspensions were mixed with the benzidine solution in a 1:1 ratio and counted in a hemocytometer after 30 min. Blue cells were considered to be positive for hemoglobin. The proportion of blue-stained cells was quantified under light microscopy. A total of 500 cells were counted for each sample in triplicate. Shown is the mean±SD of a representative experiment.

Annexin-V apoptosis assay: Apoptosis was measured by staining with the Nexin reagent using a Nexin kit and counting on the Guava PCA-96 system (Guava Technologies) as per the manufacture's protocol. Briefly, cells were harvested and re-suspended in 100 µl of 1× Nexin buffer, and then mixed with 100 µl of Annexin-V-PE, and Nexin 7-AAD. The cells were allowed to incubate for 20 minutes at room temperature and analyzed in the Guava flow cytometer.

Determination of cellular reactive oxygen species (ROS): Intracellular ROS production was measured by staining with $CM-H_2DCFDA$. $CM-H_2DCFDA$ is a cell-permeant indicator for ROS that is nonfluorescent until removal of the acetate groups by intracellular esterases and oxidation occurs within the cell. The procedure for measuring ROS was carried out as described in Trachootham et al., in *Cancer Cell.* 10: 241-252 (2006), with minor modifications. Briefly, K562 cells transduced with shRNA lentiviral particles or control vector were selected with puromycin for 2 weeks, and then incubated with 5 µM $CM-H_2DCF-DA$ for 3 hours, followed by flow cytometry using a FACSCalibur equipped with CellQuest Pro software. Superoxide radicals ($O_2^-$) were measured separately using the MitoSOX™ reagent according to the manufacturer's protocol (Invitrogen). In brief, cells with or without ME2 knockdown were incubated with 5 µM MitoSOX™ reagent for 10 minutes at 37° C., then washed three times and observed under a fluorescence microscope using the Rhodamine filter and Axiovision software for capturing images (Zeiss, Germany).

Determination of oxidative damage to mitochondrial membranes: Mitochondrial membrane lipid peroxidation was detected as described in Trachootham et al., in *Cancer Cell.* 10: 241-252 (2006). K562 cells transduced with shRNA lentiviral particles or control vector were selected with puromycin for 2 weeks, and then labeled with 50 nM NAO for 20 mM and analyzed by flow cytometry using FL2 or 3 filters and Cell Quest software analysis data (Becton Dickson).

Xenograft model in nude mice: Animal experiments were performed under federal guidelines and approved by the Institutional Animal Care and Use Committee (IACUC) of the Beth Israel Deaconess Medical Center (Approval number 0342007). K562 xenografts in nude mice were generated by following the description of Verrax et al., in *Biochem. Pharmacol.* 72: 671-680 (2006). Briefly, approximately $10^7$ ME2 deficient or control K562 cells resuspended in 200 µl of a serum-free culture medium/Matrigel mixture (1:1) were subcutaneously injected into the right and left flanks of male nude/nu/nu athymic mice, respectively. Tumor-bearing mice were sacrificed after 6-8 weeks and tumor masses were measured or imaged before excision. Tumor lysates were prepared by homogenization of tumor tissues in RIPA lysis buffer and were resolved by SDS-PAGE and transferred onto PDVF membranes and immunoblotted with anti-ME2 antibody and normalized by β-tubulin as a loading control.

Intracellular ATP measurements: Intracellular ATP levels in control and ME2 deficient cells were measured by ATP Bioluminescence Assay Kit CLS II (Roche, Germany), according to manufacturer's instructions. Briefly, cells were diluted to a concentration of $10^7$ cells/ml, then add 9 volumes of boiling lysis buffer (100 mM Tris, 4 mM EDTA, pH 7.75) and incubated for another 2 minutes at 100° C. Cell lysates were collected by centrifugation and pelleting at 1000×g for 1 minute, and 50 µl of samples were transferred into a MTP-well, and mixed with 50 µl luciferase reagent. Luminescence was measured using a luminescence reader (Molecular Devices) and normalized for protein concentration.

$NAD^+$/NADH assay: Intracellular $NAD^+$ and NADH levels in control and ME2 deficient cells were measured by $NAD^+$/NADH Assay Kit (Abcam, San Francisco, Calif.), according to manufacturer's instructions. Briefly, $2\times10^5$ cells were washed with cold PBS and extracted with NADH/NAD Extraction Buffer by freeze/thaw two cycles (20 min on dry-ice, then 10 min at room temperature). Total NADt and NADH were detected following the instruction in a 96-well plate and color were developed and read at 450 nm. The concentration of NADt or NADH was expressed in pmol/$10^6$ cells. NAD/NADH Ratio was calculated as: [NADt−NADH]/NADH.

Metabolite profiling: To determine differences in metabolite profiles between ME2-depleted and control cells, metabolite extracts were prepared and then analyzed using liquid chromatography tandem mass spectrometry (LC-MS). Briefly, K562 cells with or without ME2 depletion were washed once and resuspended in fresh growth medium and grown an additional 2-4 hours. To initiate the extractions, cells were spun down and media were vacuum aspirated. Lipids were extracted with the addition of 4 mL isopropanol (4° C.) and polar metabolites were extracted with the addition of 4 mL 80% methanol (−80° C.). Following the addition of extraction solvent, the samples were vortexed for 1 minute, held for 1 hour (4° C. for lipid extracts; −80° C. for polar metabolite extracts), and then centrifuged at 3500 rpm for 10 minutes. The supernatants were transferred to new tubes. For polar metabolites, the pellet was resuspended in 1 ml 80% methanol (−80° C.), vortexed for another 1 minute, centrifuged as described above, and the supernatants were combined.

LC-MS data were acquired using 4000 QTRAP triple quadrupole mass spectrometers (Applied Biosystems/Sciex, Foster City, Calif.) equipped with HTS PAL autosamplers (Leap Technologies, Carrboro, N.C.) and either Agilent 1100 Series or Agilent 1200 Series binary HPLC pumps (Santa Clara, Calif.). Several chromatographic methods were used to profile endogenous metabolites. Lipids were analyzed using a ProSphere C4 HPLC column (150×3 mm; Grace, Columbia, Md.), and full scan MS data were acquired in the positive ion mode. Biogenic amines and other positively charged polar metabolites were separated using an Atlantis HILIC column (150×2.1 mm; Waters, Milford, Mass.) that was eluted with a 10 min linear gradient, initiated with 100% mobile phase B (acetonitrile with 0.1% formic acid, v/v) and concluding with 60% mobile phase A (10 mM ammonium formate and 0.1% formic acid, v/v). Central metabolites, pyrimidines, and other negatively charged polar compounds were analyzed using the ion paring chromatography method described by Lou et al. in *J. Chromatogr. A.* 1147: 153-164 (2007), with a minor modification to the gradient program. Mobile phases used in the modified method were 10 mM tributylamine/15 mM acetic acid (mobile phase A) and methanol (mobile phase B) and the column was eluted at a flow rate of 200 µL/min using the following program: 100% mobile phase A at initiation, 100% A at 4.5 mM, 80% A at 7.5 mM, 70% mobile phase A at 26.5 mM, 2% mobile phase A at 36.5 mM, and 2% mobile phase A at 40.5 min. Multiple reaction monitoring (MRM) was used to acquire targeted MS data for specific metabolites in the positive (HILIC method) and negative ion (ion paring method) modes. Declustering potentials and collision energies were optimized for each metabolite by infusion of reference standards prior to sample analyses. The scheduled MRM algorithm in the Analyst 1.5 software (AB SCIEX; Foster City, Calif.) was used to automatically set dwell times for each transition. MultiQuant software (Version 1.1; AB SCIEX; Foster City, Calif.) was used for automated peak integration and metabolite peaks were manually reviewed for quality of integration and compared against a known standard to confirm identity.

Results

Knockdown of endogenous ME2 levels by shRNA impairs proliferation of K562 cells: To investigate the effects of ME2 inhibition on K562 cells, we produced recombinant lentiviral particles by expressing constructs containing ME2 short hairpin RNAs (shRNA) and established stable cell clones. Three independent constructs, shME2-1, shME2-2, and shME2-3, were used to generate stable cell lines. Each of these pools displayed significantly reduced ME2 protein levels compared to control lentiviral vector only (pLKO) infected cells (FIG. 1A). These three pools were used in experiments described in the Methods section to examine the role of ME2 in K562 cell proliferation. As shown in FIG. 1B, stable lentiviral reduction of ME2 protein levels resulted in dramatic inhibition of K562 cell growth in vitro. Furthermore, we established three single clones from the three independent pools, designated as shME2-1s, shME2-2s, and shME2-3s. The three single clones also displayed marked reduction in ME2 protein levels (FIG. 1C). As anticipated, cell proliferation was markedly decreased in these cells (FIG. 1D).

Figure 2:
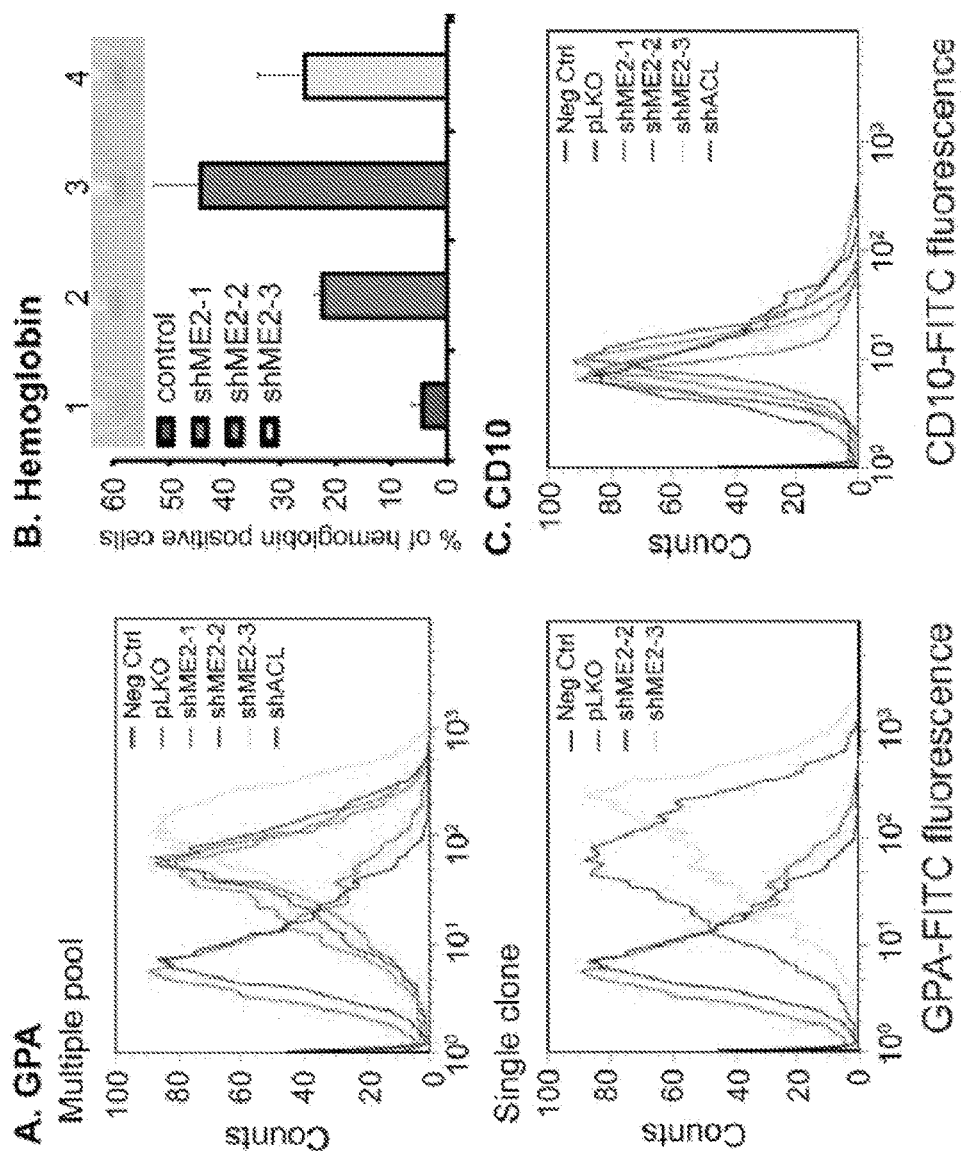
FIG. 2 shows that stable knockdown of endogenous ME2 levels in K562 cells induces erythroid differentiation. A: Expression levels of the erythroid marker glycophorin A (GPA) on the surface of control (pLKO) and ME2 knockdown cells (shME2-1, shME2-2 and shME2-3) were compared using a mouse FITC-conjugated anti-human glycophorin A antibody. As a negative control (Neg Ctrl), cells were incubated with FITC-conjugated control IgG. As a positive control, K562 cells were transduced with ATP citrate lyase (ACL) shRNA lentiviral particles (shACL, where ACL inhibition is known to cause erythroid differentiation in K562 cells), and incubated with mouse FITC-conjugated anti-human glycophorin A antibody. The control clone was generated by stable transduction of control pLKO vector, while clones shME2-1, shME2-2, and shME2-3 were generated using the pLKO-ME2 shRNA lentivirus. Data are representative of three independent experiments. B: The percentage of hemoglobin-expressing cells in control (pLKO, first bar in graph) and ME2 knockdown (shME2-1, shME2-2, and shME2-3, second to fourth bars in graph) cell populations was determined by benzedrine staining. Plotted is the mean±SD from triplicate samples from a representative experiment. Inset: cell pellets from ME2 knockdown cells. 1: pLKO; 2: shME2-1; 3: shME2-2; 4: shME2-3. Increased brown color was clearly visible in lanes 2, 3 and 4. C: Expression levels of the megakaryocytic marker CD10 on the surface of control (pLKO) and ME2 knockdown cells (shME2-1, shME2-2, and shME2-3) were compared using a mouse FITC-conjugated anti-human CD10 antibody. As a negative control (Neg Ctrl), cells were incubated with FITC-conjugated control IgG. The control clone was generated by stable transduction of control pLKO vector, while clones shME2-1, shME2-2, and shME2-3 were generated using the pLKO-ME2 shRNA let virus. Data are representative of three independent experiments.
Figure 9:
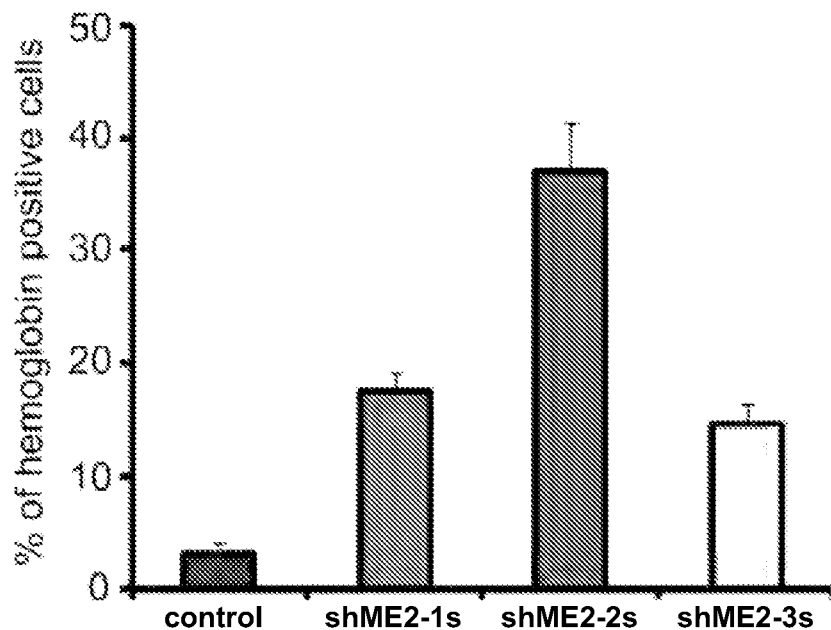
FIG. 9 shows hemoglobin expression in single clonal cell populations. The percentage of hemoglobin-expressing cells in control (pLKO) and ME2 knockdown (shME2-1s, shME2-2s and shME2-3s) single clonal cell populations was determined by benzedrine staining. Plotted is the mean±SD for pLKO (first bar in graph); shME2-1s (second bar in graph); shME2-2s (third bar in graph); and shME2-3s (fourth bar in graph).

Stable knockdown of endogenous ME2 levels by shRNA induces erythroid differentiation in K562 cells: Next, we asked whether ME2 silencing would lead to differentiation of K562 cells. We assayed for erythroid differentiation by analyzing our pooled ME2 knockdown cells for expression of glycophorin A (CD235a), a cell surface glycoprotein expressed selectively on erythroid precursors and mature erythrocytes. Previously it has been shown that glycophorin A is induced in K562 cells undergoing erythroid differentiation in response to imatinib or radicicol. Compared to vector transduced cells, ME2 knockdown cells displayed an increase in the surface expression of this erythroid cell marker (FIG. 2A). Similar results were also obtained in single clones derived from shME2-2 and shME2-3 pools (FIG. 2B). Furthermore, quantitation of hemoglobin-positive cells revealed that approximately 21.2%, 50.32%, and 31.52% of cells within the shME2-1, shME2-2 and shME2-3 ME2 knockdown population, respectively, expressed hemoglobin, compared to 4.4% for vector control infected K562 cells (FIG. 2B and FIG. 9).

K562 cells can also differentiate along the megakaryocytic lineage. We assessed our ME2 knockdown cells for their degree of megakaryocytic differentiation by analyzing the cells for expression of CD10, a cell surface glycoprotein expressed selectively on mature megakaryocytic cells that is induced in K562 cells in response to PMA stimulation. As shown in FIG. 2C, there was no difference in expression CD10 between control and ME2 knockdown cells, suggesting that deficiency of ME2 cells directs K562 cells toward erythroid differentiation.

Figure 3:
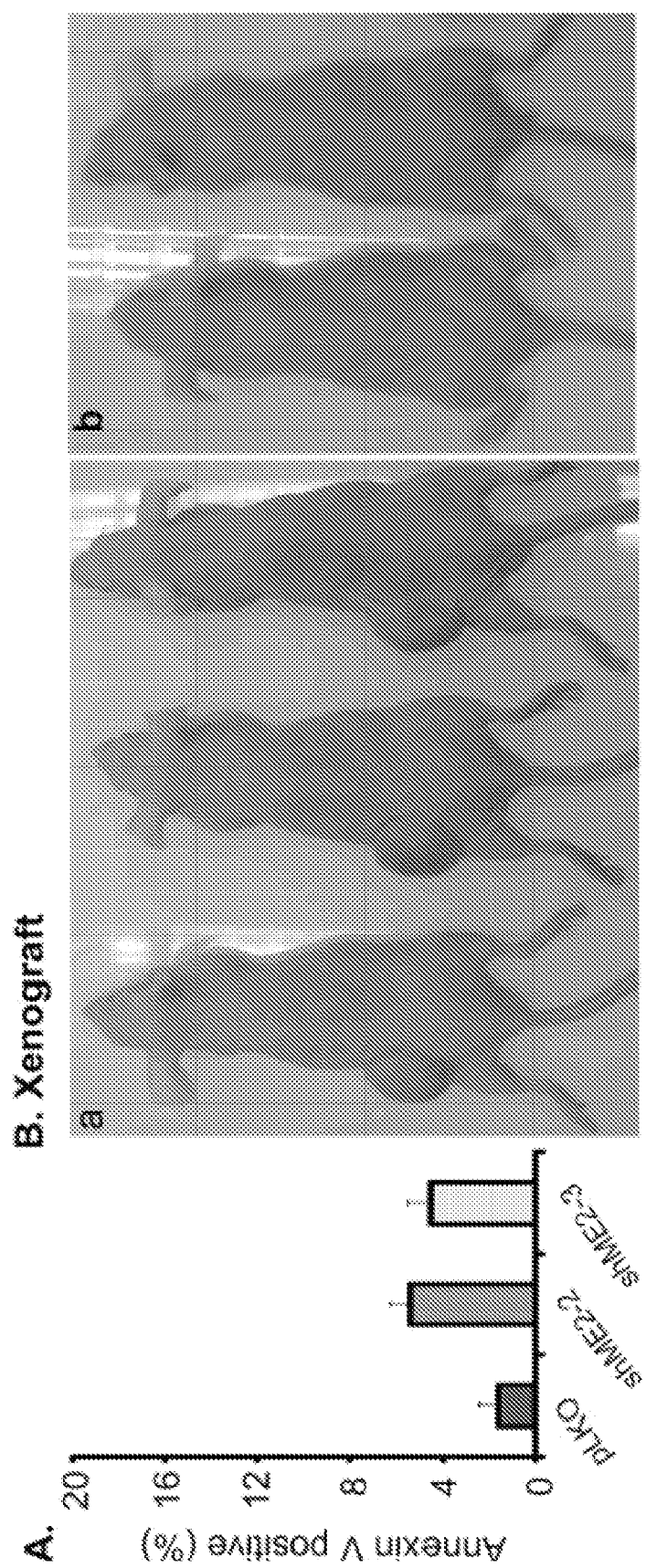
FIG. 3 shows that stable knockdown of endogenous ME2 levels in K562 cells results in apoptosis in vitro and suppresses tumor formation from K562 cells in vivo. A: Knockdown of ME2 induces apoptosis in K562 as detected using the annexin V reagent. Data are expressed as mean±SD, n=3. B: Stable knockdown of ME2 in K562 cells failed to generate tumors in nude mice. Approximately $10^7$ ME2 deficient or control K562 cells resuspended in 200 μl of a serum-free culture medium/Matrigel mixture (1:1) were subcutaneously implanted into female athymic nude mice. Tumor-bearing mice were sacrificed after 4 weeks and the mice were photographed before excision and weighing. a, Left (L): pLKO; Right (R): shME2-2: b, L and R: shME2-3. Tumors formed only in the pLKO transduced cells.

Knockdown of endogenous ME2 leads to apoptosis in K562 cells and suppresses tumor growth in vivo: Tumor cell differentiation is often accompanied by increased apoptosis. Therefore, we examined apoptosis in K562 cells with ME2 depletion by annexin-V/7-AAD staining. As shown in FIG. 3A, knockdown of ME2 levels caused a 2.8 to 3.3-fold increase in basal apoptosis.

Next, we asked what the effects of ME2 depletion would be in vivo by examining tumorigenicity of K562 cells in mice. We injected vector control and ME knockdown clones (shME2-2 and shME2-3) subcutaneously into nude mice and assessed tumor formation and progression following injections. In one group of 4 mice, each mouse received a vector control inoculation in one flank and an ME2 shRNA clone in the other, so that tumor comparisons would be controlled for each individual mouse. In another group of 2 mice, both of the flanks were injected with another ME2 shRNA clone. Growth of tumors was monitored weekly, and tumors were excised and weighed 6 to 8 weeks post-injection. The K562 ME2 knockdown cells failed to form tumors (FIG. 3B).

Depletion of endogenous ME2 levels enhances reactive oxygen species (ROS), increases NAD$^+$/NADH and NADP$^+$/NADPH ratio and inhibits ATP production in K562 cells: The role of ROS in cell differentiation and cell survival is complex. There is some evidence supporting the notion that certain cancer cells are under increased oxidant stress. In particular, increased ROS generation occurs in cancer cells carrying mutations or activation of Ras, Bcr-Abl, and c-Myc. Further increases in ROS can promote differentiation and additional increases can lead to apoptosis. Indeed, anticancer drugs including doxorubicin, arsenic trioxide, and taxol have been observed to generate ROS. Increasing ROS can induce cell differentiation in K562 cells and in neuroblastoma cells.

Figure 4:
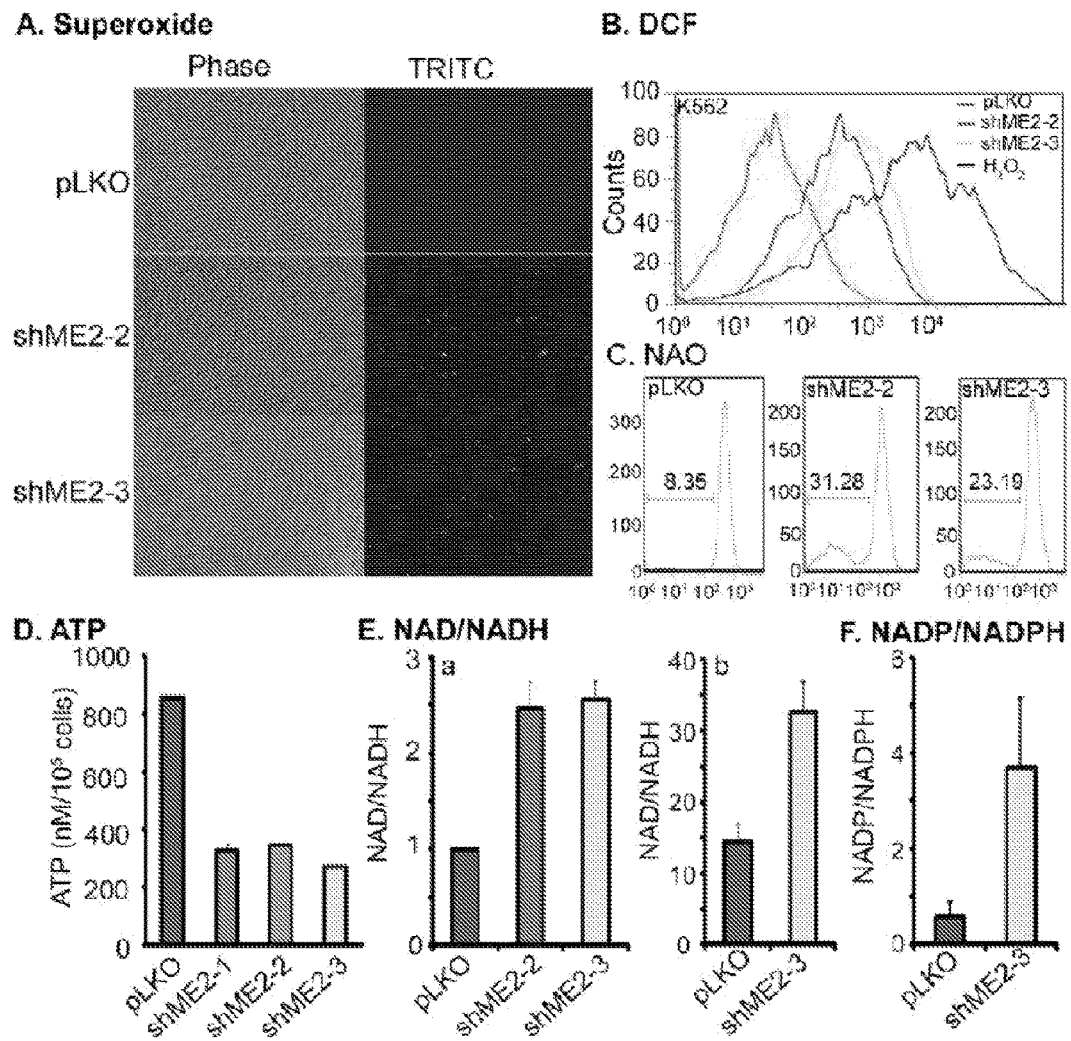
FIG. 4 shows that depletion of endogenous ME2 enhances ROS generation, increases $NAD^+/NADH$ and $NADP^+/NADPH$ ratios, and decreases ATP levels. A: Accumulation of mitochondrially generated superoxide in K562 ME2 knockdown cells as detected by MitoSOX™. Data are representative of two independent experiments. B: Increased ROS in K562 ME2 knockdown cells detected by flow cytometry using CM-$H_2$DCF-DA. Each histogram is representative of three experiments. C: Comparison of oxidative damage to cardiolipin in ME2 knockdown versus control K562 cells. M1 indicates subpopulation of cells that lost NAO signal due to cardiolipin oxidation. D: Depletion of ME2 inhibits ATP production in K562 cells. Data are expressed as mean±SD, n=3. E: Depletion of ME2 increases $NAD^+$/NADH ratio. a, NAD and NADH were measured by NAD/NADH Assay Kit (Abcam, San Francisco, Calif.). Data are expressed as mean±SD, n=3. b, NAD+ and NADH were measured by LC-MS. F: Depletion of ME2 increases NADP/NADPH ratio in ME2 knockdown cells. NADP and NADPH were measured by LC-MS.

To determine if knockdown of ME2 promotes ROS production, we first analyzed superoxide production in K562 cells with ME2 depletion by using the superoxide detection reagent MitoSOX™ Red, a novel fluorogenic dye for highly selective detection of superoxide in the mitochondria of live cells. This reagent is live-cell permeant and is rapidly and selectively targeted to the mitochondria. Once in the mitochondria, it is rapidly oxidized by superoxide but not by other ROS— or reactive nitrogen species-generating systems. We therefore stained ME2 knockdown K562 cells with MitoSO™ Red, and observed the cells under fluorescence microscopy. We only found positive cells in ME2 deficient K562 cells as compared to controls (FIG. 4A). There was a significant increase in MitoSO™ red fluorescence in ME2 knockdown cells indicative of an increase in superoxide generation. The stability of superoxide is short-lived in cells, since superoxide dismutase rapidly converts it into $H_2O_2$. Therefore, we further assayed for $H_2O_2$ and other reactive species in response to ME2 knockdown as quantified by flow cytometry using CD-H$_2$DCF-DA as a fluorescent probe. Compared to an empty vector control, we observed a significant increase in basal ROS content in three independent ME2 shRNA knockdown cells (FIG. 4B). Furthermore, we detected oxidation of cardiolipin, a mitochondrial membrane lipid component by labeling with NAO. As shown in FIG. 4C, knockdown of ME2 caused massive cardiolipin oxidation. About 31.28% and 23.19% of ME2 depleted cells showed cardiolipin oxidation in two independent clones, respectively (FIG. 4C). Moreover, intracellular NADPH level has been considered as an effective antioxidant. In agreement with the increase of ROS in K562 cells, we found NADPH level decreased in ME2 knockdown cells, a result that was confirmed using metabolomic analysis described herein (FIG. 4F).

ME2 may play an important role in energy production fueled by glutamine. Therefore, we examined ATP production in cells with ME2 deficiency. As illustrated in FIG. 4D, knockdown of ME2 led to almost 50% ATP inhibition in three independent ME2 shRNA cells. Consistent with this observation, we noted a 2-fold increase in the $NAD^+$/NADH ratio in ME2 knockdown cells (FIG. 4E).

Figure 5:
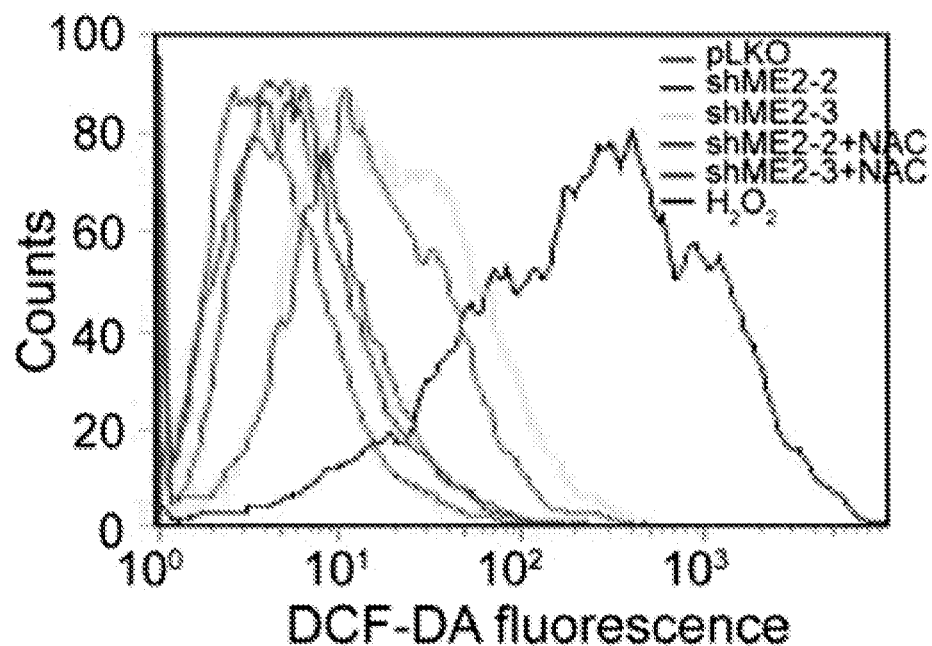
FIG. 5 shows that the antioxidant N-acetyl cysteine (NAC) cannot rescue ME2 knockdown induced erythroid differentiation in K562 cells. A: 5 mM NAC completely rescues ROS generation in K562 cells as detected by flow cytometry using CM-$H_2$DCF-DA. Each histogram is representative of three experiments. B: ROS inhibition by 5.0 mM NAC did not rescue ME2 knockdown induced erythroid differentiation in K562 cells. Each histogram is representative of three experiments.
Figure 5:
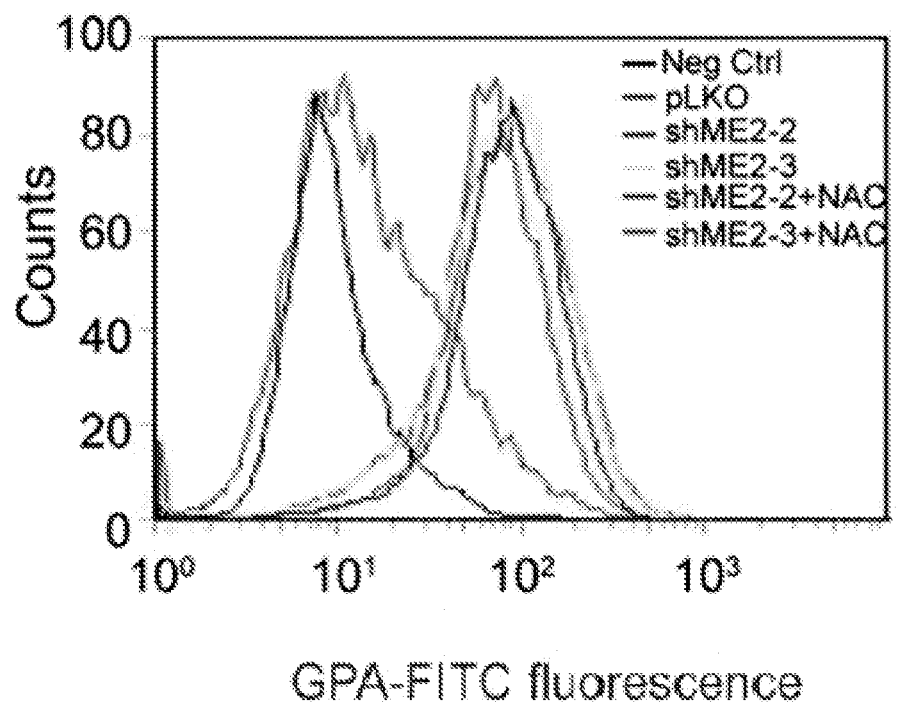

Inhibition of ROS does not rescue ME2 deficiency induced differentiation: ROS have been shown to induce K562 cell differentiation in vitro. We asked whether differentiation induced by knockdown of ME2 occurs via increased ROS generation. To answer this question, we inhibited ROS using NAC and examined differentiation in K562 leukemia cells induced by ME2 depletion. 5.0 mM NAC completely inhibited endogenous ROS in ME2 knockdown leukemia cells (FIG. 5A), without affecting differentiation (FIG. 5B), suggesting that ROS production is only a by-product of ME2 knockdown.

Figure 6:
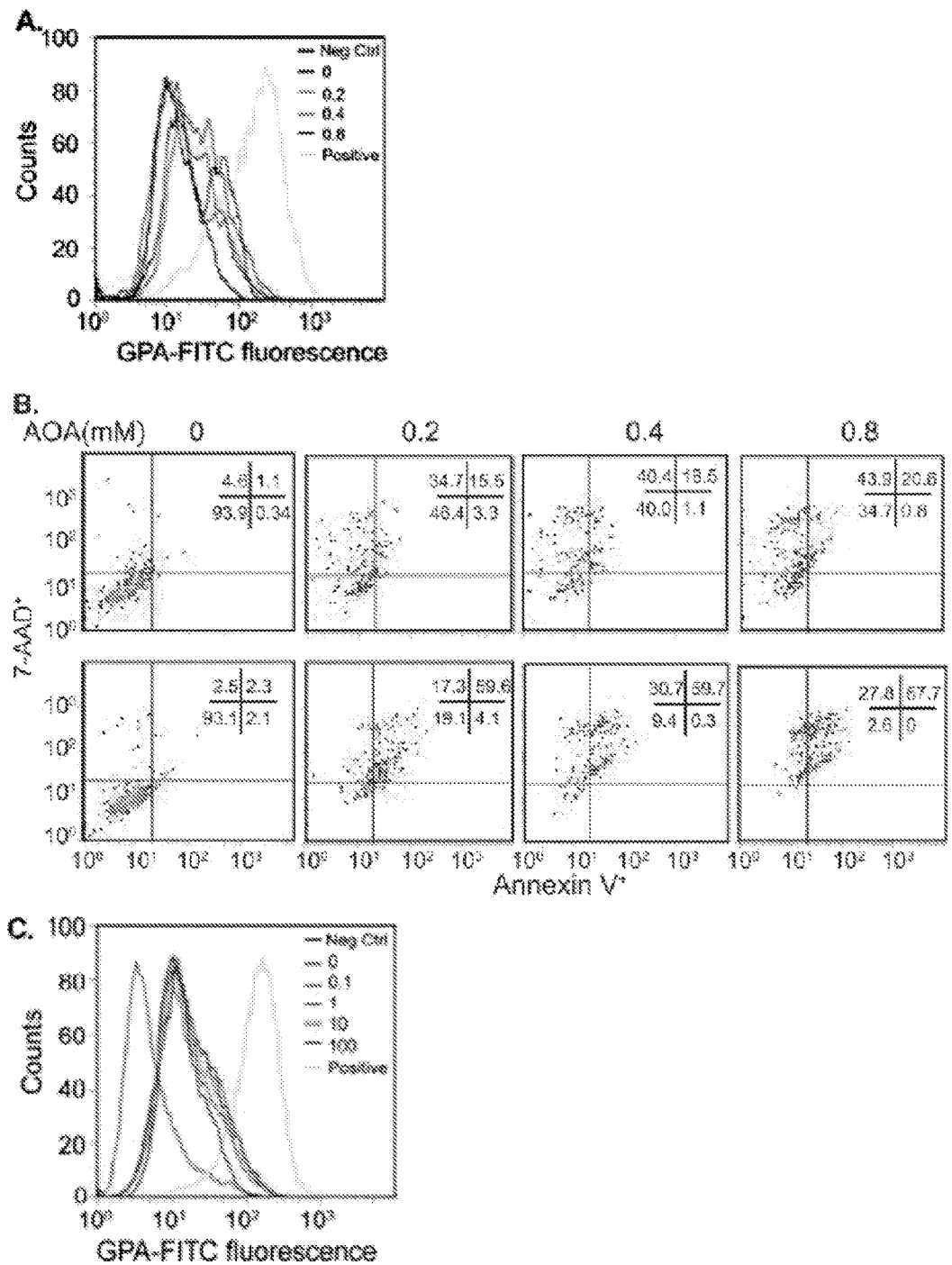
FIG. 6 shows that supplementation by exogenous amino-oxyacetate (AOA) and malate in medium cannot induce erythroid differentiation but does induce cell death. A: Cells were treated with different concentrations of amino-oxyacetate and expression levels of the erythroid marker glycophorin A (GPA) on the surface of K562 cells were assessed using a mouse FITC-conjugated anti-human glycophorin A antibody. Each histogram is representative of three experiments. B: K562 cells with or without ME2 knockdown were incubated with different concentrations of AOA for 72 h. Cell death was assessed by flow cytometry. Top: pLKO; Bottom: shME2-3. Data are representative of two independent experiments. C: Cells were treated with different concentrations of malate and expression levels of the erythroid marker glycophorin A on the surface of K562 cells were assessed using a mouse FITC-conjugated anti-human glycophorin A antibody. Each histogram is representative of three experiments.

Supplementation of exogenous malate cannot induce K562 differentiation: One function of ME2 is to convert malate to pyruvate, so that depletion of endogenous ME2 might lead to the accumulation of malate in mitochondria. Without wishing to be limited by theory, we hypothesized that the accumulation of malate in cells may be sufficient to cause K562 cellular differentiation. Therefore, with the assumption that exogenous malate is cell permeant, we evaluated the effects of exogenous malate on the differentiation of wild type K562 cells by supplementing the media with different concentrations of malate. As illustrated in FIG. 6C, exogenous malate from 0.1 to 10 mM could not induce erythroid differentiation in K562 cells.

The malate-aspartate shuttle (MAS) inhibitor amino-oxyacetate (AOA) cannot induce K562 differentiation but induces cell death: Another function of ME2 is to generate NADH in the mitochondria. We wondered if the ME2 knockdown phenotype (K562 differentiation) might be due to decreased production of mitochondrial NADH. Since the primary function of the MAS shuttle is to transport malate into mitochondria and in so doing essentially transfer cytosolic NADH equivalents into mitochondria, we hypothesized that blockade of the MAS might cause differentiation. To test this hypothesis, we used AOA, which when added exogenously, is known to inhibit the aminotransferase in the MAS. As illustrated in FIG. 6A, AOA from 0.2 to 0.8 mM in the medium could not induce erythroid differentiation in K562 cells as assessed by glycophorin staining.

Figures 10, 11:
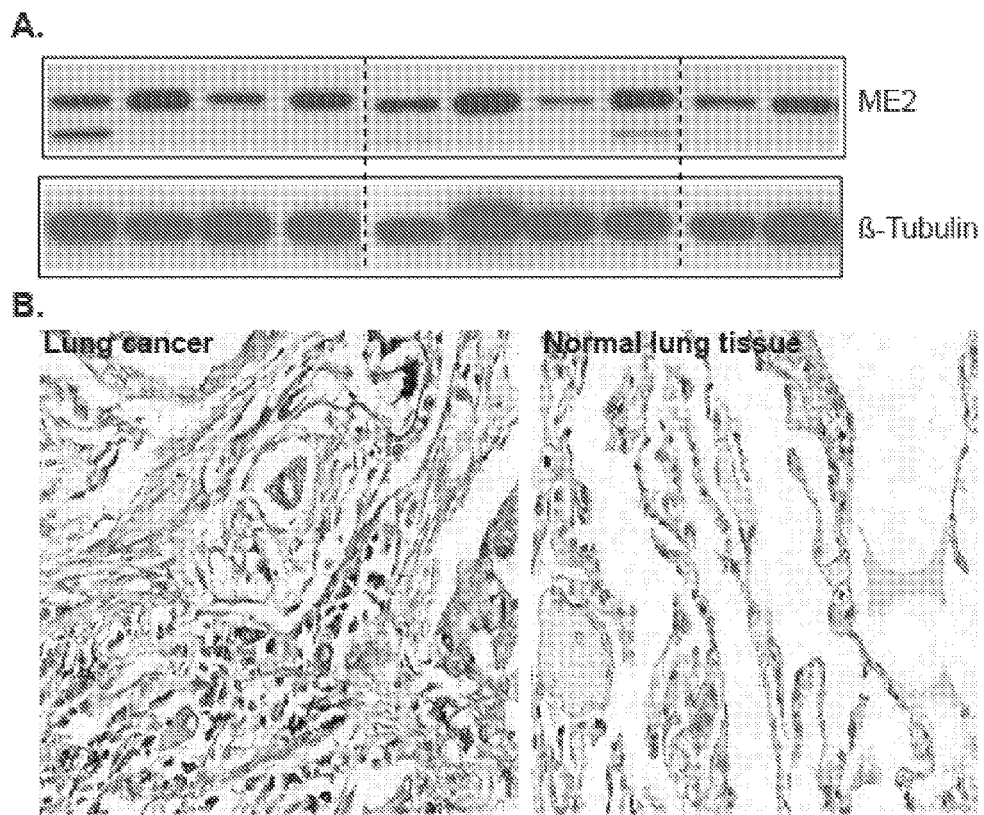
FIG. 10 shows the effect of α-ketoglutarate (α-KG) on AOA-induced K562 cell death. K562 cells with or without ME2 knockdown were incubated with 0.1 mM AOA plus 2 mM α-KG for 48 h. Cell death was assessed by flow cytometry. A: pLKO K562 cells without any treatment. B: pLKO K562 cells treated with 0.1 mM AOA for 48 h. C: pLKO K562 cells treated with 0.1 mM AOA combined with 2 mM α-KG. Data are representative of two independent experiments.
FIG. 11 shows ME2 expression in lung cancer. A: Human lung cancer tissues lysed in RIPA buffer were purchased from Protein Biotechnologies and analyzed for ME2 and β-tubulin expression by Western blotting. B: Representative image from a lung cancer sample and adjacent normal lung stained with ME2 antibody.

Next, we hypothesized that blockade of the MAS in ME2 depleted cells might lead to enhanced cell death, perhaps by further decreases in mitochondrial NADH. Though no differentiation was observed in AOA treated leukemia cells (FIG. 6A), the response of ME2 knockdown and control cells to AOA treatment was quite dramatic. AOA induced leukemia cell death (mainly apoptotic) when ME2 was silenced (FIG. 6B, bottom). In wild type K562 cells, AOA induced leukemia cell death (mainly necrotic) (FIG. 6B, top). Interestingly, $\alpha$-ketoglutarate ($\alpha$-KG) could rescue AOA mediated cell death (FIG. 10) suggesting that the effect of AOA was likely due to blockade of glutamate to $\alpha$-KG, conversion, since AOA is known to be a nonspecific inhibitor of pyridoxal phosphate-utilizing enzymes. ME2 knockdown-induces K562 differentiation via the PI3K/AKT pathway: A large body of evidence indicates that the erythroid differentiation is accompanied by activation of the PI3K/AKT pathway, while megakaryocytic differentiation is accompanied by activation of the MAPK kinase pathway. In the case of erythroid differentiation, activation of PI3K/AKT is not merely an association, since blockade of this pathway inhibits differentiation.

Figure 7:
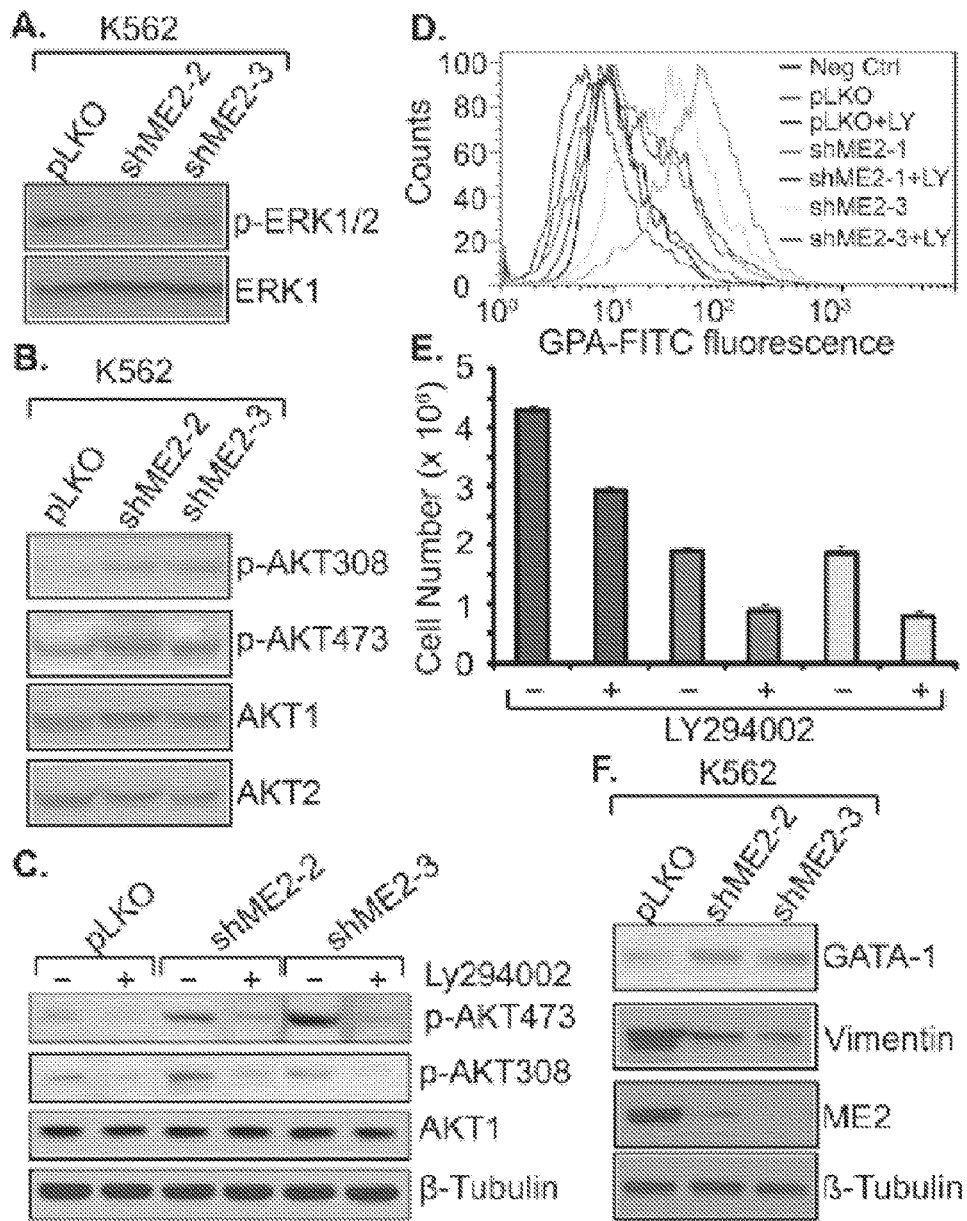
FIG. 7 shows the effects of ME2 knockdown on signaling pathways and the expression of GATA-1 and vimentin. K562 cells with or without ME2 knockdown were lysed with RIPA lysis buffer (50 mM Tris-HCl, pH 8.0, 150 mM NaCl, 1% Triton X-100, 1 mM EGTA) containing 1 mM PMSF and a protease inhibitor cocktail and subjected to centrifugation at 15,000×g for 10 mM at 4° C. to remove debris. After lysis, equal aliquots of protein lysate were resolved by Western blotting. Western blots were probed with anti-phospho-ERK1/2, anti-ERK1, anti-p-AKT308, anti-AKT472, anti-AKT1/2, anti-GATA-1, anti-vimentin, and anti-β-tubulin. A: Phospho-ERK1/2 activity in ME2 knockdown K562 cells. B: Phospho-AKT detection in ME2 knockdown K562 cells. C: 10 μM PI3K inhibitor, LY294002, inhibits p-AKT activity. D: LY294002 rescue of differentiation in ME2 knockdown K562 cells. E: The effect of LY294002 on the proliferation of K562 cells with (third to sixth bars in graph) or without ME2 (first to second bars in graph) knockdown. F: The expression difference of GATA-1 and vimentin in ME2 knockdown cells. Data are representative of three independent experiments.

We examined changes in these two pathways in ME2 depletion-induced differentiation. Knockdown of ME2 using two independent shRNAs resulted in a decrease in phospho-ERK levels (FIG. 7A). In contrast, the phospho-AKT308 and phospho-AKT473 levels increased (FIG. 7B). Furthermore, LY294002, a PI3 kinase inhibitor, which has been shown to inhibit AKT activity, rescues the differentiation mediated by ME2 silencing (FIGS. 7C, D, and E). As shown in FIG. 7E, we observed that the proliferation inhibition in ME2 knockdown cells is more sensitive to LY294002 treatment (third to sixth bars in graph), as compared to its parenteral K562 cells (first to second bars in graph). Although LY294002 treatment can significantly inhibit p-AKT activity and rescue differentiation cause by ME2 depletion, LY294002 does not rescue proliferation inhibition in ME2 knockdown cells as effectively. These data are consistent with literature (see, e.g., Meshkini et al., *Toxicol. In vitro.* 22: 1503-1510 (2008); Missiroli et al., *Int. J. Biochem. Cell. Biol.* 41: 570-577 (2009); and Kang et al., *FEBS Lett.* 577: 361-366 (2004)). GATA-1 is a transcription factor that is required and sufficient to induce erythroid differentiation. We observed a GATA-1 increase in ME2 knockdown cells (FIG. 7F). Vimentin expression is diminished during erythroid differentiation. Here, we found that vimentin was dramatically decreased in ME2 depleted cells (FIG. 7F). Without wishing to be limited by theory, our data suggest that the differentiation induced by ME2 knockdown is most likely a PI3K/AKT regulated event which also includes ERK repression, the activation of GATA-1 transcription, and diminished expression of vimentin.

Figure 8:
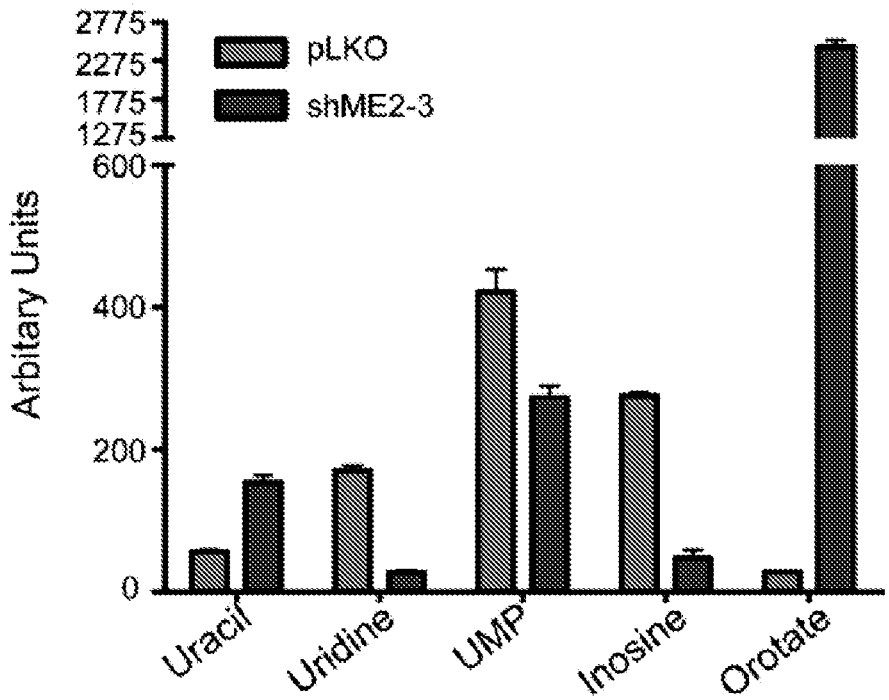
FIG. 8 shows that knockdown of ME2 alters pyrimidine metabolism in K562 cells. The metabolites were measured by LC-MS. Data are shown for control (left bars for each metabolite) and shME2-3 (right bars for each metabolite).

Knockdown of endogenous ME2 levels impairs pyrimidine metabolism in K562 cells: Several reports indicate that impairment of pyrimidine metabolism induces leukemia cells differentiation (see, e.g., Matsumoto et al. *Biochem. Pharmacol.* 39: 455-462 (1990)). Interestingly, in our metabolomic analysis of ME2 knockdown cells, we noted that there was a marked increase in the metabolite orotate (approximately 90-fold) in ME2 knockdown cells when compared to controls (FIG. 8 and Table 1). Orotate is an intermediate in pyrimidine de novo synthesis. The de novo synthesis of pyrimidine nucleotides requires 6 enzymes, including carbamoyl phosphatase synthetase, aspartate transcarbamylase, dihydroorotase, and dihydroorotase dehydrogenase. The last two steps are cytoplasmic and are catalyzed by the bifunctional enzyme orotate phosphoribosytransferase/oritidine-5'-monophosphate decarboxylase. Orotate accumulation in ME2 deficient K562 cells is suggestive of a block in the synthesis or activity of UMP synthase. In support of this hypothesis, we also found modest decreases in UMP, though we are not able to explain the lower levels of uridine, cytidine and inosine (the latter involved in purinergic pathways) in ME2 knockdown cells when compared with controls (FIG. 8 and Table 1).

TABLE 1

Metabolite levels in lysates from control K562 (pLKO) and ME2 knockdown (shME2-3) cells. The metabolites were measured by LC-MS method as described in "Materials and Methods."

| Metabolite | pLKO | SD | shME2-3 | SD |
| --- | --- | --- | --- | --- |
| lactose | 4.3 | 1.6 | 3.4 | 0.1 |
| sucrose | 5.0 | 2.2 | 3.5 | 0.4 |
| sorbitol | 252.4 | 19.6 | 234.3 | 16.4 |
| F1P | 2595.1 | 463.7 | 2756.8 | 58.6 |
| glucose (fructose, galactose) | 18348.7 | 1904.0 | 15589.8 | 310.9 |
| G6P | 9345.9 | 2534.0 | 8023.2 | 429.6 |
| F6P/G1P | 5216.7 | 1017.2 | 4877.5 | 290.0 |
| F-1,6-bisphophate (F-2,6-diP, G-1,6-diP) | 235.2 | 83.8 | 457.2 | 63.7 |
| DHAP | 1926.7 | 811.3 | 3147.0 | 311.0 |
| PEP | 594.3 | 158.0 | 1251.2 | 110.5 |
| pyruvate | 11302.5 | 984.8 | 10107.9 | 274.8 |
| lactate | 31533.9 | 2151.8 | 27961.8 | 206.0 |
| ribose-5-phosphate | 911.8 | 110.6 | 1270.5 | 68.9 |
| ribulose-5-phosphate | 1615.3 | 359.9 | 2183.5 | 127.9 |
| citrate | 1535.7 | 728.5 | 1874.7 | 305.7 |
| aconitate | 209.1 | 67.1 | 212.0 | 45.1 |
| isocitrate | 156.3 | 56.7 | 151.6 | 4.3 |
| alpha-ketoglutarate (adipate) | 1492.6 | 559.9 | 1278.8 | 384.7 |
| succinate (methylmalonate) | 78304.5 | 4068.6 | 71451.5 | 806.0 |
| fumarate | 1991.3 | 204.6 | 1744.7 | 109.0 |
| malate | 71524.4 | 9572.4 | 62307.6 | 1281.9 |
| oxalate | 59.0 | 26.1 | 67.1 | 11.8 |
| maleate | 1978.0 | 317.6 | 1704.0 | 126.7 |
| adenylosuccinate | 23.4 | 4.6 | 9.8 | 2.1 |
| alpha-glycerophosphate | 5636.8 | 699.9 | 5587.1 | 136.7 |
| malonate | 871.9 | 193.0 | 725.1 | 212.6 |
| 2-aminodipate | 38.7 | 2.1 | 39.5 | 2.6 |
| hydroxy-phenylpyruvate | 8.4 | 14.5 | 7.6 | 9.5 |
| glyceraldehyde | 840.0 | 77.1 | 721.3 | 9.2 |
| cystathionine | 170.1 | 34.0 | 165.1 | 13.3 |
| pantothenate | 66588.0 | 7678.2 | 84666.1 | 1908.2 |
| 4-pyridoxate | 4.3 | 0.7 | 4.1 | 0.6 |
| 5-methyl-THF | 0.8 | 1.3 | 0.0 | 0.0 |
| folate | 372.6 | 41.0 | 372.8 | 13.3 |
| UDP-glucose (UDP-galactose) | 5272.4 | 795.0 | 6792.5 | 195.3 |
| UDP-glucuronate | 1257.0 | 25.8 | 1200.5 | 73.8 |
| urate | 1597.0 | 366.6 | 1197.0 | 78.3 |
| kynurenine | 23.6 | 2.7 | 21.9 | 0.4 |
| niacin | 15.3 | 26.5 | 0.0 | 0.0 |
| NAD | 13175.7 | 2009.7 | 11381.0 | 399.6 |
| NADH | 922.7 | 34.4 | 408.8 | 136.9 |
| NADP | 254.6 | 129.3 | 293.7 | 57.1 |
| NADPH | 297.2 | 268.1 | 38.8 | 67.2 |
| adenine | 71.9 | 11.8 | 51.5 | 13.0 |
| thymine | 0.0 | 0.0 | 22.8 | 1.2 |
| uracil | 56.5 | 4.9 | 154.5 | 16.1 |
| AMP | 1059.7 | 248.1 | 805.2 | 44.1 |
| ADP | 5834.0 | 868.2 | 5027.5 | 26.2 |
| cAMP | 52.8 | 11.1 | 44.7 | 1.8 |
| cytidine | 56.7 | 9.6 | 20.7 | 4.7 |
| CMP | 58.7 | 11.5 | 44.8 | 2.0 |
| CDP | 5.7 | 1.0 | 7.2 | 1.1 |
| dCDP | 1.2 | 0.2 | 1.2 | 0.2 |
| dCMP | 3.4 | 5.8 | 1.7 | 2.9 |
| guanosine | 27.4 | 8.9 | 6.6 | 1.5 |
| GMP | 89.0 | 15.7 | 71.6 | 5.3 |
| GDP | 318.2 | 36.5 | 276.9 | 9.2 |
| uridine | 170.3 | 12.2 | 27.2 | 5.7 |
| UMP | 421.8 | 54.8 | 273.3 | 28.0 |
| UDP | 924.9 | 268.2 | 1164.9 | 125.4 |
| dUMP | 5.7 | 2.3 | 4.3 | 3.8 |
| inosine | 275.9 | 7.2 | 47.8 | 19.2 |
| IMP | 217.2 | 24.7 | 128.7 | 19.7 |
| xanthine | 410.4 | 8.3 | 454.4 | 31.2 |
| hypoxanthine | 395.7 | 13.1 | 306.8 | 19.5 |
| orotate | 28.5 | 1.6 | 2454.7 | 148.6 |
| palmitate | 46873.2 | 6747.6 | 39822.2 | 2223.0 |
| palmitoleate | 792.0 | 114.8 | 835.9 | 97.1 |
| stearate | 4325.0 | 645.2 | 3290.4 | 78.6 |
| oleate | 6281.7 | 347.7 | 5571.3 | 374.9 |
| linoleate | 1926.7 | 222.0 | 1965.9 | 402.3 |
| gamma-linoleate | 159.7 | 44.6 | 142.8 | 28.0 |
| arachidonate | 124.6 | 22.8 | 374.2 | 9.8 |
| EPA | 265.8 | 19.8 | 250.6 | 5.9 |
| acetoacetate | 9.6 | 4.1 | 6.8 | 1.7 |
| PGE2 | 37.7 | 25.4 | 45.8 | 21.1 |
| deoxycholate | 21.4 | 13.7 | 37.5 | 23.7 |
| glycocholate | 19.1 | 2.5 | 17.0 | 2.3 |
| glycodeoxycholate | 21.2 | 0.7 | 18.7 | 1.4 |
| taurocholate | 13.2 | 2.3 | 9.7 | 1.8 |
| taurodeoxycholate | 17.0 | 4.2 | 11.5 | 1.7 |
| taurolithocholate | 13.1 | 1.3 | 11.3 | 1.3 |
| lithocholoate | 46.4 | 14.3 | 37.7 | 4.1 |
| glucuronate | 27.7 | 1.1 | 31.2 | 1.7 |
| glutathione oxidized | 8731.6 | 3250.3 | 11558.1 | 447.4 |
| glutathione reduced | 987.8 | 546.2 | 1268.5 | 814.6 |
| 5-HIAA | 31.7 | 3.3 | 33.6 | 2.0 |
| bilirubin | 34.2 | 26.3 | 14.9 | 11.2 |
| hippurate | 484.7 | 19.4 | 533.9 | 13.9 |
| salicylurate | 10.7 | 3.6 | 7.0 | 1.7 |
| 4-hydroxybenzoate | 165.8 | 12.8 | 169.2 | 6.3 |
| PPA | 97.1 | 10.4 | 82.3 | 15.0 |
| geranyl pyrophosphate | 13.8 | 15.5 | 55.0 | 17.4 |
| glycine | 121.0 | 7.1 | 107.3 | 4.3 |
| alanine | 3039.0 | 287.6 | 2903.7 | 213.8 |
| serine | 2310.5 | 153.3 | 2209.6 | 24.9 |
| threonine | 3793.2 | 101.3 | 3489.0 | 198.3 |
| asparagine | 895.3 | 20.1 | 804.7 | 72.8 |
| glutamine | 71174.5 | 2418.5 | 69684.2 | 4526.8 |
| aspartate | 1312.8 | 104.4 | 1198.7 | 100.7 |
| glutamate | 9962.9 | 313.5 | 12372.5 | 685.0 |
| arginine | 16170.6 | 1728.2 | 15555.5 | 162.7 |
| lysine | 16617.4 | 1444.4 | 15966.1 | 905.1 |
| histidine | 9228.2 | 1219.0 | 8956.1 | 120.7 |
| leucine | 38598.5 | 2448.1 | 38874.4 | 1178.9 |
| isoleucine | 42127.0 | 2807.1 | 43540.1 | 1994.4 |
| valine | 25505.0 | 1294.2 | 25379.7 | 211.3 |
| phenylalanine | 66095.7 | 5528.1 | 69805.0 | 1810.0 |
| tyrosine | 6783.2 | 679.8 | 7066.0 | 478.6 |
| typtophan | 14735.5 | 1375.5 | 15438.2 | 456.8 |
| proline | 41445.5 | 1422.7 | 35503.5 | 171.9 |
| methionine | 2676.0 | 242.6 | 2833.9 | 158.6 |
| carnitine | 2111.4 | 84.3 | 2589.5 | 121.2 |
| carnosine | 142.6 | 22.4 | 138.0 | 1.5 |
| citrulline | 81.3 | 21.2 | 79.9 | 4.6 |
| ornithine | 176.2 | 22.1 | 176.4 | 72.3 |
| allantoin | 444.9 | 39.6 | 458.8 | 18.1 |
| cis/trans-hydroxyproline | 0.0 | 0.0 | 0.0 | 0.0 |
| histamine | 52.4 | 90.7 | 33.0 | 19.6 |
| homocysteine | 0.0 | 0.0 | 0.0 | 0.0 |
| GABA | 119.3 | 18.7 | 191.3 | 34.7 |
| taurine | 2178.0 | 276.0 | 3560.4 | 202.9 |
| thyroxine | 5.3 | 0.2 | 4.5 | 0.2 |
| serotonin | 497.8 | 27.8 | 548.3 | 60.9 |
| 5-HIAA | 0.0 | 0.0 | 0.0 | 0.0 |
| creatine | 16058.7 | 832.1 | 16017.5 | 1379.2 |
| creatinine | 1268.5 | 73.8 | 1244.0 | 65.6 |
| dimethylglycine | 75.0 | 2.7 | 67.2 | 4.7 |
| betaine | 10488.0 | 473.2 | 10330.3 | 285.6 |
| choline | 33719.9 | 1168.1 | 32562.9 | 3773.0 |
| acetylcholine | 63.1 | 14.8 | 37.6 | 3.9 |
| alpha-glycerophosphocholine | 2529.6 | 248.0 | 2001.6 | 79.8 |
| phosphoethanolamine | 0.0 | 0.0 | 21.8 | 4.0 |
| adenosine | 442.0 | 61.7 | 1174.6 | 993.7 |
| thymidine | 18.9 | 4.9 | 7.1 | 6.9 |
| 2'-deoxyadenosine | 83.9 | 8.6 | 265.7 | 332.1 |
| 2'-deoxycytidine | 0.8 | 0.5 | 0.7 | 0.1 |
| 2'-deoxyuridine | 23.2 | 2.1 | 0.0 | 0.0 |
| xanthosine | 76.6 | 7.2 | 80.0 | 5.7 |
| 3-OH-anthranilic acid | 0.0 | 0.0 | 0.0 | 0.0 |
| 5'-adenosylhomocysteine | 42.0 | 4.4 | 43.3 | 1.5 |
| ADMA/SDMA | 200.5 | 29.2 | 196.0 | 30.8 |
| anthranilic acid | 0.0 | 0.0 | 0.0 | 0.0 |

TABLE 1-continued

Metabolite levels in lysates from control K562 (pLKO) and ME2 knockdown (shME2-3) cells. The metabolites were measured by LC-MS method as described in "Materials and Methods."

| Metabolite | pLKO | SD | shME2-3 | SD |
| --- | --- | --- | --- | --- |
| argininosuccinate | 0.0 | 0.0 | 0.0 | 0.0 |
| cotinine isomer | 713.4 | 139.5 | 731.1 | 166.5 |
| glycerol | 9.5 | 3.0 | 9.3 | 2.2 |
| kynurenic acid | 84.3 | 15.9 | 98.4 | 18.2 |
| N-carbamoyl-beta-alanine | 386.7 | 36.0 | 405.8 | 27.6 |
| trimethylamine-N-oxide | 94.0 | 15.2 | 78.9 | 8.3 |
| tyramine | 2.2 | 3.9 | 69.7 | 119.3 |
| niacinamide | 19691.1 | 1748.5 | 19991.9 | 875.6 |
| pyridoxine | 94264.1 | 12757.9 | 104394.4 | 10504.8 |
| thiamine | 20528.0 | 2246.5 | 20599.2 | 372.9 |
| cobalamin | 0.0 | 0.0 | 0.0 | 0.0 |
| NMMA | 32.8 | 4.6 | 31.1 | 10.9 |
| carnitine isomer | 174.9 | 10.3 | 177.3 | 6.3 |

The metabolic profiling of differentiation and apoptosis in leukemia cells in response to drug treatment can be different (Tozani et al., PLoS One. 4: e4251 (2009)). ME2 is a mitochondrial enzyme that catalyzes the conversion of malate to pyruvate. It is believed that ME2, via the generation of NADH and pyruvate products, may play an important role in the metabolism of glutamine, which is needed to produce both reducing equivalents and energy in rapidly proliferating tissues such as tumors. ME2 is regulated by ATP which acts as an inhibitor and by fumarate which acts as an activator of its catalytic activity. This regulation is consistent with the functional role of this enzyme, as ATP is an overall product of energy metabolism and fumarate is generated by the previous step in the TCA cycle. We compared metabolite changes between ME2 knockdown and control K562 cells, and found that the most distinct change is in orotate, which is involved in pyrimidine metabolism. Though we expected that the malate level in mitochondria might be increased, no changes in the total malate level (mitochondrial plus cytosolic) were observed, and levels of malate in each compartment were not determined.

We might have expected that orotate accumulation would lead to a block in DNA synthesis and S phase progression. However, cell cycle analysis of ME2 knockdown cells did not indicate a block in late G1 or early S phase, nor were we able to rescue the ME2 cell cycle phenotype (decreased proliferation) by supplementation with uridine and cytidine.

Discussion

We have provided the first evidence that the malic enzyme family member ME2 is important in tumor biology; in particular, in the differentiation program of K562 cells. A striking phenotype that we observed upon ME2 knockdown, namely the induction of erythroid differentiation and the inhibition of tumor growth, has previously been observed by other manipulations that affect metabolic pathways in K562 cells. For example, inhibition of BCR-ABL signaling by treatment with imatinib in K562 cells would be expected to decrease glycolysis. K562 differentiation along the erythroid lineage has also been noted after silencing of ATP citrate lyase, a key enzyme in lipid synthesis.

The mechanism by which depletion of ME2 causes tumor cell differentiation remains to be elucidated. One possibility is that malate accumulation plays a role, though our metabolite analysis of whole cell extracts does not appear to support this, since malate levels showed no change in total (mitochondrial plus cytosolic) amount in ME2 knockdown cells, as compared with control cells (Table 1). It is conceivable though that mitochondrial malate may be increased in the ME2 knockdown cells. Malate enters the mitochondria from the cytosol (via the malate-aspartate shuttle). Since the function of ME2 is to convert malate to pyruvate, it is reasonable to assume that the accumulation of malate in mitochondria may be playing a mechanistic role. Supplementation of exogenous malate failed to induce K562 differentiation, suggesting that accumulation of this metabolite alone cannot drive differentiation. However, we cannot rule this possibility either, since malate sodium may not be able to get into the cell and into mitochondria. Therefore, it is still possible that mitochondrial malate accumulation explains some of the ME2 knockdown phenotype.

A second possibility is that NADH depletion explains our findings. Mitochondrial reducing equivalent shuttles are critical in regulating the balance in $NAD^+$:NADH levels between the cytoplasm and the mitochondria. The resultant effect of shuttle activity is the net transfer of NADH across the inner mitochondria membrane, in the production of ATP and the regeneration of $NAD^+$ in the cytoplasm enabling further glucose metabolism and lactate production. The increased drive to accumulate malate in mitochondria due to ME2 silencing may prevent the transferring of malate from cytosol to mitochondria, and render less effective the function of the malate-aspartate shuttle from transferring reduced equivalents from extra-mitochondrial to intra-mitochondrial compartments. Our metabolite data in Table 1 showing decreased NADH/$NAD^+$ ratio in ME2 knockdown cells is consistent with this view. Disruption of MAS has been reported to impair viability and fetal growth in mouse blastocysts. In our current investigation we have shown that AOA, an MAS inhibitor, cannot induce K562 differentiation. Instead, we found that AOA induces cell death: apoptosis in ME2 knockdown cells and necrosis in the control cells. The mechanism by which AOA plays different roles in control and knockdown ME2 cells remains to be investigated; it is possible that ATP levels differ under these circumstances. The cause of cell death from AOA is likely due to inhibition of the conversion of glutamate to α-KG, since α-KG rescued the cell death effect.

A third possibility is that pyruvate depletion by ME2 silencing plays a role; however, our metabolite data, given that it is whole cell lysate data, does not definitively address this hypothesis.

We noted that the tumorigenic potential of ME2 deficiency K562 cells in vivo was completely absent since injection of those cells into nude mice failed to generate solid tumors. This is intriguing in light of the fact the K562 cells that are fully differentiated as a result of ME2 knockdown in vitro are still growing albeit at a slower rate. It is possible that the knockdown of ME2 indirectly disrupts additional unidentified pathways that are of functional relevance in vivo, e.g., pathways that establish tumor take but do not manifest in vitro.

Increased ROS generation is an important phenotype of highly glycolytic cancer cells. ROS levels in cancer cells is also to be regulated by the oncogenes, such as Ras, Myc and Bcr-Abl and the tumor suppressor p53. Many anticancer drugs enhance ROS production and thereby damage cell integrity. However, the manipulation of cellular levels of ROS (smaller increases in ROS than what are needed to cause cell death) can induce cancer cell differentiation. Our studies indicate that silencing of ME2 in K562 cells is accompanied by enhanced ROS generation and increased $NAD^+$/NADH and $NADP^+$/NADPH ratios. Surprisingly, inhibition of ROS generation by treatment with the antioxidant N-acetyl-cysteine (NAC) could not reverse this differentiation in ME2 knockdown cells, demonstrating that although ROS is produced during K562 differentiation, ROS removal alone was insufficient to inhibit differentiation of K562 cells. The decrease in ATP by about 50%, perhaps due to decreased availability of NADH, may be a contributing factor. In addition it is conceivable the reducing power of NADH may lead to diminished capacity to maintain a high enough ratio of NADPH/NADP$^+$, thus compromising, reductive biosynthesis of fatty acids and cholesterol as well as nucleic acid synthesis, needed to fuel cell proliferation. Indeed, this sequence of events may account for the increase in ROS that results from depletion of ME2. Moreover, in K562 cells, depletion of ME2 induced K562 erythroid differentiation is accompanied by hemoglobin synthesis. Heme synthesis, which is localized to the mitochondrial matrix, is accompanied by ROS production. In the case of K562 cells, this may explain why we observed ROS levels increasing in the ME2 knockdown cells.

There may also be a link between glutamine usage and ME2. In order to obtain energy and the essential precursors for the synthesis of macromolecules, tumor mitochondria adapt by overexpressing glutaminase facilitating the use of glutamate as a fuel. High levels of ME2 can then allow pyruvate to be produced from malate within the mitochondria (see, e.g., Moreadith et al., *J. Biol. Chem.* 259: 6215-6221 (1984); Sauer et al., *J. Biol. Chem.* 255: 3844-3848 (1980); Board et al., *Biochem. J.* 265: 503-509 (1990); Mares-Perlman et al., *Cancer Res.* 48: 602-608 (1988); and Reitzer et al., *J. Biol. Chem.* 254: 2669-2676 (1979)). ME2 is one of the few progression-linked enzymes in Morris hepatoma series (Sauer et al., *J. Biol. Chem.* 255: 3844-3848 (1980)), as is a phosphate-dependent glutaminase, which strongly suggests an important role of ME2 in glutamine metabolism in tumors.

The oxidation of glutamate by tumor mitochondria is accompanied by metabolic interactions with cytosolic malate and/or pyruvate, and extrusion of citrate and alanine into the cytoplasm. These two major products play an important role in tumor metabolism. Citrate is required for fatty acid and cholesterol biosynthesis, the latter believed to be characteristically enhanced in tumor cells. Hatzivassiliou and colleagues found that knockdown of ATP citrate lyase (ACL) also induces K562 cell differentiation (Hatzivassiliou et al., *Cancer Cell.* 8: 311-321 (2005)). Acetyl-CoA is an important component of fatty acid and cholesterol biosynthesis in the cytosol, since it is the primary enzyme responsible for the synthesis of cytosolic acetyl-CoA which is important in lipid biosynthesis. Hence, inhibition of ACL leads to the disruption of lipid synthesis. These results suggest that stimulating cytosolic acetyl-CoA production and lipid synthesis may contribute to the suppression of tumor cell differentiation. Perturbation of the transition of TCA-to-lipid flux in the in vivo tumor microenvironment may allow a tumor cell to initiate an adaptive response such as differentiation in order to maintain its survival. The upregulation of specific metabolic intermediates may serve as signals to orchestrate these events. It is possible that citrate may work as an import molecule in this molecular switch. Therefore, disrupting citrate synthesis and transport to cytosol could be an important therapeutic window for targeted tumor therapy. The fact that ME2 selectively uses extra-mitochondria malate to synthesize pyruvate and export citrate for lipid synthesis suggests that malic enzyme might be ideal for this type of targeting. Our results indicated that depletion of ME2 suppresses K562 proliferation and induces differentiation in a manner similar to ACL knockdown. The differentiation induced by knockdown of ME2 and ACL could therefore have a common mechanism, namely inhibition of lipid synthesis.

However, our metabolomic analysis does not lend support to the idea that ME2 knockdown leads to diminished overall lipid synthesis though we have not made a formal measurement of lipid flux. We did observe significant shifts in lipid metabolism. Specifically, there were increases in polyunsaturated free fatty acids and lipids that contain polyunsaturated acyl groups, and decreases in lipids containing saturated lipids. This effect may be driven by the high levels of orotate in the knockdown cells and not directly by ME2 knockdown (see, e.g., Griffin et al., *Physiol. Genomics.* 17: 140-149 (2004)).

Orotate is an important precursor for pyrimidine de novo synthesis. The accumulation of orotate in ME2 depletion cells suggests that pyrimidine metabolism may be blocked. Some data suggests that inhibition of early de novo purine biosynthesis, or specific inhibition of de novo guanine nucleotide biosynthesis, may be an obligatory step in the initiation of differentiation in HL60 and K562 cells induced by certain drugs. Our data suggests that pyrimidine synthesis may be affected, although we were unable to demonstrate the G1/S arrest phenotype that might be expected if this were the mechanism involved in decreased cell proliferation observed in ME2 knockdown cells. Our data indicate that although the ME2 knockdown slowed cell growth, the cells did not accumulate in any one position in the cell cycle and in fact, supplementation with cytidine or uridine could not rescue the differentiation mediated by ME2 depletion. Also, the reason why depletion of ME2 leads to the accumulation of orotate is not known, though one target may be the activity or expression of UMP synthase.

Furthermore, ME2 depletion may affect other cancer cell types. We have found marked effects in several tumor types in vitro and in vivo: in MCF7 breast cancer cells and A549 non-small cell lung cancer cells, ME2 silencing leads to differentiation and to increased apoptosis.

K562 cells behave as pluripotent hematopoietic precursor cells. Studies have shown that drugs such as imatinib, butyrate, SB202190, hemin, hydroxyurea and Ara-C induce erythroid differentiation, whereas phorbol esters such as PMA induce megakaryocytic differentiation. Both differentiation pathways are driven by the activation of different signal transduction pathways. For megakaryocytic differentiation, cells require the activation of the ERK signaling pathway and the inhibition of p38 MAP kinase. For erythroid differentiation, ERK1/2 signaling inhibition and AKT signaling pathway and GATA-1 transcription factor activation are necessary. In our studies, we found ERK1/2 signaling to be inhibited, while AKT signaling was activated in ME2 knockdown K562 cells, consistent with our observed phenotype of erythroid differentiation. At what point in the signaling cascades ME2 knockdown has its effects is under investigation.

In conclusion, our data indicate that ME2 plays a crucial role in modulating K562 cell differentiation and growth and highlight a novel role for ME2 as a potentially attractive target for tumor therapy.

Example 2

ME2 Expression in Clinical Tumor Samples

We investigated ME2 expression in clinical tumor samples (from Protein Biotechnologies) by Western blotting. Eighty tumor specimen representing 13 types of solid tumors were probed by Western blotting with ME2 antibody (Sigma). ME2 overexpression was present in the majority of analyzed tumors, including lung (FIG. 11A), bladder, breast, esophagus, liver, ovary, prostate and skin. Moreover, we also investigated ME2 expression in a human tumor tissue array from US Biomax (anti-ME2 antibody from Sigma) and this data provided overall corroboration of the Western blot data. Increased ME2 expression was observed in lung cancer tissue, as compared to normal adjacent lung tissue (FIG. 11B). These data suggest that ME2 may play an important role in solid tumors, such as lung cancer.

Example 3

Generation and Characterization of ME2 Deficient Lung Cancer Cell Lines

Figure 12:
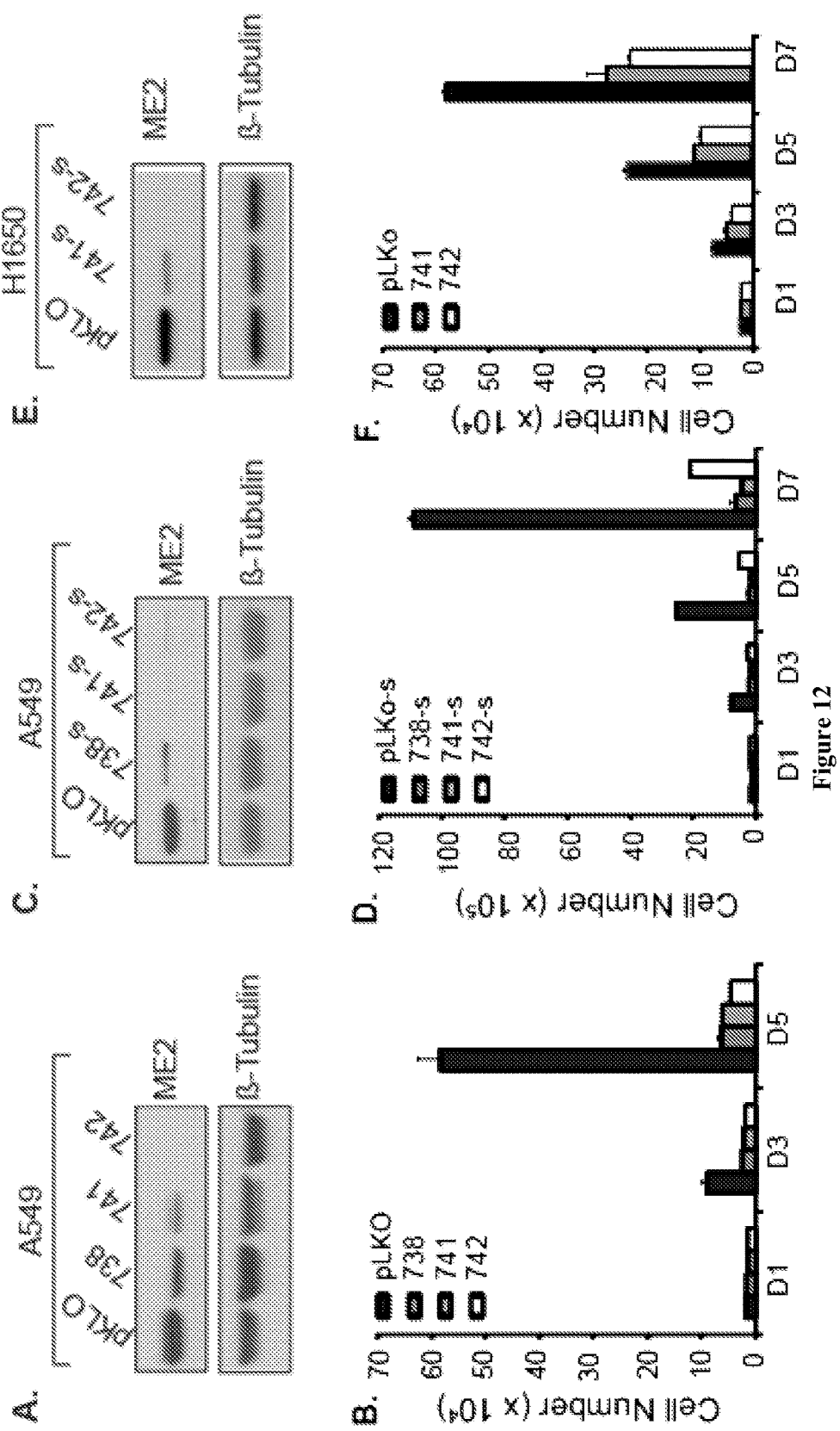
FIG. 12 shows the effects on lung cancer cell proliferation of independent shRNAs targeting ME2. A: Western blot analysis using an ME2 antibody (Sigma) of lysate from respective pools of A549 cells transduced with three independent ME2 shRNA lentiviruses (738 cells with shME2-1, 741 cells with shME2-2, and 742 cells with shME2-3), following selection of puromycin for 10 days. Data are representative of two independent experiments. All three pools showed marked ME2 silencing, where pLKO is provided as a control. B: Cell proliferation in A549 cells transduced with the indicated shRNA lentiviral constructs as described in "A." Data are representative of three independent experiments. C: Western blot analysis of cellular extracts in single clones of A549 cells demonstrating effective knockdown of ME2 levels with three ME2 shRNA lentiviruses (738-s cells with shME2-1, 741-s cells with shME2-2, and 742-s cells with shME2-3). Data are representative of two independent experiments. D: Cell proliferation of A549 single cell clones with ME2 knockdown derived from the corresponding pools as described in "C." Data are representative of three independent experiments. E: Western blot analysis of cellular extracts in H1650 cells with two independent ME2 shRNA lentiviruses (741 cells with shME2-2 and 742 cells with shME2-3) demonstrated effective knockdown of ME2 levels. F: Cell proliferation in H1650 cells transduced with the indicated shRNA lentiviral constructs as described in "E."

We generated A549 (non-small cell lung cancer) cells that are ME2 deficient by lentiviral shRNA induced RNA interference using three different RNA sequences. Knockdown of ME2 in A549 cells lines showed very little or no ME2 expression by Western analysis. Cell proliferation was markedly diminished in ME2 knockdown pools (FIGS. 12A and 12B) and single clones (FIGS. 12C and 12D) with all three shRNAs tested. These findings also apply to other non-small cell lung cancer (NSCLC) cell lines, such as those with one or more mutations that confer resistance to front-line anticancer agents. Since EFGR mutations are present in many patients with NSCLC, we assessed cellular proliferation in EGFR mutant TKI sensitive NSCLC cell line (H1650) using lentiviral shRNA induced RNA interference. For these cells, proliferation was diminished in ME2 knockdown pools, as compared to control (FIGS. 12E and 12F). Accordingly, RNA interference can be used in various cell lines to reduce ME2 expression.

Figure 13:
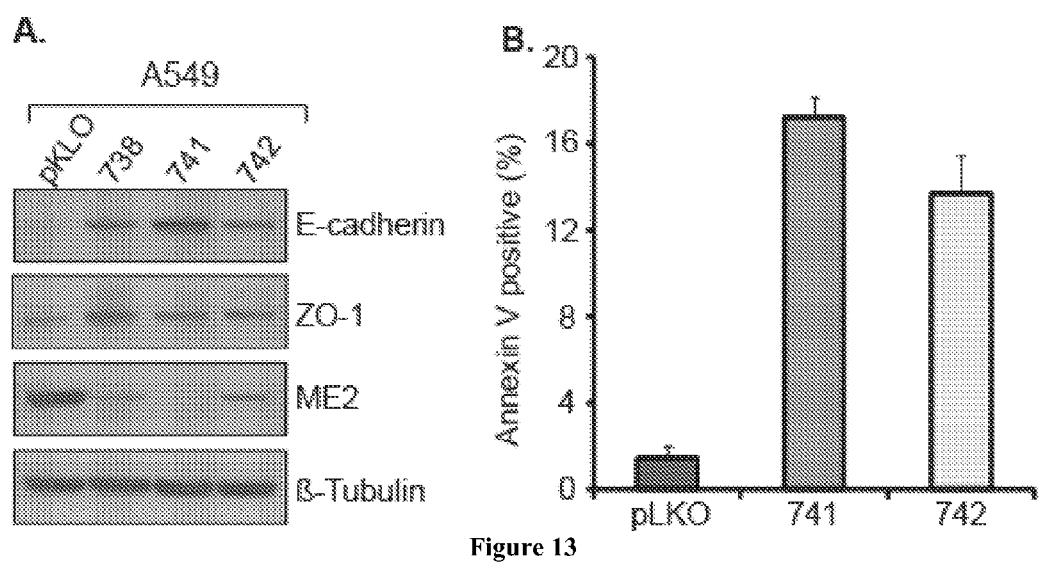
FIG. 13 shows that knockdown of ME2 induces A549 cells undergoing differentiation and apoptosis. A: Expression of differentiation markers E-cadherin and ZO-1 in control (pLKO) and ME2 knockdown A549 cells (738 cells with shME2-1, 741 cells with shME2-2, and 742 cells with shME2-3). B: Depletion of ME2 increases A549 basal apoptosis in 741 and 742 cells, as measured by annexin.

Morphologically, ME2 deficient cells showed a typical epithelial (cobblestone-like) morphology with an appositional growth pattern, whereas control A549 cells displayed more mesenchymal (spindle-shaped) features. Without wishing to be limited by theory, this observation suggests that ME2 may promote epithelial mesenchymal transition (EMT). Increased E-cadherin and ZO-1 levels strongly indicate that the ME2 deficient cells have undergone a reversal of EMT (FIG. 13A).

The rate of proliferation of ME2 deficient cells is about ⅓ the rate for control A549 cells (FIGS. 12B and 12D). In addition, annexin-V and cleaved caspase assays indicate that ME2 deficient cells have higher rates of apoptosis than control cells (FIG. 13B). Cell cycle analysis showed that ME2 deficiency caused only a modest increase in the number of cells in the G1 phase of the cell cycle. Accordingly, these data show that ME2 deficiency may contribute to two effects: increased differentiation as exemplified by a reversal of EMT and a decreased growth rate with apoptosis as the underlying mechanism. These effects were also observed in a conditional ME2 knockdown system, as described in Example 4 below.

Example 4

Downregulation of AKT Signaling in the ME2 Deficient State

Figure 14:
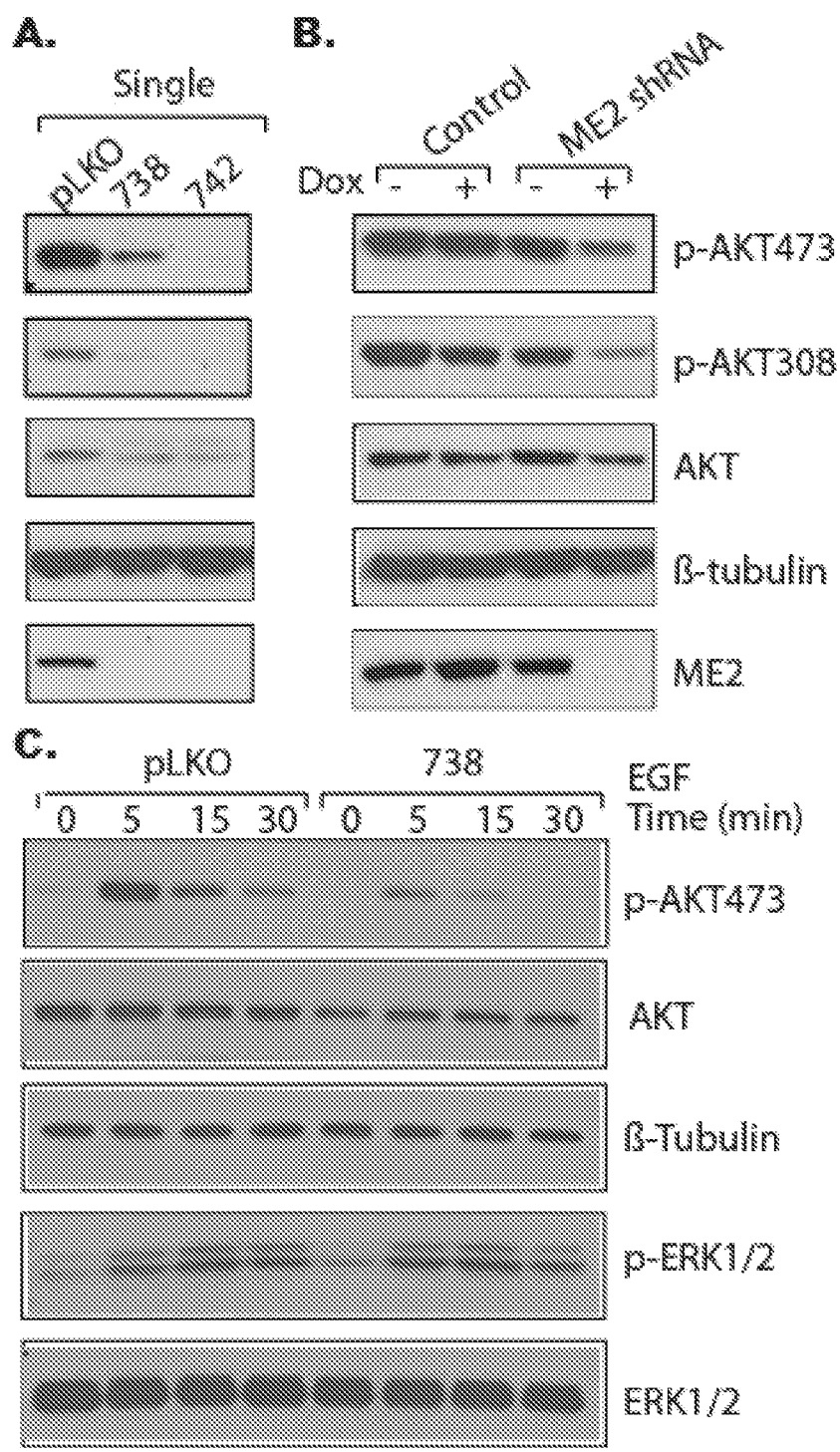
FIG. 14 shows that knockdown of ME2 inhibits AKT activity in A549 cells. A: Basal AKT activity in stable ME2 knockdown single clones (738 cells with shME2-1 and 742 cells with shME2-3). B: Doxycycline inducible shRNA induces ME2 knockdown and inhibits basal AKT activity in A549 cells. C: ME2 knockdown in 738 cells and control cells (pLKO) were starved for 24 hours, stimulated with 100 ng/ml EGF at the indicated time, and then lysed with RIPA buffer. Equal amount of protein were analyzed for phosphorylated AKT473 (p-AKT473), AKT, phosphorylated ERK1/2 (p-ERK1/2), ERK1/2, and β-tubulin by Western blotting.

To determine the effect of ME2 regulation in PI3K/AKT signaling, we measured the effects of ME2 deficiency on phospho-AKT levels. A549 control and ME2 deficient cells were plated in 6-well plates at approximately 50% confluency. Twenty four hours later, basal AKT activity was analyzed with pAKT T308 and pAKT 5473 antibody (Cell Signaling) (FIG. 14A). These data show that phosphorylation at both T308 and S473 is markedly diminished in the ME2 knockdown cells.

We also obtained similar data using a doxycycline (dox) inducible ME2 shRNA system (FIG. 14B). We created the system in A549 cells using lentiviral infection. Control cells with the pLKO vector were also generated. With two days of incubation with doxycycline, ME2 expression was clearly diminished in 738 cells carrying the ME2 specific hairpin (FIG. 14B).

Additionally, we also investigated AKT activity in response to EGF stimulation in ME2 knockdown cells. Serum starved A549 cells (with or without ME2 depletion) were stimulated with EGF for 0-30 minutes, as indicated in FIG. 14C. In response to EGF stimulation, ME2 deficient cells displayed downregulation of phospho-AKT levels, suggesting again that the ME2 deficient condition inhibits AKT signaling. There was no change in phospho-ERK1/2, supporting the notion that ME2 inhibition was unlikely to be acting by decreasing Ras activity, since Ras activation is known to increase ERK phosphorylation.

Accordingly, ME2 likely interacts with the PI3K/AKT signaling pathway, and these methods can be used to determine other proteins upstream of ME2, such as AKT, that effectively decrease or reduce ME2 gene expression, protein expression, or enzymatic activity, as compared to a control.

Example 5

PI3K Inhibition Mimics the ME2 Deficient Condition

Figure 15:
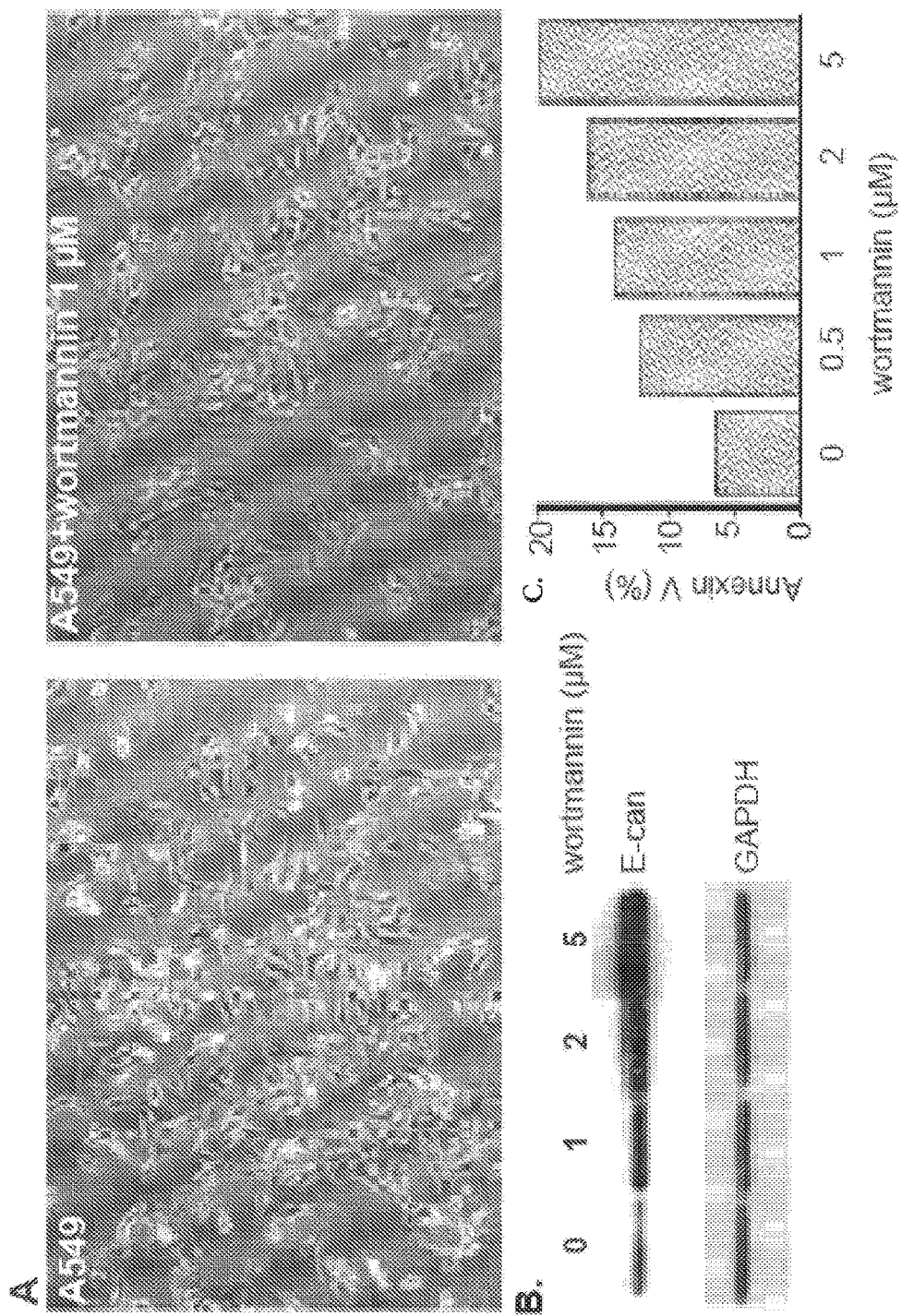
FIG. 15 shows that the action of a PI3K inhibitor wortmannin on A549 cells mimics the effects of ME2 deficiency. A: Phase contrast image of A549 cells before (left) and after (right) treatment with wortmannin. B: Wortmannin treated cells displayed increased expression of the differentiation marker E-cadherin (E-can). C: Apoptosis was observed in wortmannin treated cells.

We also determined the effect of PI3K inhibition in A549 cells. Treatment of control A549 cells with wortmannin showed a similar phenotype to that of ME2 deficient cells, namely, cobblestone morphology and an appositional growth pattern (FIG. 15A). Western blot analysis for E-cadherin indicated a dose-dependent increase of E-cadherin expression (FIG. 15B). Wortmannin also induced apoptosis of A549 cells in a dose dependent manner (FIG. 15C), and these data are similar to the ME2 deficient state. Similar data were obtained with another PI3K inhibitor, LY294002. Accordingly, the methods described herein include the use of indirect ME2 inhibitors, such as one or more inhibitors of PI3K (e.g., wortmannin and LY294002). Taking together the data from Examples 4 and 5, these methods and compositions also include inhibitors of AKT and/or PI3K, as well as inhibitors of one or more proteins that are upstream of AKT and/or PI3K (e.g., inhibitors of one or more of RTK, PDK1, mTORC2, or any other protein upstream of AKT and/or PI3K).

Example 6

In Vivo Tumor Model

Figure 16:
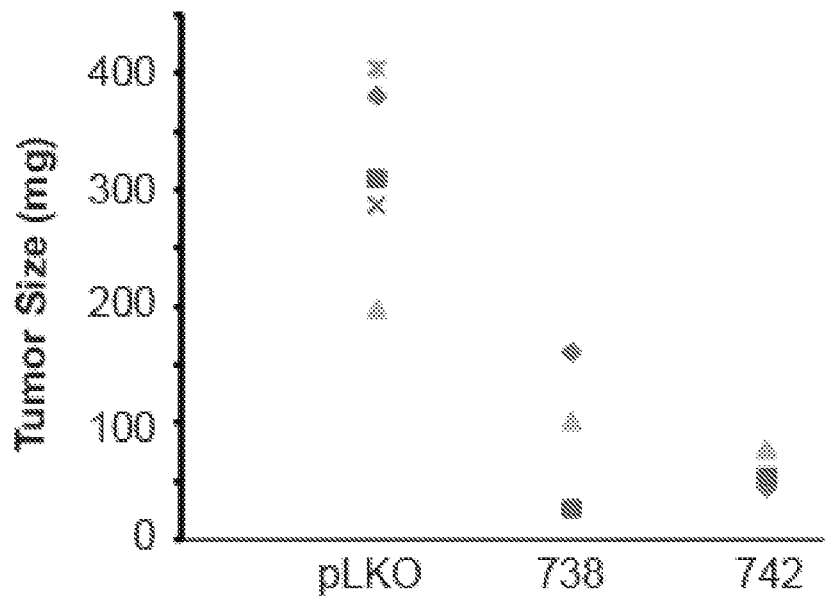
FIG. 16 shows that stable knockdown of endogenous ME2 levels in A549 cells suppresses tumor formation. Stable knockdown of ME2 in A549 cells led to reduced tumor size in nude mice. Approximately 5×10$^6$ ME2 deficient cells from 2 ME2 specific shRNAs (738 cells with shME2-1 and 742 cells with shME2-3) or control pLKO cells were subcutaneously implanted into female athymic nude mice. Tumor-bearing mice were sacrificed after 6 weeks, and the tumors were dissected and weighed.

To determine the effect of ME2 deficiency in vivo, A549 ME2 knockdown cells and A549 control cells were injected subcutaneously in the flanks of mice. Ten mice were used in each treatment group. There was a marked reduction of tumor size generated by the ME2 deficient cells compared to control cells (FIG. 16). Tumor histology indicated that significant differentiation had occurred in the ME2 deficient tumors, as evidenced by primitive glandular structures present in the ME2 deficient tumors as compared to their absence in the control tumors. In support of this, we found a marked increase in ZO-1 expression in ME2 deficient tumors. Accordingly, these data show that ME2 inhibitors could be used to alter tumor growth and/or differentiation in vivo.

Further in vivo models can be developed to assess the effect of ME2 inhibition. For example, homozygous ME2-$A^{fl/fl}$ animals can be crossed with genetically defined tumor models that are designed with targeted dysregulation in tumor oncogenic or tumor suppressor pathways involved in lung tumorigenesis. In another example, tamoxifen regulated conditional ME2 mice are generated: $Cre^{tm}$-ME2-$A^{fl/fl}$ (homozygous) and $Cre^{tm}$-ME2-$A^{fl/+}$ (heterozygous). In these examples, ME2$^{fl/+}$ mice having a heterozygous status of modified ME2 allele are generated, where these mice can be crossed with homozygous tamoxifen inducible cre-recombinase ($Cre^{tm}$) mice to generate $Cre^{tm}$-ME2-$A^{fl/+}$ and where $Cre^{tm}$-ME2-$A^{fl/+}$ are crossed among themselves to generate homozygous $Cre^{tm}$-ME2-$A^{fl/fl}$ mice.

Example 7

Knockdown of ME2 Increases Sensitivity to Cisplatin Treatment

Figure 17:
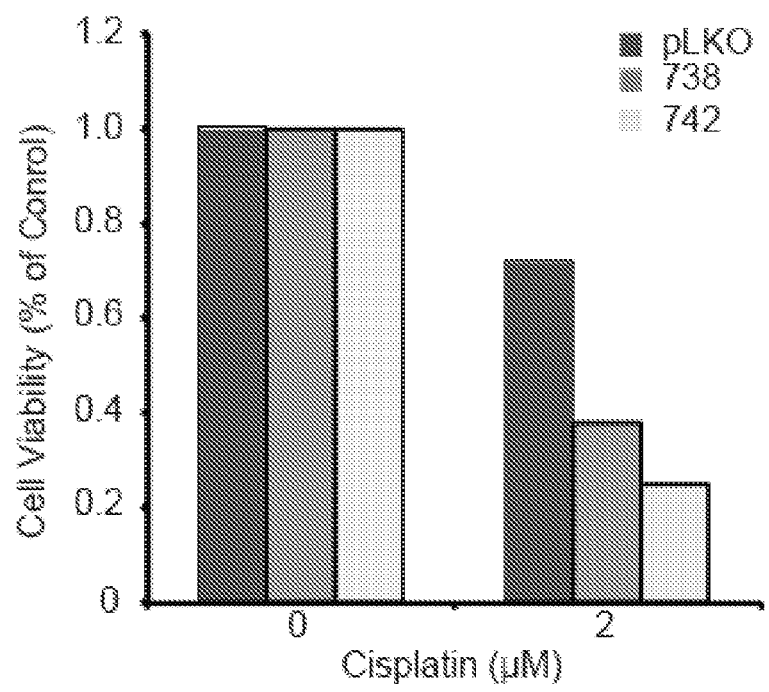
FIG. 17 shows that depletion of ME2 renders cells more sensitive to cisplatin treatment. 1×10$^4$ cells/ml of ME2 knockdown cells (738 cells with shME2-1 and 742 cells with shME2-3) and control cells were plated in 6-well plates. After 24 hours, cells were treated with 2 μM cisplatin. After 72 hours, cells were stained with trypan blue and live cells were counted.

To explore whether knockdown of ME2 may benefit tumor therapy in the context of a drug (cisplatin) for NSCLC, we investigated the effect of cisplatin on A549 cells with or without ME2 depletion. Our data suggest that deficiency of ME2 increases the sensitivity of A549 cells to cisplatin treatment (FIG. 17). Therefore, these data show that a combination of an ME2 inhibitor and an anticancer agent, e.g., cisplatin, can be used to increase the effectiveness of cancer treatment.

Example 8

Figure 18:
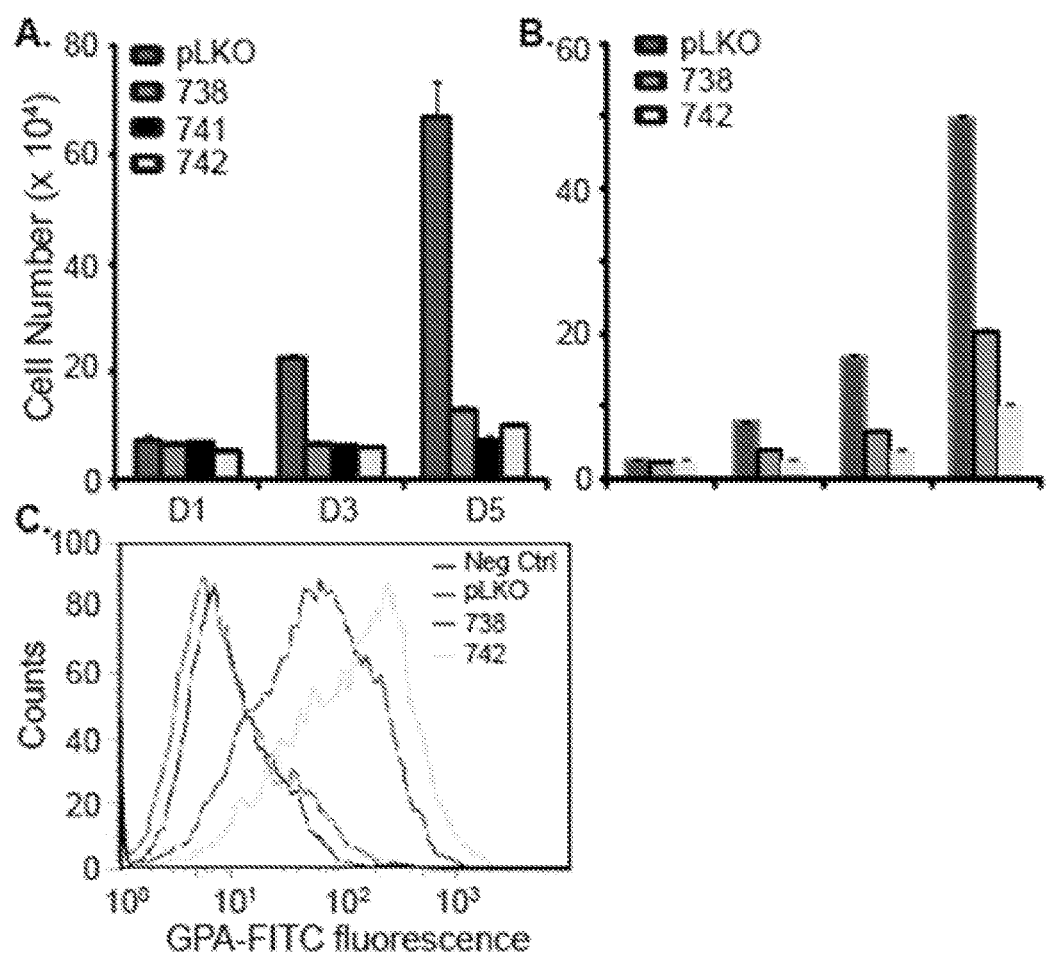
FIG. 18 shows that knockdown of ME2 impacts proliferation and differentiation of MCF-7, WM983-B, and K562 cells. A: Knockdown of ME2 inhibits MCF-7 cells proliferation. Data is shown for 738 cells with shME2-1, 741 cells with shME2-2, and 742 cells with shME2-3. B: Knockdown of ME2 inhibits WM983-B cell differentiation. Data is shown for 738 cells with shME2-1 and 742 cells with shME2-3. C: Knockdown of ME2 induces K562 differentiation as assessed by expression of the erythroid marker glycophorin A (GPA). Data is shown for 738 cells with shME2-1 and 742 cells with shME2-3.

Knockdown of ME2 Impacts Cell Proliferation and Differentiation in Various Cancer Cell Lines To determine whether knockdown of ME2 has biological effects on other tumor cell types and thus potentially increase the impact of our studies in lung cancer, we investigated the effects of ME2 knockdown in vitro in several types of tumor cells. Our data indicate that depletion of ME2 can also markedly inhibit cell proliferation of MCF-7 (breast) cells (FIG. 18A) and WM983-B (melanoma) cells (FIG. 18B). As discussed in Example 1 above, ME2 knockdown induced K562 cells differentiation along the erythroid lineage (FIG. 18C) and markedly inhibited proliferation. In addition, ME2 expression is present in comparison to normal adjacent tissue in a majority of solid tumor samples tested. Accordingly, these data show that knockdown of ME2, e.g., by using any ME2 inhibitor described herein, could be implemented to treat cancer, e.g., any cancer described herein.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A method of treating or prophylactically treating a subject having cancer, said method comprising administering to said subject a malic enzyme 2 inhibitor in an amount sufficient to treat said cancer, wherein the malic enzyme 2 inhibitor is an RNAi agent or antisense oligonucleotide that comprises any one of SEQ ID NOs:1-36.

2. The method of claim 1, wherein said cancer is selected from the group consisting of leukemia, breast cancer, and skin cancer.

3. The method of claim 2, wherein said cancer is leukemia and said leukemia is selected from the group consisting of chronic myeloid leukemia, acute myeloid leukemia, acute lymphoblastic leukemia, and chronic lymphocytic leukemia.

4. The method of claim 1, wherein said cancer is lung cancer and said lung cancer is selected from the group consisting of non-small cell lung cancer, small-cell lung cancer, carcinoid, sarcoma, squamous cell cancer, adenocarcinoma, and large cell carcinoma.

5. The method of claim 1, wherein said method further comprises administering to said subject an anticancer agent and wherein said malic enzyme 2 inhibitor and said anticancer agent are together in an amount sufficient to treat said cancer.

6. The method of claim 5, wherein said anticancer agent is one or more of a chemotherapeutic agent, an immunomodulatory agent, an antiangiogenic agent, a mitotic inhibitor, a nucleoside analog, a DNA intercalating agent, a topoisomerase analog, or a folate antimetabolite.

7. The method of claim 6, wherein said anticancer agent is said chemotherapeutic agent selected from the group consisting of cisplatin, carboplatin, chlorambucil, melphalan, nedaplatin, oxaliplatin, triplatin tetranitrate, satraplatin, imatinib, nilotinib, dasatinib, and radicicol.

8. A method of treating or prophylactically treating a subject having cancer, said method comprising administering to said subject a malic enzyme 2 inhibitor comprising a nucleic acid sequence identical to the sequence of any one of SEQ ID NOs:1-36 in an amount sufficient to treat said cancer.

9. The method of claim 8, wherein said cancer is selected from the group consisting of leukemia, brain cancer, bladder cancer, breast cancer, cervical cancer, colorectal cancer, endometrial cancer, esophageal cancer, head and neck cancer, liver cancer, lung cancer, lymphoma, ovarian cancer, pancreatic cancer, prostate cancer, renal cancer, skin cancer, stomach cancer, testis cancer, thyroid cancer, and urothelial cancer.

10. The method of claim 9, wherein said cancer is leukemia and said leukemia is selected from the group consisting of chronic myeloid leukemia, acute myeloid leukemia, acute lymphoblastic leukemia, and chronic lymphocytic leukemia.

11. The method of claim 9, wherein said cancer is lung cancer and said lung cancer is selected from the group consisting of non-small cell lung cancer, small-cell lung cancer, carcinoid, sarcoma, squamous cell cancer, adenocarcinoma, and large cell carcinoma.

12. The method of claim 8, wherein said method further comprises administering to said subject an anticancer agent and wherein said malic enzyme 2 inhibitor and said anticancer agent are together in an amount sufficient to treat said cancer.

13. The method of claim 12, wherein said anticancer agent is one or more of a chemotherapeutic agent, an immunomodulatory agent, an antiangiogenic agent, a mitotic inhibitor, a nucleoside analog, a DNA intercalating agent, a topoisomerase analog, or a folate antimetabolite.

14. The method of claim 13, wherein said anticancer agent is a chemotherapeutic agent selected from the group consisting of cisplatin, carboplatin, chlorambucil, melphalan, nedaplatin, oxaliplatin, triplatin tetranitrate, satraplatin, imatinib, nilotinib, dasatinib, and radicicol.

* * * * *

SEQUENCE LISTING

```
<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
cggcatatta gtgacagtgt t                                                 21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
cccagtatgg acacatcttt a                                                 21

<210> SEQ ID NO 3
<211> LENGTH: 21
<212> TYPE: DNA
<213> ORGANISM: Artificial Sequence
<220> FEATURE:
<223> OTHER INFORMATION: Synthetic construct
```

<400> SEQUENCE: 3
gcacggctga agaagcatat a                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic construct

<400> SEQUENCE: 4
gcacggctga agaagcatat a                                              21

<210> SEQ ID NO 5
<211> LENGTH: 29
<212> TYPE: DNA
<213> ORGANISM: Artificial Sequence
<220> FEATURE:
<223> OTHER INFORMATION: Synthetic construct

<400> SEQUENCE: 5
gaagactttg gaaatcataa tgcattcag                                      29

<210> SEQ ID NO 6
<211> LENGTH: 29
<212> TYPE: DNA
<213> ORGANISM: Artificial Sequence
<220> FEATURE:
<223> OTHER INFORMATION: Synthetic construct

<400> SEQUENCE: 6
gcgagtcttt acaccaggtc aaggaaaca                                      29

<210> SEQ ID NO 7
<211> LENGTH: 29
<212> TYPE: DNA
<213> ORGANISM: Artificial Sequence
<220> FEATURE:
<223> OTHER INFORMATION: Synthetic construct

<400> SEQUENCE: 7
ccaggtgtgg ctttagctgt tattctctg                                      29

<210> SEQ ID NO 8
<211> LENGTH: 97
<212> TYPE: DNA
<213> ORGANISM: Artificial Sequence
<220> FEATURE:
<223> OTHER INFORMATION: Synthetic construct

<400> SEQUENCE: 8
tgctgttgac agtgagcgcg ccacttatgc tgaacccaag tagtgaagcc acagatgtac    60
ttgggttcag cataagtggc ttgcctactg cctcgga                             97

<210> SEQ ID NO 9
<211> LENGTH: 97
<212> TYPE: DNA
<213> ORGANISM: Artificial Sequence
<220> FEATURE:
<223> OTHER INFORMATION: Synthetic construct

<400> SEQUENCE: 9
tgctgttgac agtgagcgac aagatgacat tgagagttta tagtgaagcc acagatgtat    60

```
aaactctcaa tgtcatcttg ctgcctactg cctcgga                              97
```

<210> SEQ ID NO 10
<211> LENGTH: 97
<212> TYPE: DNA
<213> ORGANISM: Artificial Sequence
<220> FEATURE:
<223> OTHER INFORMATION: Synthetic construct

<400> SEQUENCE: 10

```
tgctgttgac agtgagcgcg gtcaaggaaa caatgtttat tagtgaagcc acagatgtaa    60
taaacattgt ttccttgacc ttgcctactg cctcgga                             97
```

<210> SEQ ID NO 11
<211> LENGTH: 97
<212> TYPE: DNA
<213> ORGANISM: Artificial Sequence
<220> FEATURE:
<223> OTHER INFORMATION: Synthetic construct

<400> SEQUENCE: 11

```
tgctgttgac agtgagcgat aggaaaactt tgtttgtata tagtgaagcc acagatgtat    60
atacaaacaa agttttccta ctgcctactg cctcgga                             97
```

<210> SEQ ID NO 12
<211> LENGTH: 97
<212> TYPE: DNA
<213> ORGANISM: Artificial Sequence
<220> FEATURE:
<223> OTHER INFORMATION: Synthetic construct

<400> SEQUENCE: 12

```
tgctgttgac agtgagcgac agaaacgaga tcgcacacaa tagtgaagcc acagatgtat    60
tgtgtgcgat ctcgtttctg gtgcctactg cctcgga                             97
```

<210> SEQ ID NO 13
<211> LENGTH: 97
<212> TYPE: DNA
<213> ORGANISM: Artificial Sequence
<220> FEATURE:
<223> OTHER INFORMATION: Synthetic construct

<400> SEQUENCE: 13

```
tgctgttgac agtgagcgac tgaagaagca tatacactta tagtgaagcc acagatgtat    60
aagtgtatat gcttcttcag ctgcctactg cctcgga                             97
```

<210> SEQ ID NO 14
<211> LENGTH: 58
<212> TYPE: DNA
<213> ORGANISM: Artificial Sequence
<220> FEATURE:
<223> OTHER INFORMATION: Synthetic construct

<400> SEQUENCE: 14

```
ccggcggcat attagtgaca gtgttctcga gaacactgtc actaatatgc cgttttttg     58
```

<210> SEQ ID NO 15
<211> LENGTH: 58
<212> TYPE: DNA
<213> ORGANISM: Artificial Sequence
<220> FEATURE:
<223> OTHER INFORMATION: Synthetic construct

<400> SEQUENCE: 15
ccgggaaagc tattactgac agatactcga gtatctgtca gtaatagctt tcttttg    58

<210> SEQ ID NO 16
<211> LENGTH: 58
<212> TYPE: DNA
<213> ORGANISM: Artificial Sequence
<220> FEATURE:
<223> OTHER INFORMATION: Synthetic construct

<400> SEQUENCE: 16
ccggcccagt atggacacat ctttactcga gtaaagatgt gtccatactg ggttttg    58

<210> SEQ ID NO 17
<211> LENGTH: 58
<212> TYPE: DNA
<213> ORGANISM: Artificial Sequence
<220> FEATURE:
<223> OTHER INFORMATION: Synthetic construct

<400> SEQUENCE: 17
ccgggcacgg ctgaagaagc atatactcga gtatatgctt cttcagccgt gcttttg    58

<210> SEQ ID NO 18
<211> LENGTH: 58
<212> TYPE: DNA
<213> ORGANISM: Artificial Sequence
<220> FEATURE:
<223> OTHER INFORMATION: Synthetic construct

<400> SEQUENCE: 18
ccggtacttt ggcatgtcga catttctcga gaaatgtcga catgccaaag tattttg    58

<210> SEQ ID NO 19
<211> LENGTH: 58
<212> TYPE: DNA
<213> ORGANISM: Artificial Sequence
<220> FEATURE:
<223> OTHER INFORMATION: Synthetic construct

<400> SEQUENCE: 19
ccggagttct tacagagcta ctaaactcga gtttagtagc tctgtaagaa cttttg    58

<210> SEQ ID NO 20
<211> LENGTH: 19
<212> TYPE: DNA
<213> ORGANISM: Artificial Sequence
<220> FEATURE:
<223> OTHER INFORMATION: Synthetic construct

<400> SEQUENCE: 20
ccacttatgc tgaacccaa    19

<210> SEQ ID NO 21
<211> LENGTH: 19
<212> TYPE: DNA
<213> ORGANISM: Artificial Sequence
<220> FEATURE:
<223> OTHER INFORMATION: Synthetic construct

<400> SEQUENCE: 21
ggtgaatacg acttgggtt    19

<210> SEQ ID NO 22
<211> LENGTH: 19
<212> TYPE: DNA

<213> ORGANISM: Artificial Sequence
<220> FEATURE:
<223> OTHER INFORMATION: Synthetic construct

<400> SEQUENCE: 22
gtcaaggaaa caatgttta         19

<210> SEQ ID NO 23
<211> LENGTH: 18
<212> TYPE: DNA
<213> ORGANISM: Artificial Sequence
<220> FEATURE:
<223> OTHER INFORMATION: Synthetic construct

<400> SEQUENCE: 23
agttcctttg ttacaaat         18

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
aagatgacat tgagagttt         19

<210> SEQ ID NO 25
<211> LENGTH: 19
<212> TYPE: DNA
<213> ORGANISM: Artificial Sequence
<220> FEATURE:
<223> OTHER INFORMATION: Synthetic construct

<400> SEQUENCE: 25
ttctactgta actctcaaa         19

<210> SEQ ID NO 26
<211> LENGTH: 19
<212> TYPE: DNA
<213> ORGANISM: Artificial Sequence
<220> FEATURE:
<223> OTHER INFORMATION: Synthetic construct

<400> SEQUENCE: 26
tgaagaagca tatacactt         19

<210> SEQ ID NO 27
<211> LENGTH: 19
<212> TYPE: DNA
<213> ORGANISM: Artificial Sequence
<220> FEATURE:
<223> OTHER INFORMATION: Synthetic construct

<400> SEQUENCE: 27
acttcttcgt atatgtgaa         19

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
aggaaaactt tgtttgtat         19

<210> SEQ ID NO 29
<211> LENGTH: 19
<212> TYPE: DNA
<213> ORGANISM: Artificial Sequence
<220> FEATURE:
<223> OTHER INFORMATION: Synthetic construct

<400> SEQUENCE: 29
tccttttgaa acaaacata                                              19

<210> SEQ ID NO 30
<211> LENGTH: 19
<212> TYPE: DNA
<213> ORGANISM: Artificial Sequence
<220> FEATURE:
<223> OTHER INFORMATION: Synthetic construct

<400> SEQUENCE: 30
agaaacgaga tcgcacaca                                              19

<210> SEQ ID NO 31
<211> LENGTH: 19
<212> TYPE: DNA
<213> ORGANISM: Artificial Sequence
<220> FEATURE:
<223> OTHER INFORMATION: Synthetic construct

<400> SEQUENCE: 31
tctttgctct agcgtgtgt                                              19

<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
gccgtataat cactgtcaca a                                           21

<210> SEQ ID NO 33
<211> LENGTH: 21
<212> TYPE: DNA
<213> ORGANISM: Artificial Sequence
<220> FEATURE:
<223> OTHER INFORMATION: Synthetic construct

<400> SEQUENCE: 33
gaaagctatt actgacagat a                                           21

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
ctttcgataa tgactgtcta t                                           21

<210> SEQ ID NO 35
<211> LENGTH: 21
<212> TYPE: DNA
<213> ORGANISM: Artificial Sequence
<220> FEATURE:

-continued

<223> OTHER INFORMATION: Synthetic construct

<400> SEQUENCE: 35
gggtcatacc tgtgtagaaa t                                            21

<210> SEQ ID NO 36
<211> LENGTH: 21
<212> TYPE: DNA
<213> ORGANISM: Artificial Sequence
<220> FEATURE:
<223> OTHER INFORMATION: Synthetic construct

<400> SEQUENCE: 36
cgtgccgact tcttcgtata t                                            21

<210> SEQ ID NO 37
<211> LENGTH: 126
<212> TYPE: PRT
<213> ORGANISM: Artificial Sequence
<220> FEATURE:
<223> OTHER INFORMATION: Synthetic construct

<400> SEQUENCE: 37

Asp Gly Arg Val Phe Thr Pro Gly Gln Gly Asn Asn Val Tyr Ile Phe
 1               5                  10                  15

Pro Gly Val Ala Leu Ala Val Ile Leu Cys Asn Thr Arg His Ile Ser
            20                  25                  30

Asp Ser Val Phe Leu Glu Ala Ala Lys Ala Leu Thr Ser Gln Leu Thr
        35                  40                  45

Asp Glu Leu Ala Gln Gly Arg Leu Tyr Pro Pro Leu Ala Asn Ile
    50                  55                  60

Gln Glu Val Ser Ile Asn Ile Ala Ile Lys Val Thr Glu Tyr Leu Tyr
65                  70                  75                  80

Ala Asn Lys Met Ala Phe Arg Tyr Pro Glu Pro Glu Asp Lys Ala Lys
                85                  90                  95

Tyr Val Lys Glu Arg Thr Trp Arg Ser Glu Tyr Asp Ser Leu Leu Pro
            100                 105                 110

Asp Val Tyr Glu Trp Pro Glu Ser Ala Ser Ser Pro Val
        115                 120                 125

<210> SEQ ID NO 38
<211> LENGTH: 129
<212> TYPE: PRT
<213> ORGANISM: Artificial Sequence
<220> FEATURE:
<223> OTHER INFORMATION: Synthetic construct

<400> SEQUENCE: 38

Lys Val Ile Ser Lys Pro Ile Ser Glu His Lys Ile Leu Phe Leu Gly
 1               5                  10                  15

Ala Gly Glu Ala Ala Leu Gly Ile Ala Asn Leu Ile Val Met Ser Met
            20                  25                  30

Val Glu Asn Gly Leu Ser Glu Gln Glu Ala Gln Lys Ile Trp Met
        35                  40                  45

Phe Asp Lys Tyr Gly Leu Leu Val Lys Gly Arg Lys Ala Lys Ile Asp
    50                  55                  60

Ser Tyr Gln Glu Pro Phe Thr His Ser Ala Pro Glu Ser Ile Pro Asp
65                  70                  75                  80

Thr Phe Glu Asp Ala Val Asn Ile Leu Lys Pro Ser Thr Ile Ile Gly
                85                  90                  95

Val Ala Gly Ala Gly Arg Leu Phe Thr Pro Asp Val Ile Arg Ala Met
            100                 105                 110

Ala Ser Ile Asn Glu Arg Pro Val Ile Phe Ala Leu Ser Asn Pro Thr
        115                 120                 125

Ala

<210> SEQ ID NO 39
<211> LENGTH: 25
<212> TYPE: DNA
<213> ORGANISM: Artificial Sequence
<220> FEATURE:
<223> OTHER INFORMATION: Synthetic construct

<400> SEQUENCE: 39
gcctcttcaa tttctacgag gactt                                            25

<210> SEQ ID NO 40
<211> LENGTH: 4638
<212> TYPE: DNA
<213> ORGANISM: Homo sapiens

<400> SEQUENCE: 40
accgtgggcc acgccttccg ggccccgcgg ctggccggct cctcgcgccc tcccctctct      60
cggccgctct tcgggccgcc tctgcgtgtg gggccgcccg cgccagtgtg agcctgagct     120
gacggcggct ccgggaggct cgcagaaggg gagggccggg cggcgcggga gctgagcatc     180
gccagggcgg gcggcagggc gcggcctctc cgccgggtgt accacctgtc gcggcgcgag     240
acctctggtg aaagaaaaga tgttgtcccg gttaagagta gtttccacca cttgtacttt     300
ggcatgtcga catttgcaca taaaagaaaa aggcaagcca cttatgctga acccaagaac     360
aaacaaggga atggcattta cttkacaaga acgacaaatg cttggtcttc aaggacttct     420
acctcccaaa atagagacac aagatattca agccttacga tttcatagaa acttgaagaa     480
aatgactagc cctttggaaa aatatatcta cataatggga atacaagaaa gaaatgagaa     540
attgttttat agaatactgc aagatgacat tgagagttta atgccaattg tatatacacc     600
gacggttggt cttgcctgct cccagtatgg acacatcttt agaagaccta agggattatt     660
tatttcgatc tcagacagag gtcatgttag atcaattgtg ataactggc agaaaatca     720 tgttaaggct gttgtagtga ctgatggaga gagaattctg gtcttggag atctgggtgt     780 ctatggaatg ggaattccag taggaaaact ttgtttgtat acagcttgtg caggaatacg     840
gcctgataga tgcctgccag tgtgtattga tgtgggaact gataatatcg cactcttaaa     900
agacccattt tacatgggct tgtaccagaa acgagatcgc acacaacagt atgatgacct     960
gattgatgag tttatgaaag ctattactga cagatatggc cggaacacac tcattcagtt    1020
cgaagacttt ggaaatcata atgcattcag gttcttgaga aagtaccgag aaaaatattg    1080
tactttcaat gatgatattc aagggacagc tgcagtagct ctagcaggtc ttcttgcagc    1140
acaaaaagtt attagtaaac caatctccga acacaaaatc ttattccttg gagcaggaga    1200
ggctgctctt ggaattgcaa atcttatagt tatgtctatg gtagaaaatg gcctgtcaga    1260
acaagaggca caaagaaaaa tctggatgtt tgacaagtat ggtttattag ttaagggacg    1320
gaaagcaaaa atagatagtt atcaggaacc atttactcac tcagcccag agagcatacc    1380 tgatactttt gaagatgcag tgaatatact gaagccttca actataattg gagttgcagg    1440
tgctggccgt cttttcactc ctgatgtaat cagagccatg gcctctatca atgaaaggcc    1500

-continued

```
tgtaatatttt gcattaagta atcctacagc acaggcagag tgcacggctg aagaagcata   1560
tacacttaca gagggcaggt gtttgtttgc cagtggcagt ccatttgggc cagtgaaact   1620
tacagatggg cgagtcttta caccaggtca aggaaacaat gtttatattt ttccaggtgt   1680
ggctttagct gttattctct gtaacacccg gcatattagt gacagtgttt tcctagaagc   1740
tgcaaaggcc ctgacaagcc aattgacaga tgaagagcta gcccaaggga gactttaccc   1800
accgcttgct aatattcagg aagtttctat taacattgct attaaagtta cagaatacct   1860
atatgctaat aaaatggctt tccgataccc agaacctgaa gacaaggcca aatatgttaa   1920
agaaagaaca tggcggagtg aatatgattc cctgctgcca gatgtgtatg aatggccaga   1980
atctgcatca agccctcctg tgataacaga atagaagcac tcccctgata aatactttct   2040
gtgctccagg gaaccccttt tttcagacaa gaagagataa tgtcttcagt tttatggtgt   2100
tttctgtgtt ttgttctccc tgaccacttt ggttgatgta ttttttccat gcgtctccac   2160
atctgttggg gtagacgtgt tgattgattg cattgcccac cagcacccta cagtcagata   2220
gttgtgatgc tttaattcta acatacagcc cgtaccacat ccaggagatg taaaaagtgt   2280
gtttgtgaat gtcttcactt gtactctaat tcagacttgc caaagtattt gctatttact   2340
attatgggta atactcttct ctggcctagt tcttacagag ctactaaaat agaaatttac   2400
ttttatggat agaagtacag aattttgaga agaaactaaa ttttcaccaa attttaagga   2460
aaaattgtca ttatctaaaa atgttcttat atatctgctt catcttacct tcatactctg   2520
aaattcccta tagcagacag agctagggaa atattaaaaa tttaccctat ttattttctg   2580
gaactaaatc aagccttaac tataacatta tgagagtaat gggaactact gctggcttta   2640
agtaaataaa agtcattgtt ttcaacagtg tataaaaatc atagtgtaac ctttttattt   2700
aataaatatc ttacatttaa ttgcttcagt tatgctatct tattgcccaa ctagaaattt   2760
agatttgctt atgaaaaaca catattttg ttacttctag atgattctag gagggagtat   2820 aagatacctaa atcatatggg aacatacacgt gacttttaa atctaaatta gtcatgcttc   2880
acatcaaaat gagtcatatt taactggaga aactatgccc ttattccaga actgatgctc   2940
tttattgctt gagataattt tggaatgtta ctatgatact gtttctttga atatcattag   3000
tagtgacaac tctttctcca ttgaaggcag acttaatttt tttaaaccac caacattaat   3060
ttagagctaa atgggggatga ataaggttgg tgttcatctg ggaaatgcct ttttaaatcc   3120
cagtaaaatg ggtaataatg gctatccaga acagttttct tgtgtggctt gcatattgaa   3180
gaattctaaa ggaaaatata tctgcctacc atgcttgctc ttagggaaga aaacttaaat   3240
gctcattcta ggatagtaac aacaacagat aattcatcga taatatgagc atgcacagta   3300
tttgatattg ctctgtagga aaaaagagac ttcatttttt tcatcttctg cctatgaata   3360
caaattgatt ctttttttt tttttttttt ttgagacaga gtctcactct gttaccaggc   3420
tggagtgcag tggtgtgatc tcagctcact gcaacctctg cctcccaggt tcaagcagtt   3480
ctcctgcctc agcctcccaa gtagctggga ctacaggtac acgccaccac gcccagctaa   3540 ttttgtatt tttagtagag acgggatttc accatgttgg ccaggagggt ctcgatttcc   3600
tgacctcgcg atccgcccac ctcagccttc caaagtgctg ggattacagg cgtgagccac   3660
cgcacccagc caatttttt tttttttttt tttgagacag agtctcgctt tgtcgccca   3720 gtctggagtg tagtggcatg atctctgcaa cctctgcctc ctcggttcag gcgattcttc   3780
tgccttagcc tcccaagtag ctgggattac aggcaccggc caccacccc agctaatttt   3840 tgtatttttta gtagagatgg ggtttcacca tgttggccag gctggtctca aaatcctgac   3900
```

```
ttcaggtgat ccacccactt tggcctccca aagtgctggg attacaggcg tgagccacca      3960
cacctggtcc aattcatcat aattctgaat ataatttaat aattttaaaa tggtcgcaat      4020
ggcattgcca tttggagtat gggaaaatgc agttggttaa ttcattgaac agattagtaa      4080
agtcagaagt cttttcata acatacggtc acaattcctt tcttttaatt aaagacaaaa       4140
ggtttatggg ttttggtttg tttgttttag atatggggtt ttgctatgtc acccttgctg      4200
gagggcggtg gctgttcaca ggcgtgggtc atagagcact gcagcctgga actcctgggt      4260
tcaagctctc ctcctgcctc agcctcctga gcagcttgga ctaaaggtgt gcaccaccgc      4320
acctggctga gaggcttctg tttttcatgt tccctttatc aaaacaaaat cacgcctaaa      4380
catactctct gtgtgaaatc ttgattttag ttcaacctaa gaaatataat aaatataaac      4440
ctgtttcttg cttagtgttt attgaaggca ggaacgtatg ctgaattaaa gtaattttac      4500
tacgaagttt gcttattaag tatgcctggt acagtcttca tggaagttat taagtatttt      4560
aaggaaaaaa ataggctaaa tggcatatag cctgcttaaa taaaataatt ctattttttt      4620
aaaaaaaaaa aaaaaaaa                                                   4638
```